United States Patent
Nussenzweig et al.

(10) Patent No.: US 11,325,966 B2
(45) Date of Patent: May 10, 2022

(54) BROADLY NEUTRALIZING ANTI-HIV-1 ANTIBODIES AND METHODS OF USE THEREOF

(71) Applicants: The Rockefeller University, New York, NY (US); California Institute of Technology, Pasadena, CA (US)

(72) Inventors: Michel Nussenzweig, New York, NY (US); Natalia T. Freund, New York, NY (US); Pamela J. Bjorkman, La Canada Flintridge, CA (US); Louise Scharf, Porter Ranch, CA (US)

(73) Assignees: The Rockefeller University, New York, NY (US); California Institute of Technology, Pasadena, CA (US)

( * ) Notice: Subject to any disclaimer, the term of this patent is extended or adjusted under 35 U.S.C. 154(b) by 0 days.

(21) Appl. No.: 16/473,847

(22) PCT Filed: Dec. 22, 2017

(86) PCT No.: PCT/US2017/068235
§ 371 (c)(1),
(2) Date: Jun. 26, 2019

(87) PCT Pub. No.: WO2018/125813
PCT Pub. Date: Jul. 5, 2018

(65) Prior Publication Data
US 2020/0199203 A1    Jun. 25, 2020

Related U.S. Application Data

(60) Provisional application No. 62/444,946, filed on Jan. 11, 2017, provisional application No. 62/439,339, filed on Dec. 27, 2016.

(51) Int. Cl.
*A61K 39/42* (2006.01)
*C07K 16/10* (2006.01)
(Continued)

(52) U.S. Cl.
CPC .......... *C07K 16/1045* (2013.01); *A61K 39/21* (2013.01); *A61P 31/18* (2018.01); *A61K 38/00* (2013.01); *A61K 2039/507* (2013.01)

(58) Field of Classification Search
None
See application file for complete search history.

(56) References Cited

U.S. PATENT DOCUMENTS

2003/0171562 A1  9/2003 Farnet et al.
2007/0060743 A1  3/2007 Tang et al.
(Continued)

FOREIGN PATENT DOCUMENTS

| EP | 2679596 A1 | 1/2014 |
|---|---|---|
| JP | 2015-534982 A | 12/2015 |

(Continued)

OTHER PUBLICATIONS

Rudikoff et al., "Single amino acid substitution altering antigen-binding specificity," Proc Natl Acad Sci USA 79:1979-1983 (Year: 1982).*

(Continued)

*Primary Examiner* — M Franco G Salvoza
(74) *Attorney, Agent, or Firm* — Fox Rothschild LLP

(57) ABSTRACT

This invention relates to broadly neutralizing and potent anti-HIV-1 antibodies, kits, and methods of use thereof.

16 Claims, 14 Drawing Sheets

Specification includes a Sequence Listing.

(51) Int. Cl.
  *A61K 39/21* (2006.01)
  *A61P 31/18* (2006.01)
  *A61K 38/00* (2006.01)
  *A61K 39/00* (2006.01)

(56) References Cited

U.S. PATENT DOCUMENTS

| | | |
|---|---|---|
| 2009/0286745 A1 | 11/2009 | Zurdo et al. |
| 2013/0330335 A1 | 12/2013 | Bremel et al. |
| 2015/0274813 A1 | 10/2015 | Mouquet et al. |
| 2016/0002319 A1 | 1/2016 | Killian et al. |
| 2016/0033532 A1 | 2/2016 | Wyatt et al. |
| 2020/0123236 A1 | 4/2020 | Guenaga et al. |

FOREIGN PATENT DOCUMENTS

| | | | |
|---|---|---|---|
| WO | WO-2014067642 A1 * | 5/2014 | ............ C07K 16/30 |
| WO | 2015/117008 A2 | 8/2015 | |
| WO | 2015117008 A2 | 8/2015 | |
| WO | 2016/127179 A2 | 8/2016 | |
| WO | 2018/075564 A1 | 4/2018 | |

OTHER PUBLICATIONS

Goel et al., "Plasticity within the Antigen-Combining Site May Manifest as Molecular Mimicry in the Humoral Immune Response," J. Immunol. 173: 7358-7367 (Year: 2004).*

Lloyd et al., "Modelling the human immune response: performance of a 1011 human antibody repertoire against a broad panel of therapeutically relevant antigens," Protein Engineering, Design & Selection, vol. 22, No. 3: 159-168 (Year: 2009).*

Edwards et al., "The Remarkable Flexibility of The Human Antibody Repertoire; Isolation of Over One Thousand Different Antibodies to a Single Protein, BLys," J. Mol. Biol. 334: 103-118 (Year: 2003).*

Caskey et al., "Broadly neutralizing anti-HIV-1 monoclonal antibodies in the clinic", Nature Medicine, vol. 25, 2019, pp. 547-553.

Dashti et al., "Broadly Neutralizing Antibodies against HIV: Back to Blood", Trends in Molecular Medicine, vol. 25, No. 3, 2019.

McCoy, "The expanding array of HIV broadly neutralizing antibodies", Retrovirology, 2018, 15:70.

Parsons et al., "Importance of Fc-mediated functions of anti-HIV-1 broadly neutralizing antibodies", Retrovirology, 2018, 15:58.

Possas et al., "HIV cure: global overview of bNAbs' patents and related scientific publications", Expert Opinion on Therapeutic Patents, 2018, vol. 28, No. 7, pp. 551-560.

Sok et al., "Recent progress in broadly neutralizing antibodies to HIV", Nature Immunology, 2018, vol. 19, pp. 1179-1188.

Liu et al., "Broadly neutralizing antibodies for HIV-1: effecacies, challenges and opportunities", Emerging Microbes & Infections, 2020, vol. 9.

Mahomed et al., "Clinical Trials of Broadly Neutralizing Monoclonal Antibodies for Human Immunodeficiency Virus Prevention: A Review", The Journal of Infectious Diseases, 2021, 13;223(3), pp. 370-380.

Van Gils, M.J. et al., "In vivo protection by broadly neutralizing HIV antibodies," Trends in Microbiology (Oct. 2014); 22(10): 550-551.

Stephenson, K.E. et al., "Broadly Neutralizing Antibodies for HIV Eradication," Gurr HIV/AIDS Rep (2016); 13: 31-37.

Girard, M.P. et al., "Report of the Cent Gardes HIV Vaccine Conference the B-cell Response to HIV. Part 1: Broadly Neutralizing Antibodies Fondation Mérieux Conference Center, Veyrier du Lac, France, Nov. 5-7, 2012," Vaccine (2013); 31: 2979-2983.

Yang, L. et al., "Passive Immunization against HIV/AIDS by Antibody Gene Transfer," Viruses (2014); 6: 428-447.

Yu, L. et al., "Immunologic basis for long HCDR3s in broadly neutralizing antibodies against HIV-1," Frontiers in Immunology (Jun. 2014); 5: 1-8.

Kwong, P.D. et al., "Broadly neutralizing antibodies and the search for an HIV-1 vaccine: the end of the beginning," Immunology (Sep. 2013); 13(9): 693-701.

Shingai et al., "Passive transfer of modest titers of potent and broadly neutralizing anti-HIV monoclonal antibodies block SHIV infection in macaques", Journal of Experimental Medicine, 2014, vol. 211, No. 10, pp. 2061-2074.

Horwitz et al., "HIV-1 suppression and durable control by combining single broadly neutralizing antibodies and antiretroviral drugs in humanized mice", PNAS, 2013, vol. 110, No. 41, pp. 16538-16543.

* cited by examiner

FIG. 11A
FIG. 11B
FIG. 11C
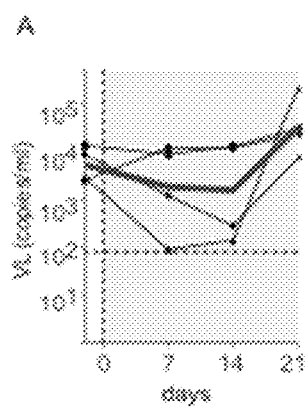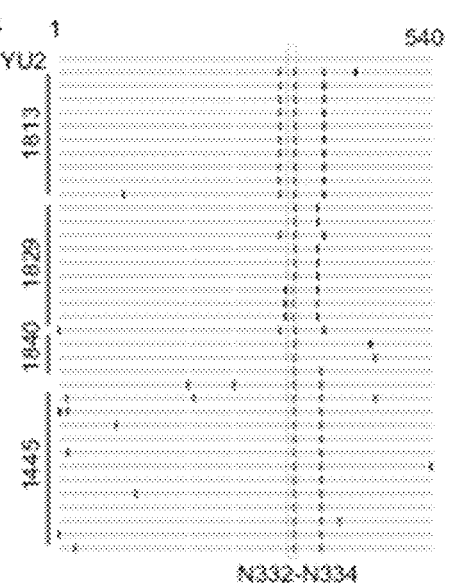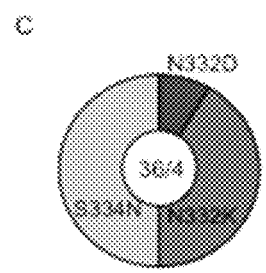

SEQUENCE LISTING

```
<160> NUMBER OF SEQ ID NOS: 128

<210> SEQ ID NO 1
<211> LENGTH: 130
<212> TYPE: PRT
<213> ORGANISM: Homo sapiens

<400> SEQUENCE: 1

Glu Val Gln Leu Arg Glu Ser Gly Pro Arg Leu Val Lys Pro Ser Glu
1               5                   10                  15

Thr Leu Ser Leu Ser Cys Asp Val Phe Gly Asp Ser Arg Pro Ser Asp
            20                  25                  30

His Ser Trp Thr Trp Val Arg Gln Pro Pro Gly Lys Ala Leu Glu Trp
        35                  40                  45

Ile Gly Asp Val His Tyr Asn Gly Asp Asn Thr Tyr Asn Pro Ser Leu
    50                  55                  60

Arg Gly Arg Val Lys Ile Asp Val Asp Arg Ser Thr His Arg Phe Ser
65                  70                  75                  80

Leu Thr Leu Lys Ser Leu Thr Ala Ala Asp Thr Gly Ile Tyr Phe Cys
                85                  90                  95

Ala Arg Asn Val Ile Arg Val Phe Gly Val Ile Ser Leu Gly Glu Trp
            100                 105                 110

Phe His Tyr Gly Met Asp Val Trp Gly Pro Gly Thr Ala Val Ile Val
        115                 120                 125

Ser Ser
    130

<210> SEQ ID NO 2
<211> LENGTH: 9
<212> TYPE: PRT
<213> ORGANISM: Homo sapiens

<400> SEQUENCE: 2

Gly Asp Ser Arg Pro Ser Asp His Ser
1               5
```

```
<210> SEQ ID NO 3
<211> LENGTH: 7
<212> TYPE: PRT
<213> ORGANISM: Homo sapiens

<400> SEQUENCE: 3

Val His Tyr Asn Gly Asp Asn
1               5

<210> SEQ ID NO 4
<211> LENGTH: 21
<212> TYPE: PRT
<213> ORGANISM: Homo sapiens

<400> SEQUENCE: 4

Asn Val Ile Arg Val Phe Gly Val Ile Ser Leu Gly Glu Trp Phe His
1               5                   10                  15

Tyr Gly Met Asp Val
            20

<210> SEQ ID NO 5
<211> LENGTH: 108
<212> TYPE: PRT
<213> ORGANISM: Homo sapiens

<400> SEQUENCE: 5

Ser Ser Glu Leu Thr Gln Ala Pro Ser Val Ser Val Ser Pro Gly Gln
1               5                   10                  15

Thr Ala Thr Ile Ala Cys Ser Gly Pro Pro Leu Ala Ser Arg Tyr Thr
                20                  25                  30

Tyr Trp Tyr Arg Gln Lys Pro Gly Gln Ala Pro Val Leu Ile Ile Phe
            35                  40                  45

Arg Asp Arg Gln Phe Pro Ser Gly Val Ser Gly Arg Phe Ser Ala Ser
        50                  55                  60

Lys Ser Gly Thr Thr Ala Thr Leu Thr Ile Arg Asp Val Gln Val Glu
65                  70                  75                  80

Asp Glu Gly Asp Tyr Tyr Cys Gln Ser Ser Asp Thr Ser Asp Ser Tyr
                85                  90                  95

Lys Met Phe Gly Gly Gly Thr Thr Leu Thr Val Leu
                100                 105

<210> SEQ ID NO 6
<211> LENGTH: 6
<212> TYPE: PRT
<213> ORGANISM: Homo sapiens

<400> SEQUENCE: 6

Pro Leu Ala Ser Arg Tyr
1               5

<210> SEQ ID NO 7
<211> LENGTH: 3
<212> TYPE: PRT
<213> ORGANISM: Homo sapiens

<400> SEQUENCE: 7

Arg Asp Arg
1

<210> SEQ ID NO 8
<211> LENGTH: 11
<212> TYPE: PRT
```

-continued

<213> ORGANISM: Homo sapiens

<400> SEQUENCE: 8

Gln Ser Ser Asp Thr Ser Asp Ser Tyr Lys Met
1               5                   10

<210> SEQ ID NO 9
<211> LENGTH: 130
<212> TYPE: PRT
<213> ORGANISM: Homo sapiens

<400> SEQUENCE: 9

Gln Val Gln Leu Arg Glu Ser Gly Pro Gly Leu Val Lys Pro Ser Glu
1               5                   10                  15

Thr Leu Ser Leu Ser Cys Thr Val Ser Asn Asp Ser Arg Pro Ser Asp
            20                  25                  30

His Ser Trp Thr Trp Val Arg Gln Ser Pro Gly Lys Ala Leu Glu Trp
        35                  40                  45

Ile Gly Asp Ile His Tyr Asn Gly Ala Thr Thr Tyr Asn Pro Ser Leu
    50                  55                  60

Arg Ser Arg Val Arg Ile Glu Leu Asp Gln Ser Ile Pro Arg Phe Ser
65                  70                  75                  80

Leu Lys Met Thr Ser Met Thr Ala Ala Asp Thr Gly Met Tyr Tyr Cys
                85                  90                  95

Ala Arg Asn Ala Ile Arg Ile Tyr Gly Val Val Ala Leu Gly Glu Trp
            100                 105                 110

Phe His Tyr Gly Met Asp Val Trp Gly Gln Gly Thr Ala Val Thr Val
        115                 120                 125

Ser Ser
    130

<210> SEQ ID NO 10
<211> LENGTH: 9
<212> TYPE: PRT
<213> ORGANISM: Homo sapiens

<400> SEQUENCE: 10

Asn Asp Ser Arg Pro Ser Asp His Ser
1               5

<210> SEQ ID NO 11
<211> LENGTH: 7
<212> TYPE: PRT
<213> ORGANISM: Homo sapiens

<400> SEQUENCE: 11

Ile His Tyr Asn Gly Ala Thr
1               5

<210> SEQ ID NO 12
<211> LENGTH: 21
<212> TYPE: PRT
<213> ORGANISM: Homo sapiens

<400> SEQUENCE: 12

Asn Ala Ile Arg Ile Tyr Gly Val Val Ala Leu Gly Glu Trp Phe His
1               5                   10                  15

Tyr Gly Met Asp Val
            20

```
<210> SEQ ID NO 13
<211> LENGTH: 108
<212> TYPE: PRT
<213> ORGANISM: Homo sapiens

<400> SEQUENCE: 13

Ser Ser Glu Leu Thr Gln Pro Pro Ser Val Ser Val Ser Pro Gly Gln
1               5                   10                  15

Thr Ala Arg Ile Thr Cys Ser Gly Ala Pro Leu Thr Ser Arg Phe Thr
            20                  25                  30

Tyr Trp Tyr Arg Gln Lys Pro Gly Gln Ala Pro Val Leu Ile Ile Ser
        35                  40                  45

Arg Ser Ser Gln Arg Ser Ser Gly Trp Ser Gly Arg Phe Ser Ala Ser
    50                  55                  60

Trp Ser Gly Thr Thr Val Thr Leu Thr Ile Arg Gly Val Gln Ala Asp
65                  70                  75                  80

Asp Glu Ala Asp Tyr Tyr Cys Gln Ser Ser Asp Thr Ser Asp Ser Tyr
                85                  90                  95

Lys Met Phe Gly Gly Gly Thr Lys Leu Thr Val Leu
            100                 105

<210> SEQ ID NO 14
<211> LENGTH: 6
<212> TYPE: PRT
<213> ORGANISM: Homo sapiens

<400> SEQUENCE: 14

Pro Leu Thr Ser Arg Phe
1               5

<210> SEQ ID NO 15
<211> LENGTH: 3
<212> TYPE: PRT
<213> ORGANISM: Homo sapiens

<400> SEQUENCE: 15

Arg Ser Ser
1

<210> SEQ ID NO 16
<211> LENGTH: 11
<212> TYPE: PRT
<213> ORGANISM: Homo sapiens

<400> SEQUENCE: 16

Gln Ser Ser Asp Thr Ser Asp Ser Tyr Lys Met
1               5                   10

<210> SEQ ID NO 17
<211> LENGTH: 130
<212> TYPE: PRT
<213> ORGANISM: Homo sapiens

<400> SEQUENCE: 17

Glu Val Gln Leu Arg Glu Ser Gly Pro Gly Leu Val Lys Pro Ser Glu
1               5                   10                  15

Thr Leu Ser Leu Ser Cys Asp Val Phe Gly Asp Ser Arg Pro Ser Asp
            20                  25                  30

His Ser Trp Thr Trp Val Arg Gln Pro Pro Gly Lys Ala Leu Glu Trp
        35                  40                  45

Ile Gly Asp Val His Tyr Asn Gly Asp Thr Thr Tyr Asn Pro Ser Leu
```

```
                    50                  55                  60
Arg Gly Arg Val Lys Ile Asp Val Asp Arg Ser Thr His Arg Phe Ser
 65                  70                  75                  80

Leu Thr Leu Asn Ser Leu Thr Ala Ala Asp Thr Gly Ile Tyr Phe Cys
                    85                  90                  95

Ala Arg Asn Val Ile Arg Val Phe Gly Val Ile Ser Leu Gly Glu Trp
                100                 105                 110

Phe His Tyr Gly Met Asp Val Trp Gly Gln Gly Thr Ala Val Thr Val
            115                 120                 125

Ser Ser
    130

<210> SEQ ID NO 18
<211> LENGTH: 9
<212> TYPE: PRT
<213> ORGANISM: Homo sapiens

<400> SEQUENCE: 18

Gly Asp Ser Arg Pro Ser Asp His Ser
1               5

<210> SEQ ID NO 19
<211> LENGTH: 7
<212> TYPE: PRT
<213> ORGANISM: Homo sapiens

<400> SEQUENCE: 19

Val His Tyr Asn Gly Asp Thr
1               5

<210> SEQ ID NO 20
<211> LENGTH: 21
<212> TYPE: PRT
<213> ORGANISM: Homo sapiens

<400> SEQUENCE: 20

Asn Val Ile Arg Val Phe Gly Val Ile Ser Leu Gly Glu Trp Phe His
1               5                   10                  15

Tyr Gly Met Asp Val
            20

<210> SEQ ID NO 21
<211> LENGTH: 108
<212> TYPE: PRT
<213> ORGANISM: Homo sapiens

<400> SEQUENCE: 21

Ser Ser Glu Leu Thr Gln Ala Pro Ser Val Ser Val Ser Pro Gly Gln
1               5                   10                  15

Thr Ala Thr Ile Ala Cys Ser Gly Pro Pro Leu Ala Ser Arg Tyr Thr
                20                  25                  30

Tyr Trp Tyr Arg Gln Lys Pro Gly Gln Ala Pro Val Leu Ile Ile Phe
            35                  40                  45

Arg Asp Arg Gln Phe Pro Ser Gly Val Ser Gly Arg Phe Ser Ala Ser
        50                  55                  60

Lys Ser Gly Thr Thr Ala Thr Leu Thr Ile Arg Asp Val Gln Val Glu
 65                  70                  75                  80

Asp Glu Gly Asp Tyr Tyr Cys Gln Ser Ser Asp Thr Ser Asp Ser Tyr
                85                  90                  95
```

```
Lys Met Phe Gly Gly Thr Thr Leu Thr Val Leu
            100                 105
```

<210> SEQ ID NO 22
<211> LENGTH: 6
<212> TYPE: PRT
<213> ORGANISM: Homo sapiens

<400> SEQUENCE: 22

```
Pro Leu Ala Ser Arg Tyr
1               5
```

<210> SEQ ID NO 23
<211> LENGTH: 3
<212> TYPE: PRT
<213> ORGANISM: Homo sapiens

<400> SEQUENCE: 23

```
Arg Asp Arg
1
```

<210> SEQ ID NO 24
<211> LENGTH: 11
<212> TYPE: PRT
<213> ORGANISM: Homo sapiens

<400> SEQUENCE: 24

```
Gln Ser Ser Asp Thr Ser Asp Ser Tyr Lys Met
1               5                   10
```

<210> SEQ ID NO 25
<211> LENGTH: 130
<212> TYPE: PRT
<213> ORGANISM: Homo sapiens

<400> SEQUENCE: 25

```
Gln Val Gln Leu Arg Glu Ser Gly Pro Gly Leu Val Lys Pro Ser Glu
1               5                   10                  15

Thr Leu Ser Leu Thr Cys Thr Val Ser Asn Asp Ser Arg Pro Ser Asp
            20                  25                  30

His Ser Trp Thr Trp Val Arg Gln Ser Pro Gly Lys Ala Leu Glu Trp
        35                  40                  45

Ile Gly Asp Ile His Tyr Asn Gly Ala Thr Thr Tyr Asn Pro Ser Leu
    50                  55                  60

Arg Ser Arg Val Arg Ile Glu Leu Asp Gln Ser Ile Pro Arg Phe Ser
65                  70                  75                  80

Leu Lys Met Thr Ser Met Thr Ala Ala Asp Thr Gly Met Tyr Tyr Cys
            85                  90                  95

Ala Arg Asn Ala Ile Arg Ile Tyr Gly Val Val Ala Leu Gly Glu Trp
            100                 105                 110

Phe His Tyr Gly Met Asp Val Trp Gly Gln Gly Thr Ala Val Thr Val
            115                 120                 125

Ser Ser
    130
```

<210> SEQ ID NO 26
<211> LENGTH: 9
<212> TYPE: PRT
<213> ORGANISM: Homo sapiens

<400> SEQUENCE: 26

Asn Asp Ser Arg Pro Ser Asp His Ser
1               5

<210> SEQ ID NO 27
<211> LENGTH: 7
<212> TYPE: PRT
<213> ORGANISM: Homo sapiens

<400> SEQUENCE: 27

Ile His Tyr Asn Gly Ala Thr
1               5

<210> SEQ ID NO 28
<211> LENGTH: 21
<212> TYPE: PRT
<213> ORGANISM: Homo sapiens

<400> SEQUENCE: 28

Asn Ala Ile Arg Ile Tyr Gly Val Val Ala Leu Gly Glu Trp Phe His
1               5                   10                  15

Tyr Gly Met Asp Val
            20

<210> SEQ ID NO 29
<211> LENGTH: 108
<212> TYPE: PRT
<213> ORGANISM: Homo sapiens

<400> SEQUENCE: 29

Ser Ser Glu Leu Thr Gln Pro Pro Ser Val Ser Val Ser Pro Gly Gln
1               5                   10                  15

Thr Ala Lys Ile Thr Cys Ser Gly Ala Ala Leu Thr Ser Arg Phe Thr
            20                  25                  30

Tyr Trp Tyr Arg Gln Lys Pro Gly Gln Ala Pro Val Leu Ile Ile Ser
        35                  40                  45

Arg Thr Ser Gln Arg Ser Ser Gly Trp Ser Gly Arg Phe Ser Ala Ser
    50                  55                  60

Trp Ser Gly Thr Thr Val Thr Leu Thr Ile Arg Gly Val Gln Ala Asp
65                  70                  75                  80

Asp Glu Gly Asp Tyr Tyr Cys Gln Ser Ser Asp Thr Ser Asp Ser Tyr
                85                  90                  95

Lys Met Phe Gly Gly Gly Thr Lys Leu Thr Val Leu
            100                 105

<210> SEQ ID NO 30
<211> LENGTH: 6
<212> TYPE: PRT
<213> ORGANISM: Homo sapiens

<400> SEQUENCE: 30

Ala Leu Thr Ser Arg Phe
1               5

<210> SEQ ID NO 31
<211> LENGTH: 3
<212> TYPE: PRT
<213> ORGANISM: Homo sapiens

<400> SEQUENCE: 31

Arg Thr Ser
1

<210> SEQ ID NO 32
<211> LENGTH: 11
<212> TYPE: PRT
<213> ORGANISM: Homo sapiens

<400> SEQUENCE: 32

Gln Ser Ser Asp Thr Ser Asp Ser Tyr Lys Met
1               5                   10

<210> SEQ ID NO 33
<211> LENGTH: 130
<212> TYPE: PRT
<213> ORGANISM: Homo sapiens

<400> SEQUENCE: 33

Glu Val Gln Leu Arg Glu Ser Gly Pro Gly Leu Val Lys Pro Ser Gly
1               5                   10                  15

Asn Met Ala Leu Thr Cys Thr Ile Ser Gly Asp Ser Arg Pro Ser Asp
            20                  25                  30

His Ser Trp Thr Trp Val Arg Gln Ser Pro Gly Lys Ala Leu Glu Trp
        35                  40                  45

Ile Gly Asp Ile His Tyr Gly Asp Ile Thr Tyr Asn Pro Ser Leu
    50                  55                  60

Arg Ser Arg Val Lys Leu Glu Val Asp Thr Ser Thr Asn Arg Phe Phe
65                  70                  75                  80

Leu Lys Met Thr Ser Leu Thr Val Ala Asp Thr Gly Ile Tyr Phe Cys
                85                  90                  95

Ala Arg Asn Val Ile Arg Val Phe Gly Val Ile Ala Leu Gly Glu Trp
            100                 105                 110

Phe His Tyr Gly Met Asp Val Trp Gly Gln Gly Thr Ala Ile Thr Val
        115                 120                 125

Ser Pro
    130

<210> SEQ ID NO 34
<211> LENGTH: 9
<212> TYPE: PRT
<213> ORGANISM: Homo sapiens

<400> SEQUENCE: 34

Gly Asp Ser Arg Pro Ser Asp His Ser
1               5

<210> SEQ ID NO 35
<211> LENGTH: 7
<212> TYPE: PRT
<213> ORGANISM: Homo sapiens

<400> SEQUENCE: 35

Ile His Tyr Gly Gly Asp Ile
1               5

<210> SEQ ID NO 36
<211> LENGTH: 21
<212> TYPE: PRT
<213> ORGANISM: Homo sapiens

<400> SEQUENCE: 36

Asn Val Ile Arg Val Phe Gly Val Ile Ala Leu Gly Glu Trp Phe His
1               5                   10                  15

-continued

Tyr Gly Met Asp Val
            20

<210> SEQ ID NO 37
<211> LENGTH: 108
<212> TYPE: PRT
<213> ORGANISM: Homo sapiens

<400> SEQUENCE: 37

Ser Ser Glu Leu Thr Gln Thr Pro Ser Val Thr Val Ser Pro Gly Glu
1               5                   10                  15

Thr Ala Arg Ile Ala Cys Ser Gly Pro Pro Leu Ala Ser Arg Tyr Cys
            20                  25                  30

Tyr Trp Tyr Arg Gln Lys Pro Gly Gln Ala Pro Val Leu Ile Ile Phe
        35                  40                  45

Arg Asp Arg Gln Phe Ser Ser Gly Met Ser Gly Arg Phe Ala Ser Ser
    50                  55                  60

His Ser Gly Thr Thr Val Thr Leu Thr Ile Arg Asp Val Arg Val Glu
65                  70                  75                  80

Asp Glu Ala Asp Tyr Tyr Cys Gln Ser Ser Asp Ile Asn Asp Ser Tyr
                85                  90                  95

Lys Met Phe Gly Gly Gly Thr Lys Val Thr Val Leu
            100                 105

<210> SEQ ID NO 38
<211> LENGTH: 6
<212> TYPE: PRT
<213> ORGANISM: Homo sapiens

<400> SEQUENCE: 38

Pro Leu Ala Ser Arg Tyr
1               5

<210> SEQ ID NO 39
<211> LENGTH: 3
<212> TYPE: PRT
<213> ORGANISM: Homo sapiens

<400> SEQUENCE: 39

Arg Asp Arg
1

<210> SEQ ID NO 40
<211> LENGTH: 11
<212> TYPE: PRT
<213> ORGANISM: Homo sapiens

<400> SEQUENCE: 40

Gln Ser Ser Asp Ile Asn Asp Ser Tyr Lys Met
1               5                   10

<210> SEQ ID NO 41
<211> LENGTH: 130
<212> TYPE: PRT
<213> ORGANISM: Homo sapiens

<400> SEQUENCE: 41

Glu Val Gln Leu Arg Glu Ser Gly Pro Gly Leu Val Lys Pro Ser Gly
1               5                   10                  15

Asn Met Ala Leu Thr Cys Thr Ile Ser Gly Asp Ser Arg Pro Ser Asp
            20                  25                  30

His Ser Trp Thr Trp Val Arg Gln Ser Pro Gly Lys Thr Leu Glu Trp
             35                  40                  45

Ile Gly Asp Ile His Tyr Gly Gly Asp Ile Thr Tyr Asn Pro Ser Leu
 50                  55                  60

Arg Ser Arg Val Lys Leu Glu Val Asp Thr Ser Ser Asn Arg Phe Phe
 65                  70                  75                  80

Leu Lys Met Thr Ser Leu Thr Val Ala Asp Thr Gly Ile Tyr Phe Cys
                 85                  90                  95

Ala Arg Asn Val Ile Arg Val Phe Gly Val Ile Ala Leu Gly Glu Trp
                100                 105                 110

Phe His Tyr Gly Met Asp Val Trp Gly Gln Gly Thr Ala Ile Thr Val
            115                 120                 125

Ser Pro
    130

<210> SEQ ID NO 42
<211> LENGTH: 9
<212> TYPE: PRT
<213> ORGANISM: Homo sapiens

<400> SEQUENCE: 42

Gly Asp Ser Arg Pro Ser Asp His Ser
 1               5

<210> SEQ ID NO 43
<211> LENGTH: 7
<212> TYPE: PRT
<213> ORGANISM: Homo sapiens

<400> SEQUENCE: 43

Ile His Tyr Gly Gly Asp Ile
 1               5

<210> SEQ ID NO 44
<211> LENGTH: 21
<212> TYPE: PRT
<213> ORGANISM: Homo sapiens

<400> SEQUENCE: 44

Asn Val Ile Arg Val Phe Gly Val Ile Ala Leu Gly Glu Trp Phe His
 1               5                  10                  15

Tyr Gly Met Asp Val
            20

<210> SEQ ID NO 45
<211> LENGTH: 108
<212> TYPE: PRT
<213> ORGANISM: Homo sapiens

<400> SEQUENCE: 45

Ser Ser Glu Leu Thr Gln Thr Ala Ser Val Thr Val Ser Pro Gly Glu
 1               5                  10                  15

Thr Ala Arg Ile Ala Cys Ser Gly Pro Pro Leu Ala Ser Arg Tyr Cys
                 20                  25                  30

Tyr Trp Tyr Arg Gln Lys Pro Gly Gln Ala Pro Val Leu Ile Ile Phe
             35                  40                  45

Arg Asp Arg Gln Phe Ser Ser Gly Ile Ser Gly Arg Phe Ser Ser Ser
 50                  55                  60

Gln Ser Gly Thr Thr Val Thr Leu Thr Ile Arg Asp Val Arg Val Glu
 65                  70                  75                  80

Asp Glu Ala Asp Tyr Tyr Cys Gln Ser Ser Asp Thr Ser Asp Ser Phe
                85                  90                  95

Lys Met Phe Gly Gly Gly Thr Lys Leu Thr Val Leu
            100                 105

<210> SEQ ID NO 46
<211> LENGTH: 6
<212> TYPE: PRT
<213> ORGANISM: Homo sapiens

<400> SEQUENCE: 46

Pro Leu Ala Ser Arg Tyr
1               5

<210> SEQ ID NO 47
<211> LENGTH: 3
<212> TYPE: PRT
<213> ORGANISM: Homo sapiens

<400> SEQUENCE: 47

Arg Asp Arg
1

<210> SEQ ID NO 48
<211> LENGTH: 11
<212> TYPE: PRT
<213> ORGANISM: Homo sapiens

<400> SEQUENCE: 48

Gln Ser Ser Asp Thr Ser Asp Ser Phe Lys Met
1               5                   10

<210> SEQ ID NO 49
<211> LENGTH: 130
<212> TYPE: PRT
<213> ORGANISM: Homo sapiens

<400> SEQUENCE: 49

Gln Val Gln Leu Arg Glu Ser Gly Pro Gly Leu Val Lys Pro Ser Gly
1               5                   10                  15

Asn Met Ala Leu Thr Cys Thr Ile Ser Gly Asp Ser Arg Pro Ser Asp
            20                  25                  30

His Ser Trp Thr Trp Val Arg Gln Ser Pro Gly Lys Ala Leu Glu Trp
        35                  40                  45

Ile Gly Asp Ile His Tyr Gly Asp Ile Thr Tyr Asn Pro Ser Leu
    50                  55                  60

Arg Ser Arg Val Glu Leu Glu Val Asp Arg Ser Thr Asn Arg Phe Phe
65                  70                  75                  80

Leu Lys Met Thr Ser Leu Ser Val Ala Asp Thr Gly Met Tyr Phe Cys
                85                  90                  95

Ala Arg Asn Val Ile Arg Val Phe Gly Val Ile Ala Leu Gly Glu Trp
            100                 105                 110

Phe His Tyr Gly Met Asp Val Trp Gly Gln Gly Thr Ala Ile Thr Val
        115                 120                 125

Ser Pro
    130

<210> SEQ ID NO 50
<211> LENGTH: 9
<212> TYPE: PRT

```
<213> ORGANISM: Homo sapiens

<400> SEQUENCE: 50

Gly Asp Ser Arg Pro Ser Asp His Ser
1               5

<210> SEQ ID NO 51
<211> LENGTH: 7
<212> TYPE: PRT
<213> ORGANISM: Homo sapiens

<400> SEQUENCE: 51

Ile His Tyr Gly Gly Asp Ile
1               5

<210> SEQ ID NO 52
<211> LENGTH: 21
<212> TYPE: PRT
<213> ORGANISM: Homo sapiens

<400> SEQUENCE: 52

Asn Val Ile Arg Val Phe Gly Val Ile Ala Leu Gly Glu Trp Phe His
1               5                   10                  15

Tyr Gly Met Asp Val
            20

<210> SEQ ID NO 53
<211> LENGTH: 108
<212> TYPE: PRT
<213> ORGANISM: Homo sapiens

<400> SEQUENCE: 53

Ser Ser Glu Leu Thr Gln Ala Pro Ser Val Thr Val Ser Pro Gly Asp
1               5                   10                  15

Thr Ala Arg Ile Ala Cys Ser Gly Pro Pro Leu Ala Thr Arg Tyr Cys
                20                  25                  30

Tyr Trp Tyr Arg Gln Lys Ser Gly Gln Ala Pro Val Leu Ile Ile Phe
            35                  40                  45

Arg Asp Arg Gln Phe Ser Ser Gly Val Ser Gly Arg Phe Ser Ser Ser
        50                  55                  60

Gln Ser Gly Ser Thr Val Thr Leu Thr Ile Arg Asp Val Arg Val Glu
65                  70                  75                  80

Asp Glu Ala Asp Tyr Tyr Cys Gln Ser Ser Asp Thr Ser Asp Ser Tyr
                85                  90                  95

Lys Met Phe Gly Gly Gly Thr Lys Leu Thr Val Leu
            100                 105

<210> SEQ ID NO 54
<211> LENGTH: 6
<212> TYPE: PRT
<213> ORGANISM: Homo sapiens

<400> SEQUENCE: 54

Pro Leu Ala Thr Arg Tyr
1               5

<210> SEQ ID NO 55
<211> LENGTH: 3
<212> TYPE: PRT
<213> ORGANISM: Homo sapiens

<400> SEQUENCE: 55
```

Arg Asp Arg
1

<210> SEQ ID NO 56
<211> LENGTH: 11
<212> TYPE: PRT
<213> ORGANISM: Homo sapiens

<400> SEQUENCE: 56

Gln Ser Ser Asp Thr Ser Asp Ser Tyr Lys Met
1               5                   10

<210> SEQ ID NO 57
<211> LENGTH: 130
<212> TYPE: PRT
<213> ORGANISM: Homo sapiens

<400> SEQUENCE: 57

Gln Val Gln Leu Arg Glu Ser Gly Pro Gly Leu Val Lys Pro Ser Glu
1               5                   10                  15

Thr Leu Ser Leu Ser Cys Asp Val Phe Gly Asp Ser Arg Pro Ser Asp
            20                  25                  30

His Ser Trp Thr Trp Val Arg Gln Pro Pro Gly Lys Ala Leu Glu Trp
        35                  40                  45

Ile Gly Asp Ile His Tyr Asn Gly Asp Lys Thr Tyr Asn Pro Ser Leu
    50                  55                  60

Arg Gly Arg Val Lys Ile Asp Val Asp Arg Ser Thr His Arg Phe Ser
65                  70                  75                  80

Leu Thr Leu Asn Ser Leu Thr Ala Ala Asp Thr Gly Met Tyr Phe Cys
                85                  90                  95

Ala Arg Asn Val Ile Arg Val Phe Gly Val Ile Ser Leu Gly Glu Trp
            100                 105                 110

Phe His Tyr Gly Met Asp Val Trp Gly Pro Gly Thr Ala Val Thr Val
        115                 120                 125

Ser Ser
    130

<210> SEQ ID NO 58
<211> LENGTH: 9
<212> TYPE: PRT
<213> ORGANISM: Homo sapiens

<400> SEQUENCE: 58

Gly Asp Ser Arg Pro Ser Asp His Ser
1               5

<210> SEQ ID NO 59
<211> LENGTH: 7
<212> TYPE: PRT
<213> ORGANISM: Homo sapiens

<400> SEQUENCE: 59

Ile His Tyr Asn Gly Asp Lys
1               5

<210> SEQ ID NO 60
<211> LENGTH: 21
<212> TYPE: PRT
<213> ORGANISM: Homo sapiens

<400> SEQUENCE: 60

```
Asn Val Ile Arg Val Phe Gly Val Ile Ser Leu Gly Glu Trp Phe His
1               5                   10                  15

Tyr Gly Met Asp Val
            20
```

<210> SEQ ID NO 61
<211> LENGTH: 108
<212> TYPE: PRT
<213> ORGANISM: Homo sapiens

<400> SEQUENCE: 61

```
Ser Ser Glu Leu Thr Gln Ala Pro Ser Val Ser Pro Gly Gln
1               5                   10                  15

Thr Ala Arg Ile Ala Cys Ser Gly Pro Pro Leu Ala Ser Arg Tyr Thr
                20                  25                  30

Tyr Trp Tyr Arg Gln Lys Pro Gly Gln Ala Pro Val Leu Ile Ile Phe
            35                  40                  45

Arg Asp Arg Gln Phe Pro Ser Gly Val Ser Gly Arg Phe Ser Ala Ser
    50                  55                  60

Lys Ser Gly Thr Thr Gly Thr Leu Thr Ile Arg Asp Val Gln Ala Glu
65                  70                  75                  80

Asp Glu Gly Asp Tyr Tyr Cys Gln Ser Ser Asp Thr Ser Asp Ser Tyr
                85                  90                  95

Lys Met Phe Gly Gly Thr Thr Leu Thr Val Leu
            100                 105
```

<210> SEQ ID NO 62
<211> LENGTH: 6
<212> TYPE: PRT
<213> ORGANISM: Homo sapiens

<400> SEQUENCE: 62

```
Pro Leu Ala Ser Arg Tyr
1               5
```

<210> SEQ ID NO 63
<211> LENGTH: 3
<212> TYPE: PRT
<213> ORGANISM: Homo sapiens

<400> SEQUENCE: 63

```
Arg Asp Arg
1
```

<210> SEQ ID NO 64
<211> LENGTH: 11
<212> TYPE: PRT
<213> ORGANISM: Homo sapiens

<400> SEQUENCE: 64

```
Gln Ser Ser Asp Thr Ser Asp Ser Tyr Lys Met
1               5                   10
```

<210> SEQ ID NO 65
<211> LENGTH: 130
<212> TYPE: PRT
<213> ORGANISM: Homo sapiens

<400> SEQUENCE: 65

```
Gln Val Gln Leu Arg Glu Ser Gly Pro Gly Leu Val Lys Pro Ser Gly
1               5                   10                  15
```

```
Asn Met Ala Leu Thr Cys Thr Ile Ser Gly Asp Ser Arg Pro Ser Asp
            20                  25                  30

His Ser Trp Thr Trp Val Arg Gln Ser Pro Gly Lys Ala Leu Glu Trp
        35                  40                  45

Ile Gly Asp Ile His Tyr Gly Asp Ile Thr Tyr Asn Pro Ser Leu
50                  55                  60

Arg Ser Arg Val Lys Leu Glu Val Asp Thr Ser Ser Asn Arg Phe Phe
65                  70                  75                  80

Leu Lys Met Thr Ser Leu Thr Val Ala Asp Thr Gly Ile Tyr Phe Cys
                85                  90                  95

Ala Arg Asn Val Ile Arg Val Phe Gly Val Ile Ala Leu Gly Glu Trp
                100                 105                 110

Phe His Tyr Gly Met Asp Val Trp Gly Gln Gly Thr Ala Ile Thr Val
            115                 120                 125

Ser Pro
    130

<210> SEQ ID NO 66
<211> LENGTH: 9
<212> TYPE: PRT
<213> ORGANISM: Homo sapiens

<400> SEQUENCE: 66

Gly Asp Ser Arg Pro Ser Asp His Ser
1               5

<210> SEQ ID NO 67
<211> LENGTH: 7
<212> TYPE: PRT
<213> ORGANISM: Homo sapiens

<400> SEQUENCE: 67

Ile His Tyr Gly Gly Asp Ile
1               5

<210> SEQ ID NO 68
<211> LENGTH: 21
<212> TYPE: PRT
<213> ORGANISM: Homo sapiens

<400> SEQUENCE: 68

Asn Val Ile Arg Val Phe Gly Val Ile Ala Leu Gly Glu Trp Phe His
1               5                   10                  15

Tyr Gly Met Asp Val
            20

<210> SEQ ID NO 69
<211> LENGTH: 108
<212> TYPE: PRT
<213> ORGANISM: Homo sapiens

<400> SEQUENCE: 69

Ser Ser Glu Leu Thr Gln Ala Pro Ser Val Thr Leu Ser Pro Gly Glu
1               5                   10                  15

Thr Ala Arg Ile Ala Cys Ser Gly Pro Pro Leu Ala Ser Arg Tyr Cys
            20                  25                  30

Tyr Trp Tyr Arg Gln Lys Pro Gly Gln Ala Pro Val Leu Ile Ile Phe
        35                  40                  45

Arg Asp Arg Gln Phe Ser Ser Gly Ile Ser Gly Arg Phe Ser Ser Ser
```

```
            50                  55                  60
Gln Ser Gly Thr Thr Val Thr Leu Thr Ile Arg Asp Val Arg Val Glu
 65                  70                  75                  80

Asp Glu Ala Asp Tyr Tyr Cys Gln Ser Ser Asp Asn Ser Asp Ser Phe
                 85                  90                  95

Lys Met Phe Gly Gly Gly Thr Lys Leu Thr Val Leu
            100                 105
```

<210> SEQ ID NO 70
<211> LENGTH: 6
<212> TYPE: PRT
<213> ORGANISM: Homo sapiens

<400> SEQUENCE: 70

```
Pro Leu Ala Ser Arg Tyr
 1               5
```

<210> SEQ ID NO 71
<211> LENGTH: 3
<212> TYPE: PRT
<213> ORGANISM: Homo sapiens

<400> SEQUENCE: 71

```
Arg Asp Arg
 1
```

<210> SEQ ID NO 72
<211> LENGTH: 11
<212> TYPE: PRT
<213> ORGANISM: Homo sapiens

<400> SEQUENCE: 72

```
Gln Ser Ser Asp Asn Ser Asp Ser Phe Lys Met
 1               5                  10
```

<210> SEQ ID NO 73
<211> LENGTH: 133
<212> TYPE: PRT
<213> ORGANISM: Homo sapiens

<400> SEQUENCE: 73

```
Ala Glu Gln Leu Val Glu Ser Gly Gly Leu Val Pro Pro Gly Arg
 1               5                  10                  15

Ser Leu Arg Leu Ser Cys Ser Ala Ser Gly Phe Tyr Phe Pro Asp Tyr
                 20                  25                  30

Ala Met Ala Trp Val Arg Gln Ala Pro Gly Gln Gly Leu Gln Trp Val
             35                  40                  45

Gly Phe Met Arg Gly Trp Ala Tyr Gly Gly Ser Ala Gln Phe Ala Ala
         50                  55                  60

Phe Ala Val Gly Lys Phe Ala Ile Ser Arg Asp Asp Gly Arg Asn Val
 65                  70                  75                  80

Val Tyr Leu Asp Val Lys Asn Pro Thr Phe Glu Asp Thr Gly Val Tyr
                 85                  90                  95

Phe Cys Ala Arg Glu Gln Arg Asn Lys Asp Tyr Arg Tyr Gly Gln Glu
            100                 105                 110

Gly Phe Gly Tyr Ser Tyr Gly Met Asp Val Trp Gly Arg Gly Thr Thr
            115                 120                 125

Val Val Val Ser Thr
        130
```

<210> SEQ ID NO 74
<211> LENGTH: 8
<212> TYPE: PRT
<213> ORGANISM: Homo sapiens

<400> SEQUENCE: 74

Gly Phe Tyr Phe Pro Asp Tyr Ala
1               5

<210> SEQ ID NO 75
<211> LENGTH: 10
<212> TYPE: PRT
<213> ORGANISM: Homo sapiens

<400> SEQUENCE: 75

Met Arg Gly Trp Ala Tyr Gly Gly Ser Ala
1               5                   10

<210> SEQ ID NO 76
<211> LENGTH: 22
<212> TYPE: PRT
<213> ORGANISM: Homo sapiens

<400> SEQUENCE: 76

Glu Gln Arg Asn Lys Asp Tyr Arg Tyr Gly Gln Glu Gly Phe Gly Tyr
1               5                   10                  15

Ser Tyr Gly Met Asp Val
            20

<210> SEQ ID NO 77
<211> LENGTH: 107
<212> TYPE: PRT
<213> ORGANISM: Homo sapiens

<400> SEQUENCE: 77

Asp Ile His Met Thr Gln Ser Pro Val Ser Leu Ser Ala Ser Val Gly
1               5                   10                  15

Asp Arg Val Thr Ile Thr Cys Arg Ala Ser His Phe Ile Ala Asn Tyr
            20                  25                  30

Val Asn Trp Tyr Gln Gln Lys Pro Gly Lys Ala Pro Thr Leu Leu Ile
        35                  40                  45

Phe Glu Ser Ser Thr Leu Gln Arg Gly Val Pro Ser Arg Phe Ser Ala
    50                  55                  60

Tyr Gly Asp Gly Thr Glu Phe Thr Leu Ser Ile Asn Thr Leu Gln Pro
65                  70                  75                  80

Glu Asp Phe Ala Ser Tyr Ile Cys Gln Gln Ser His Ser Pro Pro Val
                85                  90                  95

Thr Phe Gly Ala Gly Thr Arg Val Asp Gln Lys
            100                 105

<210> SEQ ID NO 78
<211> LENGTH: 6
<212> TYPE: PRT
<213> ORGANISM: Homo sapiens

<400> SEQUENCE: 78

His Phe Ile Ala Asn Tyr
1               5

<210> SEQ ID NO 79
<211> LENGTH: 3

```
<212> TYPE: PRT
<213> ORGANISM: Homo sapiens

<400> SEQUENCE: 79

Glu Ser Ser
1

<210> SEQ ID NO 80
<211> LENGTH: 9
<212> TYPE: PRT
<213> ORGANISM: Homo sapiens

<400> SEQUENCE: 80

Gln Gln Ser His Ser Pro Pro Val Thr
1               5

<210> SEQ ID NO 81
<211> LENGTH: 133
<212> TYPE: PRT
<213> ORGANISM: Homo sapiens

<400> SEQUENCE: 81

Glu Glu Arg Leu Val Glu Ser Gly Gly Gly Leu Val Pro Pro Gly Arg
1               5                   10                  15

Ser Leu Arg Leu Ser Cys Ser Ala Phe Asp Phe Tyr Phe Pro Asp Tyr
            20                  25                  30

Ala Met Ala Trp Val Arg Gln Ala Pro Gly Lys Gly Leu Glu Trp Ile
        35                  40                  45

Gly Phe Ile Arg Gly Trp Ala Tyr Gly Gln Ala Ala Gln Tyr Gly Lys
    50                  55                  60

Ser Ala Ser Gly Arg Met Thr Ile Ser Arg Asp Asp Ser Arg Arg Val
65                  70                  75                  80

Val Tyr Leu Asp Ile Lys Ser Pro Ile Glu Glu Asp Thr Gly Ala Tyr
                85                  90                  95

Phe Cys Ala Arg Glu Gln Arg Gly Gly Asp Gly Arg Tyr Ser Gly Asp
            100                 105                 110

Gly Phe Gly Tyr Pro Tyr Gly Met Asp Val Trp Gly Arg Gly Thr Met
        115                 120                 125

Val Thr Val Ser Ala
    130

<210> SEQ ID NO 82
<211> LENGTH: 8
<212> TYPE: PRT
<213> ORGANISM: Homo sapiens

<400> SEQUENCE: 82

Asp Phe Tyr Phe Pro Asp Tyr Ala
1               5

<210> SEQ ID NO 83
<211> LENGTH: 10
<212> TYPE: PRT
<213> ORGANISM: Homo sapiens

<400> SEQUENCE: 83

Ile Arg Gly Trp Ala Tyr Gly Gln Ala Ala
1               5                   10

<210> SEQ ID NO 84
<211> LENGTH: 22
```

```
<212> TYPE: PRT
<213> ORGANISM: Homo sapiens

<400> SEQUENCE: 84

Glu Gln Arg Gly Gly Asp Gly Arg Tyr Ser Gly Asp Gly Phe Gly Tyr
1               5                   10                  15

Pro Tyr Gly Met Asp Val
            20

<210> SEQ ID NO 85
<211> LENGTH: 107
<212> TYPE: PRT
<213> ORGANISM: Homo sapiens

<400> SEQUENCE: 85

Asp Ile Leu Met Thr Gln Ser Pro Val Ser Leu Ser Ala Ser Ile Gly
1               5                   10                  15

Glu Arg Ile Thr Ile Thr Cys Arg Ala Ser His Phe Ile Ala Asn Tyr
            20                  25                  30

Val Asn Trp Tyr Gln Gln Arg Pro Gly Lys Ala Pro Lys Leu Leu Ile
        35                  40                  45

Phe Gln Ser Trp Thr Leu Asn Arg Gly Ile Pro Ser Arg Phe Ser Gly
    50                  55                  60

Tyr Gly Asp Gly Thr Glu Phe Thr Leu Ser Ile Ser Ala Leu Gln Ser
65                  70                  75                  80

Glu Asp Phe Gly Thr Tyr Ile Cys Gln Gln Ser His Ser Pro Pro Leu
                85                  90                  95

Ser Phe Gly Gly Gly Thr Arg Val Asp Gln Thr
            100                 105

<210> SEQ ID NO 86
<211> LENGTH: 6
<212> TYPE: PRT
<213> ORGANISM: Homo sapiens

<400> SEQUENCE: 86

His Phe Ile Ala Asn Tyr
1               5

<210> SEQ ID NO 87
<211> LENGTH: 3
<212> TYPE: PRT
<213> ORGANISM: Homo sapiens

<400> SEQUENCE: 87

Gln Ser Trp
1

<210> SEQ ID NO 88
<211> LENGTH: 9
<212> TYPE: PRT
<213> ORGANISM: Homo sapiens

<400> SEQUENCE: 88

Gln Gln Ser His Ser Pro Pro Leu Ser
1               5

<210> SEQ ID NO 89
<211> LENGTH: 133
<212> TYPE: PRT
<213> ORGANISM: Homo sapiens
```

<400> SEQUENCE: 89

Glu Glu Arg Leu Val Glu Ser Gly Gly Gly Leu Val Pro Pro Gly Arg
1               5                   10                  15

Ser Leu Arg Leu Ser Cys Ser Ala Phe Asp Phe Tyr Phe Pro Asp Tyr
            20                  25                  30

Ala Met Ala Trp Val Arg Gln Ala Pro Gly Arg Ala Leu Glu Trp Ile
        35                  40                  45

Gly Phe Ile Arg Gly Trp Ala Tyr Gly Gln Ser Ala Gln Tyr Gly Lys
    50                  55                  60

Ser Ala Ser Gly Arg Met Thr Ile Ser Arg Asp Asp Ser Arg Arg Val
65                  70                  75                  80

Val Tyr Leu Asp Ile Lys Ser Pro Thr His Glu Asp Thr Gly Val Tyr
                85                  90                  95

Phe Cys Ala Arg Glu Gln Arg Gly Ala Asn Gly Arg Tyr Gly Gly Asp
            100                 105                 110

Gly Phe Gly Tyr Ser Tyr Gly Met Asp Val Trp Gly Arg Gly Thr Met
        115                 120                 125

Val Ser Val Ser Ala
    130

<210> SEQ ID NO 90
<211> LENGTH: 8
<212> TYPE: PRT
<213> ORGANISM: Homo sapiens

<400> SEQUENCE: 90

Asp Phe Tyr Phe Pro Asp Tyr Ala
1               5

<210> SEQ ID NO 91
<211> LENGTH: 10
<212> TYPE: PRT
<213> ORGANISM: Homo sapiens

<400> SEQUENCE: 91

Ile Arg Gly Trp Ala Tyr Gly Gln Ser Ala
1               5                   10

<210> SEQ ID NO 92
<211> LENGTH: 22
<212> TYPE: PRT
<213> ORGANISM: Homo sapiens

<400> SEQUENCE: 92

Glu Gln Arg Gly Ala Asn Gly Arg Tyr Gly Gly Asp Gly Phe Gly Tyr
1               5                   10                  15

Ser Tyr Gly Met Asp Val
            20

<210> SEQ ID NO 93
<211> LENGTH: 107
<212> TYPE: PRT
<213> ORGANISM: Homo sapiens

<400> SEQUENCE: 93

Asp Ile Gln Met Thr Gln Ser Pro Phe Thr Leu Ser Ala Ser Val Gly
1               5                   10                  15

Glu Arg Val Thr Ile Thr Cys Arg Ala Ser His Phe Ile Ala Asn Tyr
            20                  25                  30

-continued

Val Asn Trp Tyr Gln Gln Arg Pro Gly Arg Ala Pro Lys Leu Leu Ile
            35                  40                  45

Phe Glu Ser Ser Thr Leu Asn Arg Gly Val Pro Ser Arg Phe Ser Gly
 50                  55                  60

Ser Gly Asp Gly Thr Glu Phe Thr Leu Ser Ile Ser Ala Leu Gln Ser
 65                  70                  75                  80

Glu Asp Phe Ala Thr Tyr Ile Cys Gln Gln Ser His Ser Pro Pro Val
                 85                  90                  95

Ser Phe Gly Gly Gly Thr Arg Val Asp Gln Thr
            100                 105

<210> SEQ ID NO 94
<211> LENGTH: 6
<212> TYPE: PRT
<213> ORGANISM: Homo sapiens

<400> SEQUENCE: 94

His Phe Ile Ala Asn Tyr
1               5

<210> SEQ ID NO 95
<211> LENGTH: 3
<212> TYPE: PRT
<213> ORGANISM: Homo sapiens

<400> SEQUENCE: 95

Glu Ser Ser
1

<210> SEQ ID NO 96
<211> LENGTH: 9
<212> TYPE: PRT
<213> ORGANISM: Homo sapiens

<400> SEQUENCE: 96

Gln Gln Ser His Ser Pro Pro Val Ser
1               5

<210> SEQ ID NO 97
<211> LENGTH: 25
<212> TYPE: DNA
<213> ORGANISM: Artificial
<220> FEATURE:
<223> OTHER INFORMATION: primer

<400> SEQUENCE: 97
tagagccctg gaagcatcca ggaag                                       25

<210> SEQ ID NO 98
<211> LENGTH: 24
<212> TYPE: DNA
<213> ORGANISM: Artificial
<220> FEATURE:
<223> OTHER INFORMATION: primer

<400> SEQUENCE: 98
ttgctacttg tgattgctcc atgt                                        24

<210> SEQ ID NO 99
<211> LENGTH: 27
<212> TYPE: DNA
<213> ORGANISM: Artificial
<220> FEATURE:
<223> OTHER INFORMATION: primer

<400> SEQUENCE: 99
ttaggcatct cctatggcag gaagaag                                      27

<210> SEQ ID NO 100
<211> LENGTH: 23
<212> TYPE: DNA
<213> ORGANISM: Artificial
<220> FEATURE:
<223> OTHER INFORMATION: primer

<400> SEQUENCE: 100
gtctcgagat actgctccca ccc                                          23

<210> SEQ ID NO 101
<211> LENGTH: 29
<212> TYPE: DNA
<213> ORGANISM: Artificial
<220> FEATURE:
<223> OTHER INFORMATION: primer

<400> SEQUENCE: 101
agtaatcaat tacggggtca ttagttcat                                    29

<210> SEQ ID NO 102
<211> LENGTH: 45
<212> TYPE: DNA
<213> ORGANISM: Artificial
<220> FEATURE:
<223> OTHER INFORMATION: primer

<400> SEQUENCE: 102
cataggagat gcctaagccg gtggagctct gcttatatag acctc                  45

<210> SEQ ID NO 103
<211> LENGTH: 33
<212> TYPE: DNA
<213> ORGANISM: Artificial
<220> FEATURE:
<223> OTHER INFORMATION: primer

<400> SEQUENCE: 103
caccggctta ggcatctcct atggcaggaa gaa                               33

<210> SEQ ID NO 104
<211> LENGTH: 24
<212> TYPE: DNA
<213> ORGANISM: Artificial
<220> FEATURE:
<223> OTHER INFORMATION: primer

<400> SEQUENCE: 104
actttttgac cacttgccac ccat                                         24

<210> SEQ ID NO 105
<211> LENGTH: 19
<212> TYPE: PRT
<213> ORGANISM: Homo sapiens

<400> SEQUENCE: 105

Asp Asn Phe Gly Thr Arg Pro Val Pro Gly Arg Gly Tyr Tyr Tyr Gly
 1               5                  10                  15
Met Asp Val

-continued

```
<210> SEQ ID NO 106
<211> LENGTH: 19
<212> TYPE: PRT
<213> ORGANISM: Homo sapiens

<400> SEQUENCE: 106

Asp Asn Arg Gly Asp Arg Asn Val Pro Gly Arg Gly Tyr Tyr Tyr Gly
1               5                   10                  15

Met Asp Val

<210> SEQ ID NO 107
<211> LENGTH: 19
<212> TYPE: PRT
<213> ORGANISM: Homo sapiens

<400> SEQUENCE: 107

Asp Asn Phe Gly Thr Arg Pro Val Pro Gly Arg Gly Tyr Tyr Tyr Gly
1               5                   10                  15

Met Asp Val

<210> SEQ ID NO 108
<211> LENGTH: 16
<212> TYPE: PRT
<213> ORGANISM: Homo sapiens

<400> SEQUENCE: 108

Asp Asn Phe Gly Glu Ser His Lys Gly Tyr Thr Tyr Gly Met Asp Ala
1               5                   10                  15

<210> SEQ ID NO 109
<211> LENGTH: 16
<212> TYPE: PRT
<213> ORGANISM: Homo sapiens

<400> SEQUENCE: 109

Asp Asn Phe Gly Glu Ser His Lys Gly Tyr Thr Tyr Gly Met Asp Ala
1               5                   10                  15

<210> SEQ ID NO 110
<211> LENGTH: 16
<212> TYPE: PRT
<213> ORGANISM: Homo sapiens

<400> SEQUENCE: 110

Asp Asn Phe Gly Glu Ser His Lys Gly Tyr Thr Tyr Gly Met Asp Ala
1               5                   10                  15

<210> SEQ ID NO 111
<211> LENGTH: 8
<212> TYPE: PRT
<213> ORGANISM: Homo sapiens

<400> SEQUENCE: 111

Gly Ala Ser Ile Ser Asp Ser Tyr
1               5

<210> SEQ ID NO 112
<211> LENGTH: 7
<212> TYPE: PRT
<213> ORGANISM: Homo sapiens

<400> SEQUENCE: 112

Val His Lys Ser Gly Asp Thr
1               5
```

<210> SEQ ID NO 113
<211> LENGTH: 24
<212> TYPE: PRT
<213> ORGANISM: Homo sapiens

<400> SEQUENCE: 113

Thr Leu His Gly Arg Arg Ile Tyr Gly Ile Val Ala Phe Asn Glu Trp
1               5                   10                  15

Phe Thr Tyr Phe Tyr Met Asp Val
            20

<210> SEQ ID NO 114
<211> LENGTH: 6
<212> TYPE: PRT
<213> ORGANISM: Homo sapiens

<400> SEQUENCE: 114

Ser Leu Gly Ser Arg Ala
1               5

<210> SEQ ID NO 115
<211> LENGTH: 3
<212> TYPE: PRT
<213> ORGANISM: Homo sapiens

<400> SEQUENCE: 115

Asn Asn Gln
1

<210> SEQ ID NO 116
<211> LENGTH: 12
<212> TYPE: PRT
<213> ORGANISM: Homo sapiens

<400> SEQUENCE: 116

His Ile Trp Asp Ser Arg Val Pro Thr Lys Trp Val
1               5                   10

<210> SEQ ID NO 117
<211> LENGTH: 8
<212> TYPE: PRT
<213> ORGANISM: Homo sapiens

<400> SEQUENCE: 117

Gly Asp Ser Met Asn Asn Tyr Tyr
1               5

<210> SEQ ID NO 118
<211> LENGTH: 7
<212> TYPE: PRT
<213> ORGANISM: Homo sapiens

<400> SEQUENCE: 118

Ile Ser Asp Arg Glu Ser Ala
1               5

<210> SEQ ID NO 119
<211> LENGTH: 24
<212> TYPE: PRT
<213> ORGANISM: Homo sapiens

<400> SEQUENCE: 119

Ala Arg Arg Gly Gln Arg Ile Tyr Gly Val Val Ser Phe Gly Glu Phe

```
                1               5                  10                 15
Phe Tyr Tyr Tyr Ser Met Asp Val
            20

<210> SEQ ID NO 121
<211> LENGTH: 6
<212> TYPE: PRT
<213> ORGANISM: Homo sapiens

<400> SEQUENCE: 120

Ala Leu Gly Ser Arg Ala
1               5

<210> SEQ ID NO 121
<211> LENGTH: 3
<212> TYPE: PRT
<213> ORGANISM: Homo sapiens

<400> SEQUENCE: 121

Asn Asn Gly
1

<210> SEQ ID NO 122
<211> LENGTH: 12
<212> TYPE: PRT
<213> ORGANISM: Homo sapiens

<400> SEQUENCE: 122

His Met Trp Asp Ser Arg Ser Gly Phe Ser Trp Ser
1               5                   10

<210> SEQ ID NO 123
<211> LENGTH: 132
<212> TYPE: PRT
<213> ORGANISM: Artificial
<220> FEATURE:
<223> OTHER INFORMATION: Synthetic

<400> SEQUENCE: 123

Gln Val Gln Leu Gln Glu Ser Gly Pro Gly Leu Val Lys Pro Ser Glu
1               5                   10                  15

Thr Leu Ser Val Thr Cys Ser Val Ser Gly Asp Ser Met Asn Asn Tyr
            20                  25                  30

Tyr Trp Thr Trp Ile Arg Gln Ser Pro Gly Lys Gly Leu Glu Trp Ile
        35                  40                  45

Gly Tyr Ile Ser Asp Arg Glu Ser Ala Thr Tyr Asn Pro Ser Leu Asn
    50                  55                  60

Ser Arg Val Val Ile Ser Arg Asp Thr Ser Lys Asn Gln Leu Ser Leu
65                  70                  75                  80

Lys Leu Asn Ser Val Thr Pro Ala Asp Thr Ala Val Tyr Tyr Cys Ala
                85                  90                  95

Thr Ala Arg Arg Gly Gln Arg Ile Tyr Gly Val Val Ser Phe Gly Glu
            100                 105                 110

Phe Phe Tyr Tyr Tyr Ser Met Asp Val Trp Gly Lys Gly Thr Thr Val
        115                 120                 125

Thr Val Ser Ser
        130

<210> SEQ ID NO 124
<211> LENGTH: 108
<212> TYPE: PRT
```

```
<213> ORGANISM: Artificial
<220> FEATURE:
<223> OTHER INFORMATION: Synthetic

<400> SEQUENCE: 124

Ser Tyr Val Arg Pro Leu Ser Val Ala Leu Gly Glu Thr Ala Arg Ile
1               5                   10                  15

Ser Cys Gly Arg Gln Ala Leu Gly Ser Arg Ala Val Gln Trp Tyr Gln
            20                  25                  30

His Arg Pro Gly Gln Ala Pro Ile Leu Leu Ile Tyr Asn Asn Gln Asp
        35                  40                  45

Arg Pro Ser Gly Ile Pro Glu Arg Phe Ser Gly Thr Pro Asp Ile Asn
    50                  55                  60

Phe Gly Thr Arg Ala Thr Leu Thr Ile Ser Gly Val Glu Ala Gly Asp
65                  70                  75                  80

Glu Ala Asp Tyr Tyr Cys His Met Trp Asp Ser Arg Ser Gly Phe Ser
                85                  90                  95

Trp Ser Phe Gly Gly Ala Thr Arg Leu Thr Val Leu
            100                 105

<210> SEQ ID NO 125
<211> LENGTH: 132
<212> TYPE: PRT
<213> ORGANISM: Artificial
<220> FEATURE:
<223> OTHER INFORMATION: Synthetic

<400> SEQUENCE: 125

Gln Met Gln Leu Gln Glu Ser Gly Pro Gly Leu Val Lys Pro Ser Glu
1               5                   10                  15

Thr Leu Ser Leu Thr Cys Ser Val Ser Gly Ala Ser Ile Ser Asp Ser
            20                  25                  30

Tyr Trp Ser Trp Ile Arg Arg Ser Pro Gly Lys Gly Leu Glu Trp Ile
        35                  40                  45

Gly Tyr Val His Lys Ser Gly Asp Thr Asn Tyr Ser Pro Ser Leu Lys
    50                  55                  60

Ser Arg Val Asn Leu Ser Leu Asp Thr Ser Lys Asn Gln Val Ser Leu
65                  70                  75                  80

Ser Leu Val Ala Ala Thr Ala Ala Asp Ser Gly Lys Tyr Tyr Cys Ala
                85                  90                  95

Arg Thr Leu His Gly Arg Arg Ile Tyr Gly Ile Val Ala Phe Asn Glu
            100                 105                 110

Trp Phe Thr Tyr Phe Tyr Met Asp Val Trp Gly Asn Gly Thr Gln Val
        115                 120                 125

Thr Val Ser Ser
    130

<210> SEQ ID NO 126
<211> LENGTH: 105
<212> TYPE: PRT
<213> ORGANISM: Artificial
<220> FEATURE:
<223> OTHER INFORMATION: Synthetic

<400> SEQUENCE: 126

Ser Asp Ile Ser Val Ala Pro Gly Glu Thr Ala Arg Ile Ser Cys Gly
1               5                   10                  15

Glu Lys Ser Leu Gly Ser Arg Ala Val Gln Trp Tyr Gln His Arg Ala
            20                  25                  30
```

```
Gly Gln Ala Pro Ser Leu Ile Ile Tyr Asn Asn Gln Asp Arg Pro Ser
            35                  40                  45

Gly Ile Pro Glu Arg Phe Ser Gly Ser Pro Asp Ser Pro Phe Gly Thr
 50                  55                  60

Thr Ala Thr Leu Thr Ile Thr Ser Val Glu Ala Gly Asp Glu Ala Asp
 65                  70                  75                  80

Tyr Tyr Cys His Ile Trp Asp Ser Arg Val Pro Thr Lys Trp Val Phe
                 85                  90                  95

Gly Gly Gly Thr Thr Leu Thr Val Leu
                100                 105

<210> SEQ ID NO 127
<211> LENGTH: 130
<212> TYPE: PRT
<213> ORGANISM: Artificial
<220> FEATURE:
<223> OTHER INFORMATION: Synthetic

<400> SEQUENCE: 127

Gln Val Gln Leu Arg Glu Ser Gly Pro Gly Leu Val Lys Pro Ser Glu
1               5                   10                  15

Thr Leu Ser Leu Ser Cys Thr Val Ser Gln Asp Ser Arg Pro Ser Asp
            20                  25                  30

His Ser Trp Thr Trp Val Arg Gln Ser Pro Gly Lys Ala Leu Glu Trp
        35                  40                  45

Ile Gly Asp Ile His Tyr Asn Gly Ala Thr Thr Tyr Asn Pro Ser Leu
 50                  55                  60

Arg Ser Arg Val Arg Ile Glu Leu Asp Gln Ser Ile Pro Arg Phe Ser
65                  70                  75                  80

Leu Lys Met Thr Ser Met Thr Ala Ala Asp Thr Gly Met Tyr Tyr Cys
                85                  90                  95

Ala Arg Asn Ala Ile Arg Ile Tyr Gly Val Val Ala Leu Gly Glu Trp
            100                 105                 110

Phe His Tyr Gly Met Asp Val Trp Gly Gln Gly Thr Ala Val Thr Val
        115                 120                 125

Ser Ser
    130

<210> SEQ ID NO 128
<211> LENGTH: 109
<212> TYPE: PRT
<213> ORGANISM: Artificial
<220> FEATURE:
<223> OTHER INFORMATION: Synthetic

<400> SEQUENCE: 128

Trp Ala Ser Ser Glu Leu Thr Gln Pro Pro Ser Val Ser Val Ser Pro
1               5                   10                  15

Gly Gln Thr Ala Arg Ile Thr Cys Ser Gly Ala Pro Leu Thr Ser Arg
            20                  25                  30

Phe Thr Tyr Trp Tyr Arg Gln Lys Pro Gly Gln Ala Pro Val Leu Ile
        35                  40                  45

Ile Ser Arg Ser Ser Gln Arg Ser Ser Gly Trp Ser Gly Arg Phe Ser
 50                  55                  60

Ala Ser Trp Ser Gly Thr Thr Val Thr Leu Thr Ile Arg Gly Val Gln
65                  70                  75                  80

Ala Asp Asp Glu Ala Asp Tyr Tyr Cys Gln Ser Ser Asp Thr Ser Asp
```

```
                    85                  90                  95
Ser Tyr Lys Met Phe Gly Gly Gly Thr Lys Leu Thr Val
                100                 105
```

BROADLY NEUTRALIZING ANTI-HIV-1 ANTIBODIES AND METHODS OF USE THEREOF

STATEMENT REGARDING FEDERAL FUNDING

This invention was made with government support under grant number P01 AI100148 awarded by the National Institute of Health (NIH). The U.S. Government has certain rights in this invention.

REFERENCE TO A SEQUENCE LISTING

This application incorporates by reference the Sequence Listing submitted in Computer Readable Form, created on Sep. 23, 2021 and containing 49,152 bytes.

FIELD OF THE INVENTION

The field of the invention is to broadly neutralizing anti-HIV-1 antibodies (bNabs) and methods of use thereof.

BACKGROUND

Human immunodeficiency virus ("HIV") is a lentivirus (family retroviridae) that infects humans. If left untreated, over time HIV infection will result in acquired immunodeficiency syndrome (AIDS), a condition in which progressive failure of the immune system allows life-threatening opportunistic infections (e.g. toxoplasmosis) and cancers (e.g. Kaposi's sarcoma) to thrive, ultimately resulting in the death of the infected individual. Without treatment, the average survival time after initial infection is between 9 to 11 years total. HIV/AIDS represents a significant global health crisis, considered a pandemic by the CDC, with about 37 million people infected with HIV as of 2014, resulting in about 1.2 million deaths that year.

HIV has several subtypes characterized, including HIV-1 and HIV-2. HIV-1 is more virulent, more infective, and prevalent globally, whereas HIV-2 is less virulent, less infective, and is currently prevalent only in West Africa. HIV-1 represents the cause of the majority of HIV infections and thus represents a more clinically significant target. There are several subgroups within HIV-1, including group M, group N, group 0, and group P. Group M, standing for "major", represents approximately 90% of HIV infections, and is broken down into yet further subtypes, A-K, occasionally split into sub-subtypes (A1, A2, etc.). The remarkable diversity of HIV-1, brought about by a high mutation rate, contributes to the difficulty of effectively treating HIV. To combat this issue, researchers have attempted to develop what are known as broadly neutralizing antibodies ("bNAbs"), which are designated as such for their ability to neutralize multiple viral strains of HIV, e.g. multiple HIV-1 viral strains, such as those disclosed in US 2014/0328862, hereby incorporated by reference in its entirety. A fraction of HIV-1 infected individuals develops bNAbs which typically develop over a period of 1-3 years during which time there is co-evolution of circulating viral strains and antibodies. However, these bNabs typically fail to neutralize co-existing autologous viruses due to antibody-mediated selection against sensitive viral strains. Accordingly, there is an urgent need for novel, broadly neutralizing anti-HIV antibodies which exhibit a high level of potency against HIV-1 infection.

SUMMARY OF THE INVENTION

The present invention relates to a number of broadly neutralizing, potent anti-HIV-1 antibodies and the methods of use thereof. Accordingly, in some embodiments, the present invention comprises an anti-HIV-1 antibody. In some embodiments, the anti-HIV-1 antibody is a broadly neutralizing anti-HIV-1 antibody (bNab) or an antigen-binding portion thereof. In some embodiments, the anti-HIV-1 antibody comprises NC37 and antigen-binding portions thereof. In some embodiments, the anti-HIV-1 antibody comprises BG1 and antigen-binding portions thereof. In some embodiments, the anti-HIV-1 antibody comprises BG18 and antigen-binding portions thereof. In some embodiments, the invention comprises a variant of BG18 and antigen-binding portions thereof. In some embodiments, the variant of BG18 comprises one of 354BG8, 354BG18, 354BG42, 354BG33, 354BG129, 354BG188, 354BG411, and 354BG426, or antigen binding portions thereof. In some embodiments, the anti-HIV-1 antibody or antigen binding portion thereof comprises a monoclonal antibody (mAb). In some embodiments, the anti-HIV-1 antibody or antigen-binding portion thereof comprises a recombinant antibody. In some embodiments, the anti-HIV-1 antibody or antigen-binding portion thereof comprises a recombinantly produced antibody. In some embodiments, the anti-HIV-1 antibody or antigen-binding portion thereof comprises a human antibody. In some embodiments, the anti-HIV-1 antibody or antigen binding portion thereof comprises a bispecific antibody.

In some embodiments, the anti-HIV-1 antibody or antigen-binding portions thereof comprises a variable heavy chain region. In some embodiments, the variable heavy chain region comprises one of SEQ ID NOs: 1, 9, 17, 25, 33, 41, 49, 57, 65, 73, 81, and 89. In some embodiments, the variable heavy chain region has at least 75%, at least 80%, at least 85%, at least 90%, least 95%, at least 96%, at least 97%, at least 98%, or at least 99% homology with one of SEQ ID NOs: 1, 9, 17, 25, 33, 41, 49, 57, 65, 73, 81, and 89. In some embodiments, one or more of SEQ ID NOs: 1, 9, 17, 25, 33, 41, 49, 57, 65, 73, 81, and 89 has conservative substitutions.

In some embodiments, the anti-HIV-1 antibody or antigen-binding portions thereof comprises a variable light chain region. In some embodiments, the variable light chain region comprises one of SEQ ID NOs: 5, 13, 21, 29, 37, 45, 53, 61, 69, 77, 85, and 93. In some embodiments, the variable light chain region has at least 75%, at least 80%, at least 85%, at least 90%, least 95%, at least 96%, at least 97%, at least 98%, or at least 99% homology with one of SEQ ID NOs: 5, 13, 21, 29, 37, 45, 53, 61, 69, 77, 85, and 93. In some embodiments, one or more of SEQ ID NOs: 5, 13, 21, 29, 37, 45, 53, 61, 69, 77, 85, and 93 has conservative substitutions.

In some embodiments, the anti-HIV-1 antibody or antigen-binding portion thereof comprises at least one complementarity determining regions (CDRs) within the heavy variable chain region. In some embodiments, at least one CDR comprises one of SEQ ID NO: 2-4, 10-12, 18-20, 26-28, 34-36, 42-44, 50-52, 58-60, 66-68, 74-76, 82-84, and 90-92. In some embodiments, the at least one CDR has at least 75%, at least 80%, at least 85%, at least 90%, least 95%, at least 96%, at least 97%, at least 98%, or at least 99% homology with one of SEQ ID NO: 2-4, 10-12, 18-20, 26-28, 34-36, 42-44, 50-52, 58-60, 66-68, 74-76, 82-84, and 90-92. In some embodiments, one or more of SEQ ID NO:

2-4, 10-12, 18-20, 26-28, 34-36, 42-44, 50-52, 58-60, 66-68, 74-76, 82-84, and 90-92 has conservative substitutions.

In some embodiments, the anti-HIV-1 antibody or antigen-binding portion thereof comprises at least one complementarity determining regions (CDRs) within the light variable chain region. In some embodiments, at least one CDR comprises one of SEQ ID NO: 6-8, 14-16, 22-24, 30-32, 38-40, 46-48, 54-56, 62-64, 70-72, 78-80, 86-88, and 94-96. In some embodiments, the at least one CDR has at least 75%, at least 80%, at least 85%, at least 90%, least 95%, at least 96%, at least 97%, at least 98%, or at least 99% homology with one of SEQ ID NO: 6-8, 14-16, 22-24, 30-32, 38-40, 46-48, 54-56, 62-64, 70-72, 78-80, 86-88, and 94-96. In some embodiments, one or more of SEQ ID NO: 6-8, 14-16, 22-24, 30-32, 38-40, 46-48, 54-56, 62-64, 70-72, 78-80, 86-88, and 94-96 has conservative substitutions.

In some embodiments, the present invention is directed to kits comprising a first antibody. In some embodiments, the first antibody is an anti-HIV-1 antibody or antigen-binding portion thereof. In some embodiments, the anti-HIV-1 antibody or antigen-binding portion thereof comprises a broadly neutralizing anti-HIV-1 antibody (bNab). In some embodiments, the broadly neutralizing anti-HIV-1 antibody is any anti-HIV-1 antibody according to the present invention. In some embodiments, the anti-HIV-1 antibody specifically binds to HIV-1 or an antigenic fragment thereof. In some embodiments, the anti-HIV-1 antibody neutralizes HIV-1 upon binding. In some embodiments, the kits contain a second antibody. In some embodiments, the second antibody comprises an anti-HIV-1 antibody or antigen-binding portion thereof which specifically binds to HIV-1 or an antigenic fragment thereof. In other embodiments, the second antibody specifically binds to the first antibody or antigen-binding portion thereof. In some embodiments, the first antibody or antigen-binding portion thereof is bound to a substrate. In some embodiments, the second antibody or antigen-binding portion thereof is bound to a substrate. In some embodiments, the first antibody or antigen-binding portion thereof is detectably labeled. In some embodiments, the second antibody or antigen-binding portion thereof is detectably labeled. In some embodiments, at least one of the first antibody or antigen-binding portion thereof and the second antibody or antigen-binding portion thereof is detectably labeled. In some embodiments, the detectable label comprises a reporter molecule. In some embodiments, the reporter molecule comprises a fluorescent molecule. In some embodiments, the reporter comprises a radiolabel. In other embodiments, the detectable label comprises an enzyme. In some embodiments, the kits include a substrate for the enzyme. In some embodiments, adding a substrate to the enzyme leads to the production of a detectable signal. In some embodiments, the detectable signal comprises a colored soluble product. In some embodiments, the radiolabel comprises 1-125. In some embodiments, the enzyme comprises horseradish peroxidase. In some embodiments, the substrate for the enzyme comprises TMB. In some embodiments, the kits are capable of detecting HIV-1 or antigenc fragments thereof in a sample. In some embodiments, the kits are capable of quantifying the amount of HIV-1 or antigenic fragments thereof present in a sample.

In some embodiments, the kits further comprise an HIV agent. In some embodiments, the HIV agent is selected from the group consisting of non-nucleoside reverse transcriptase inhibitors (NNRTIs), nucleoside reverse transcriptase inhibitors (NRTIs), protease inhibitors (PIs), fusion inhibitors, CCR5 antagonists/entry inhibitors, integrase strand transfer inhibitors (INSTIs), and combinations thereof. In some embodiments, the HIV agent is in a unit dosage form. In some embodiments, the anti-HIV-1 antibody or antigen-binding portion thereof is in a unit dosage form. In some embodiments, the unit dosage form is a unit dosage injectable form. In some embodiments, the HIV agent is stored in the same container as the anti-HIV-1 antibody or antigen-binding portion thereof. In some embodiments, the HIV agent is stored in a separate contained. In some embodiments, the kits further comprise one or more additional anti-HIV-1 antibodies or antigen-binding portions thereof. In some embodiments, the one or more additional anti-HIV-1 antibodies or antigen-binding portions thereof comprise any anti-HIV-1 antibodies of the present invention. In some embodiments, the one or more additional anti-HIV-1 antibodies or antigen-binding portions thereof are selected from the group consisting of NC37, NC133, NC102, AC40, AC41, AC72, and combinations thereof. In some embodiments, the kits comprise instructions for use. In some embodiments, the kits comprise one or more pharmaceutically acceptable carriers or preservatives.

In some embodiments, the present invention is directed to a method of detecting HIV-1 or an antigenic fragment thereof present in a sample. In some embodiments, the method comprises obtaining a sample containing HIV-1 or an antigenic fragment thereof. In some embodiments, the method comprises contacting the sample with an anti-HIV-1 antibody or antigen-binding portion thereof. In some embodiments, the methoc comprises detecting the presence of specific binding of the anti-HIV-1 antibody or antigen-binding portion thereof to HIV or the antigenic fragment thereof. In some embodiments, the method includes quantifying the amount of HIV-1 or antigenic fragments thereof present in the sample. In some embodiments, the sample is a biological sample. In some embodiments, the anti-HIV-1 antibody or antigen-binding portion thereof is an anti-HIV-1 antibody or antigen binding portion thereof according to any aspect of this present invention. In some embodiments, the anti-HIV-1 antibody or antigen-binding portion thereof comprises a monoclonal antibody. In some embodiments, the anti-HIV-1 antibody or antigen-binding portion thereof comprises a recombinant antibody. In some embodiments, the anti-HIV-1 antibody or antigen-binding portion thereof is recombinantly produced. In some embodiments, the anti-HIV-1 antibody or antigen-binding portion thereof comprises a human antibody. In some embodiments, detecting the presence of specific binding is accomplished by an immunoassay. In some embodiments, detecting the presence of specific binding is accomplished by a competitive immunoassay.

In another embodiment, the present invention is directed to a method of diagnosing an individual as having an HIV-1 infection. In some embodiments, the method comprises identifying an individual having, or suspected of having, an HIV-1 infection. In some embodiments, the method comprises obtaining from the individual a sample containing HIV-1 or an antigenic fragment thereof. In some embodiments, the method comprises contacting the sample with an anti-HIV-1 antibody or antigen-binding portion thereof. In some embodiments, the anti-HIV-1 antibody or antigen-binding portion thereof is an anti-HIV-1 antibody or antigen-binding portion thereof according to any aspect of the present invention. In some embodiments, the method comprises detecting the presence of specific binding of the anti-HIV-1 antibody or antigen-binding portion thereof to HIV or the antigenic fragment thereof. In some embodiments, the method comprises diagnosing the individual as having an HIV-1 infection. In some embodiments, the individual is diagnosed as having AIDS. In some embodiments, the sample is a biological sample. In some embodiments, the anti-HIV-1 antibody or antigen-binding portion thereof comprises a monoclonal antibody. In some embodiments, the anti-HIV-1 antibody or antigen-binding portion thereof comprises a recombinant antibody. In some embodiments, the anti-HIV-1 antibody or antigen-binding portion thereof is recombinantly produced. In some embodiments, the anti-HIV-1 antibody or antigen binding portion thereof comprises a human antibody. In some embodiments, detecting the presence of specific binding is accomplished by an immunoassay. In some embodiments, detecting the presence of specific binding is accomplished by a competitive immunoassay.

In some embodiments, the present invention is directed to a method of treating an HIV-1 infection in an individual in need thereof. In some embodiments, the method of treating an HIV-1 infection includes administering to an individual having, or suspected of having, an HIV-1 infection at least one anti-HIV-1 antibody or antigen-binding portion thereof. In some embodiments, the at least one anti-HIV-1 antibody or antigen-binding portion thereof comprises a broadly neutralizing anti-HIV-1 antibody (bNab) or antigen-binding portion thereof. In some embodiments, the at least one anti-HIV-1 antibody or antigen binding portion thereof comprises any anti-HIV-1 antibody or antigen-binding portion thereof according to the present invention. In some embodiments, the method comprises the step of identifying an individual as having an HIV-1 infection prior to the administering step. In some embodiments, the anti-HIV-1 antibody or antigen-binding portion thereof comprises a monoclonal antibody. In some embodiments, the anti-HIV-1 antibody comprises a recombinant antibody. In some embodiments, the anti-HIV-1 antibody or antigen-binding portion thereof is recombinantly produced. In some embodiments, the anti-HIV-1 antibody or antigen-binding portion thereof comprises a human antibody. In some embodiments, the method further includes administration of at least one additional anti-HIV-1 antibody or antigen-binding portion thereof. In some embodiments, the at least one additional anti-HIV-1 antibody or antigen-binding portion thereof comprises a broadly neutralizing anti-HIV-1 antibody (bNab) or antigen-binding portion thereof. In some embodiments, the at least one anti-HIV-1 antibody or antigen binding portion thereof comprises any anti-HIV-1 antibody or antigen-binding portion thereof according to the present invention. In some embodiments, the additional anti-HIV-1 antibody or antigen-binding portion thereof comprises a monoclonal antibody. In some embodiments, the additional anti-HIV-1 antibody or antigen-binding portion thereof comprises a recombinant antibody. In some embodiments, the additional anti-HIV-1 antibody or antigen-binding portion thereof is recombinantly produced. In some embodiments, the method further includes administration of an HIV agent. In some embodiments, the HIV agent is selected from the group consisting of non-nucleoside reverse transcriptase inhibitors (NNRTIs), nucleoside reverse transcriptase inhibitors (NRTIs), protease inhibitors (PIs), fusion inhibitors, CCR5 antagonists/entry inhibitors, integrase strand transfer inhibitors (INSTIs), and combinations thereof. In some embodiments, the anti-HIV-1 antibody or antigen-binding portion thereof may be co-administered with the additional anti-HIV-1 antibody or antibodies or antigen-binding portion(s) thereof and/or HIV agent or HIV agents. In other embodiments, the anti-HIV antibody or antigen-binding portion thereof is administered prior to the additional anti-HIV-1 antibody or antibodies or antigen-binding portion(s) thereof and/or HIV agent or HIV agents. In yet other embodiments, the anti-HIV-1 antibody or antigen-binding portion thereof is administered after the additional anti-HIV-1 antibody or antibodies or antigen-binding portion(s) thereof and/or HIV agent or HIV agents. And in yet even other embodiments, the anti-HIV-1 antibody or antigen-binding portion thereof may be administered in between additional anti-HIV-1 antibodies or antigen-binding portion(s) thereof and/or HIV agent or HIV agents.

In another embodiment, the present invention is directed to a passive vaccine. In some embodiments, the vaccine comprises at least one anti-HIV-1 antibody or antigen-binding portion thereof. In some embodiments, the anti-HIV-1 antibody or antigen-binding portion thereof comprises a broadly neutralizing anti-HIV-1 antibody (bNab) or antigen-binding portion thereof. In some embodiments, the anti-HIV-1 antibody or antigen-binding portion thereof comprises any anti-HIV-1 antibody or antigen-binding portion thereof according to the present invention. In some embodiments, the anti-HIV-1 antibody or antigen-binding portion thereof comprises a monoclonal antibody. In some embodiments, the anti-HIV-1 antibody or antigen-binding portion thereof comprises a recombinant antibody. In some embodiments, the anti-HIV-1 antibody or antigen-binding portion thereof is recombinantly produced. In some embodiments, the passive vaccine further comprises an adjuvant. In some embodiments, the passive vaccine further comprises a pharmaceutically acceptable excipient, preservative, and/or carrier. In another embodiment, the present invention is directed to a method of preventing an HIV-1 infection in an individual in need thereof. In some embodiments, the method includes administering to an individual a passive vaccine composition according to any aspect of the present invention.

In some embodiments, the present invention is directed to a nucleic acid. In some embodiments, the nucleic acid comprises a nucleotide sequence encoding one or more heavy and/or light chains of the anti-HIV-1 antibodies of the present invention. In some embodiments, the nucleic acid comprises a nucleotide sequence encoding one or more of SEQ ID NOs: 1, 5, 9, 13, 17, 21, 25, 29, 33, 37, 41, 45, 49, 53, 57, 61, 65, 99, 73, 77, 81, 85, 89, and 93. In some embodiments, the nucleic acid has conservative substitutions. In some embodiments, the nucleic acid comprises a nucleotide sequence encoding one or more CDRs of the anti-HIV-1 antibodies of the present invention. In some embodiments, the nucleic acid comprises a nucleotide sequence encoding one or more of SEQ ID Nos: 2-4, 6-8, 10-12, 14-16, 18-20, 22-24, 26-28, 30-32, 34-36, 38-40, 42-44, 46-48, 50-52, 54-56, 58-60, 62-64, 66-68, 70-72, 74-76, 78-80, 82-84, 86-88, 90-92, and 94-96. In some embodiments, the nucleic acid has conservative substitutions.

In some embodiments, the present invention is directed to a vector or system of vectors containing one or more nucleic acid sequences encoding the heavy and/or light chains and/or
CDRs of one or more of the anti-HIV-1 antibodies or antigen-binding portions thereof of the present invention. In some embodiments, the vector or vector system comprises a nucleic acid sequence coding for a variable heavy chain region and a nucleic acid sequence coding for a variable light chain region. In some embodiments, a nucleic acid sequence coding for a heavy chain is on the same vector as a nucleic acid sequence coding for a light chain. In some embodiments, a nucleic acid sequence coding for a variable heavy chain region is on a different vector than a nucleic acid sequence coding for a variable light chain region. In some embodiments, the vector or system of vectors is a plasmid or plasmids. In some embodiments, the vector or a system of vectors is a phage vector or vectors. In some embodiments, the phage vector is a γ phage. In some embodiments, the vector or vectors is a cosmid or cosmids. In some embodiments, the vector or system of vectors is a recombinant chromosome or recombinant chromosomes. In some embodiments, the vector system is a combination of different vectors. In some embodiments, expression of the different nucleic acid sequences may be concomitant. In other embodiments, expression of the different nucleic acid sequences may be separately inducible. In another embodiment, the present invention is directed to a vector or system of vectors containing one or more nucleic acid sequences encoding one or more complementarity determining regions (CDRs) of one or more heavy and/or light chains of one or more of the anti-HIV-1 antibodies of the present invention.

BRIEF DESCRIPTION OF THE FIGURES

FIG. 1 A: Viral load values as measured in years 2002-2015. The time points when neutralizing antibodies were isolated are indicated on the graph. The time point where plasma was collected are marked with downward-pointing arrows. FIG. 1B: Heat map showing $IC_{50}$ values in TZM-bl assay of purified serum IgG from 4 time points (indicated by arrows in (1A)) tested against a panel of HIV-1 strains. All neutralization assays were performed in duplicates. FIG. 1C: Upper panels: CD19 pre-enriched IgG+ memory B cells were stained with CD19 and with three non-native HIV-1 baits: 2CC core, $gp140_{YU2}$ fold-on trimer and $gp140_{92UG37.8}+gp140_{CZA79012}$ (gp140 A+C) fold-on trimmers, and one native bait BG505.SOSIP-AviB. The populations in the squared insert represents cells that were single cell sorted and the numbers indicate the percent of cells that were CD19+/bait+ out of the total IgG+ cells. Lower panels: Pie charts represent the total Ig sequences that were amplified from the single sorted cells from the corresponding FACS plot shown on top. The number in the middle of the pies represents the total number of antibodies. Empty slices represent sequences that appeared only once and did not have any clonal relatives. The slices represent antibody clones and are proportional to the number of sequences in every clone. The clones marked with an asterisk are clones that exhibited tier 2 neutralization and these are represented by the variants NC37, BG18 and BG1. FIG. 1D: Upper panel: A heat map showing the neutralization potency, based on $IC_{50}$ values in TZM-bl assay, of the monoclonal antibodies NC37, BG1 and BG18. Lower panel: Neutralization potency based on $IC_{50}$ values in TZM-bl assay, of the donor polyclonal IgG from 2014, as well as NC37, BG1 and BG18 against $YU2_{WT}$, $YU2_{N280Y}$, $YU2_{N332K}$ and $YU2_{N160K}$. All TZM-bl assays were performed in duplicates. FIG. 1E: A heat map of neutralization potency based on $IC_{50}$ in TZM-bl assay, of antibodies NC37, BG1, BG18 and a 1:1:1 combination ("comb.") tested against a panel of 120 Tier 2 HIV-1 pseudoviruses. The geometric mean of all neutralized viruses and the percent breadth are indicated in the lower panel. Neutralization assays were performed in duplicates. FIG. 1F: Coverage curve based on the values in (1E).

FIG. 2A: Alignment of heavy chain amino acid sequences of 10-1074 (SEQ ID NO: 123), PGT121 (SEQ ID NO: 125), and BG18 (SEQ ID NO: 127). Asterisks indicate gaps in alignment. Arrows represent framework positions where all three antibodies are mutated compared to their respective germeline genes. CDR H1, H2 and H3 are indicated. FIG. 2B: Light chain sequence alignments as in (A) for 10-1074 (SEQ ID NO: 124), PGT121 (SEQ ID NO: 126), and BG18 (SEQ ID NO: 128). FIG. 2C: Left panel: Ribbon diagram of the $V_H$ (dark grey) and $V_L$ (light grey) domains of BG18 Fab as solved in 1.3 Aresolution. Middle panel: Surface representation of the BG18 variable domain. Right panel: The CDRH3 conformation is stabilized by hydrogen bonds (shown as dashed lines) within the loop. Interacting residues are shown as sticks, the remainder of CDRH3 and the neighboring CDRH1 are shown as ribbon diagrams. FIG. 2D: Left panel: Ribbon diagrams showing a superimposition of BG18, PGT121 and 10-1074 variable domains. Right panel: $V_L$ of BG18 and PGT121 are shown after superimposition of $V_H$. CDRL2BG18 was disordered in the crystal and is indicated by a dashed line. 10-1074 is closely related to PGT121 and was omitted for clarity. FIG. 2E: Surface representations of BG18 and PGT121. FIG. 2F: Single particle EM structure (gray transparent density) of BG505 SOSIP.664 bound to BG18 and 179NC75 Fabs. Coordinates for BG505 SOSIP.664, BG18 Fab, and a model for 179NC75 Fab (CH103 Fab: PDB 4JAM), were fit into the EM density as described in Example 1 infra. The 2D class averages are given. FIG. 2G: Comparisons of angle of BG505 binding adopted by the BG18 Fab versus the Fabs of 10-1074, PGT122 (PDB 5FYJ), PGT135 (PDB 4JM2), and PGT128 (PDB 5ACO). The densities for the 179NC75 Fabs were subtracted from the BG18-179NC75-BG505 map to facilitate comparisons.

FIG. 3A: Maximum-likelihood phylogenetic tree of single genome-derived env gene sequences from donor EB354 sampled on 2006, 2010, 2013 and 2014. Asterisk indicates clades with bootstrap support ≥90%. Three major sequence groups are arbitrarily named Clusters A, B and C. The three triangles indicate env sequences where the N-linked glycosylation site is absent. The dash-outlined boxes indicate VOC cultures; the number in the parentheses represents the number of viral env VOC sequences. FIG. 3B: Scatter plots depicting pairwise nucleotide sequence diversity of plasma env sequences from 2010, 2013 and 2014. Each dot represents the pairwise genetic difference between two sequences at a given time point. P values were determined using a two-sample U statistic-based Z test and indicate ***p<0.0005. FIG. 3C: Heat maps showing $IC_{50}$ values in TZM-bl assay of BG18, BG1, NC37 and the contemporaneous IgG purified from the same time point as the viral env genes against autologous pseudoviruses using EB354 env sequence. Stars mark pseudoviruses that are resistant to all three autologous bNAbs. Antibody 3BNC117 (described in US 2014/0328862) served as a control. The circles on the left correspond to the time points the sequence were obtained, as indicated in (3A). Neutralization assays were performed in duplicates and repeated at least twice. Gray squares indicate that the assay was not preformed. FIG. 3D: Pie charts represent the sensitivity of the autologous pseudoviruses using EB354 env sequences to each one of the three autologous bNAbs at the different time point analyzed. The number in the middle of the pies represents the number of env pseudoviruses tested, and the different slices are proportional to the number of pseudoviruses. The bNAbs are indicated on the left and the time points when the samples were collected are indicated above the charts. The bars below the pies show when antibody transcripts were detected by PCR. FIG. 3E: $IC_{50}$ values in TZM-bl assay of BG18, BG1, NC37 and the control bNAb 3BNC117 against VOCs obtained from EB354 CD4 T cells from 2014 and 2015.

FIG. 4A: Viral load values in four (BG18) and five (NC37) $HIV_{YU2}$-infected hu-mice before and after monotherapy with BG18 (top panel) or NC37 (bottom panel). The gray shaded area on the graph indicates the period of time during which BG18 (top) or NC37 (bottom) was administered. The bold lines indicate the geometric mean values in each treatment experiment. FIG. 4B: Amino acid sequence alignment of gp120 sequences from viruses cloned on day 21 after therapy with BG18 (top) or NC37 (bottom). Each horizontal bar represents the sequence of a single gp120 clone aligned to $HIV-1_{YU2}$. Amino acid substitutions are indicated as ticks. The mouse ID from which the sequence was obtained is indicated on the vertical bars. An expanded view of the boxed areas is shown on the right in each panel. FIG. 4C: Pie charts showing the recurrent mutations for BG18 (top) and NC37 (bottom) in gp120 compared to the wild-type $HIV-1_{YU2}$ sequence. The different slices are proportional to the number of sequences that carried mutations. The number in the center of the pie denotes the total number of sequences cloned. White slice in NC37 indicates lack of any recurrent mutations. FIG. 4D: Viral load values in seven hu-mice before and after treatment with a combination of BG18+NC37+BG1. Mice T1 and T2 are untreated control mice (open marks). Mice T3-T7 received the combination of BG18+NC37+BG1 (full marks). The shaded area indicates the period of time the combination of bNAbs was given. Geometric mean averages are shown in bold lines, broken for untreated group and full for the treated group. FIG. 4E: $Log_{10}$ difference in viral load compared to day 0 (before antibody administration). The asterisk indicates an outline value.

FIG. 5A: BG18, FIG. 5B: BG1.

FIG. 6A: Dendrogram of the sequences of the heavy chains of PGT121, 10-1074 and nine BG18 clonal variants, as well as their predicted germlines. FIG. 6B: Alignment of the heavy chain CDRs of PGT121 (SEQ ID NOs: 111-113), 10-1074 (SEQ ID NOs: 117-119), BG33 (SEQ ID NOs: 26-28), BG18 (SEQ ID NOs: 10-12), BG42 (SEQ ID NOs: 18-20), BG8 (SEQ ID NOs: 2-4), BG419 (SEQ ID NOs: 58-60), BG411 (SEQ ID NOs: 50-52), BG129 (SEQ ID NOs:34-36), BG426 (SEQ ID NOs: 66-68), and BG188 (SEQ ID NOs:42-44). Position common to PGT121/10-1074 and BG18 variants are highlighted. FIG. 6C: Same as (6A) but for the light chains. FIG. 6D: Alignment of the light chain CDRs of PGT121 (SEQ ID NOs: 114-116), 10-1074 (SEQ ID NOs: 120-122), BG33 (SEQ ID NOs: 30-32), BG18 (SEQ ID NOs: 14-16), BG42 (SEQ ID NOs: 22-24), BG8 (SEQ ID NOs:6-8), BG419 (SEQ ID NOs:62-64), BG411 (SEQ ID NOs:54-56), BG129 (SEQ ID NOs:38-40), BG426 (SEQ ID NOs:70-72), and BG188 (SEQ ID NOs:46-48). Position common to PGT121/10-1074 and BG18 variants are highlighted.

FIG. 8A: 2.7 Å crystal structure of a NC37 Fab-gp120 complex superimposed on an 8ANC134 Fab-gp120 complex structure (PDB 4RX4) reveals a similar gp120-binding orientation for the two antibodies. FIG. 8B: Close-up of the Fab-gp120 interface shows the extended CDRH3 of NC37 compared to the 8ANC134 CDRH3. FIG. 8C: Side view of a BG505 trimer structure in surface representation (PDB 4TVP) with predicted epitopes for NC37, 8ANC134 and NIH45-46 shown on one protomer of the trimer. The longer CDRH3 of NC37 suggests a larger contact area on an adjacent protomer (light gray) of the trimer.

FIG. 9A: Interaction between BG18 and a JR-FL mini-V3 glycopeptide carrying a $Man_9GlcNAc_2$ glycan at N301. Weak binding was observed. FIG. 9B: Interaction between BG18 and a JR-FL mini-V3 glycopeptide carrying a $Man_9GlcNAc_2$ glycan at N332. Weak binding was observed. FIG. 9C: Interaction between BG18 IgG and a JR-FL mini-V3 glycopeptide carrying a biantennary complex type N-glycan at N301. No binding was observed. FIG. 9D: Interaction between BG18 IgG and a JR-FL mini-V3 glycopeptide carrying a biantennary complex type N-glycan at N332. No binding was observed. FIG. 9E: Interaction between BG18 IgG and an A244 mini-V3 glycopeptide carrying a $Man_9GlcNAc2$ glycan at N334. Weak binding was observed. FIG. 9F: Interaction between BG18 IgG and a CAP45 mini-V3 glycopeptide carrying a $Man_9GlcNAc2$ glycan at N334. Weak binding was observed.

FIG. 10A: Pie charts represent the total env sequences amplified by single genome PCR for every collection time point. The total number of sequences obtained from every time point is denoted in the middle of the pie, and the different slices are proportional to the number of sequences. FIG. 10B: Maximum-likelihood phylogenetic tree of single genome-derived env gene sequences from donor EB354 sampled on 2006, 2010, 2013 and 2014. An asterisk indicates clades with bootstrap support ≥90%. The table on the right side shows $TCID_{50}$ values and the $IC_{50}$ values in TZM-bl assay of BG18, BG1, NC37 and the control antibody 3BNC117 against autologous pseudoviruses using EB354 env sequences. FIG. 10C: Comparing the $TCID_{50}$ values of pseudoviruses using EB354 env that were resistant to all three bNAbs as opposed to pseudoviruses using EB354 env sequences that were sensitive to atleast one bNAb. P-value (t-test)=0.0016.

FIGS. 11A, 11B, 11C represent $HIV_{YU2}$-infected hu-mice treatment with BG8. FIG. 11A: Viral load values in four hu-mice before and after administration of BG8. The gray shaded area on the graph indicates the period of time during which antibody was administered. The bold lines indicate the geometric mean values riment. FIG. 11B: Amino acid sequence alignment of gp120 sequences from viruses cloned on day 21 after therapy. Each horizontal gray bar represents the sequence of a single gp120 clone aligned to $HIV-1_{YU2}$.

Amino acid substitutions are indicated as black ticks. The mouse ID from which the sequence was obtained is indicated on the vertical black bars. An expanded view of the boxed areas is shown on the right in each panel. FIG. 11C: Pie charts showing the recurrent mutations in gp120 compared to the wild-type HIV-1$_{YU2}$ sequence following BG8 therapy. The number in the center of the pie denotes the total number of sequences cloned; the slices represent the most consistently mutated areas in gp120 and are proportional to the number of sequences that carried mutations.

DETAILED DESCRIPTION

A. Definitions

Figures 1A, 1B, 1C:
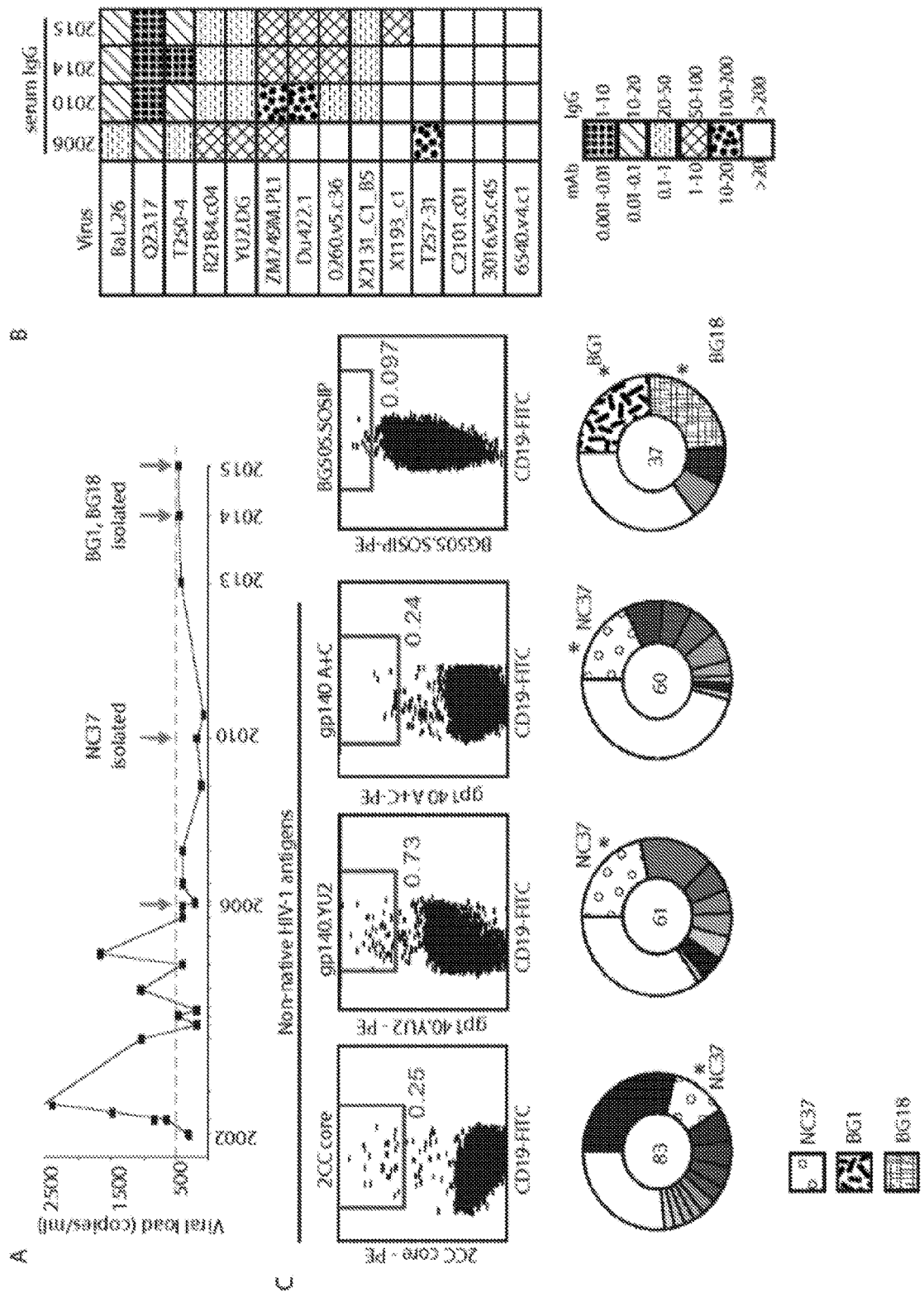
FIGS. 1A, 1B, 1C, 1D, 1E, 1F represent HIV-1 antibody repertoire in donor EB354.

An anti-HIV-1 antibody may take one of numerous forms in the art, as disclosed herein. Antibodies are in part defined by the antigens to which they bind, thus, an "anti-HIV-1 antibody" is any such antibody which specifically binds at least one epitope found on the viral envelope of human immunodeficiency virus 1 ("HIV-1"), e.g. within gp120 and/or gp140, as described herein. It is understood in the art that an antibody is a glycoprotein comprising at least two heavy (H) chains and two light (L) chains inter-connected by disulfide bonds, or an antigen binding portion thereof. A heavy chain is comprised of a heavy chain variable region (VH) and a heavy chain constant region (CH1, CH2 and CH3). A light chain is comprised of a light chain variable region (VL) and a light chain constant region (CL). The variable regions of both the heavy and light chains comprise framework regions (FWR) and complementarity determining regions (CDR). The four FWR regions are relatively conserved while CDR regions (CDR1, CDR2 and CDR3) represent hypervariable regions and are arranged from NH2 terminus to the COOH terminus as follows: FWR1, CDR1, FWR2, CDR2, FWR3, CDR3, FWR4. The variable regions of the heavy and light chains contain a binding domain that interacts with an antigen while, depending of the isotype, the constant region(s) may mediate the binding of the immunoglobulin to host tissues or factors. It is known in the art that it is possible to manipulate monoclonal and other antibodies and use techniques of recombinant DNA technology to produce other antibodies or chimeric molecules which retain the specificity of the original antibody. Such techniques may evolve introducing DNA encoding the immunoglobulin variable region, or CDRs, of an antibody to the constant regions, or constant regions plus framework regions, of a different immunoglobulin.

The term "antibody" (Ab) as used herein is used in the broadest sense and specifically may include any immunoglobulin, whether natural or partly or wholly synthetically produced, including but not limited to monoclonal antibodies, polyclonal antibodies, multispecific antibodies (for example, bispecific antibodies and polyreactive antibodies), and antibody fragments. Thus, the term "antibody" as used in any context within this specification is meant to include, but not be limited to, any specific binding member, immunoglobulin class and/or isotype (e.g., IgG1, IgG2a, IgG2b, IgG3, IgG4, IgM, IgA1, IgA2, IgD, and IgE) and biologically relevant fragment or specific binding member thereof, including but not limited to Fab, F(ab')$_2$, scFv (single chain or related entity) and (scFv)$_2$.

The term "antibody fragments" as used herein may include those antibody fragments obtained using techniques readily known and available to those of ordinary skill in the art, as reviewed herein. Therefore, in addition to the definition for "antibody" presented supra, the term "antibody" may further encompass any polypeptide or protein comprising a portion of an intact antibody, such as the antigen binding or variable region of the intact antibody. These can be derived from natural sources, or they may be partly or wholly synthetically produced. Examples of antibody fragments include, but are not limited to, Fab, Fab', F(ab')2, and Fv fragments; diabodies, and linear antibodies. The terms "antigen binding portion", "antigen binding fragment" or "Fab" as used herein may refer to a region on an antibody that binds to antigens. One of ordinary skill in the art will understand that Fabs are comprised of one constant one variable domain of each of the heavy and light chain of an antibody.

The term "monoclonal antibody" or "mAb" as used herein may refer to an antibody obtained from a population of substantially homogeneous antibodies, i.e., the individual antibodies comprising the population are identical except for possible naturally occurring mutations that may be present in minor amounts. Monoclonal antibodies may include but chimeric antibodies, humanized antibodies, recombinant antibodies, and human antibodies. Methods of producing monoclonal antibodies are well known in the art, with some specific examples discussed infra including hybridoma technology, recombinant antibody production, e.g. by phage display or yeast display technology, production by transgenic mice, and single B cell culture. Methods that involve amplifying heavy and/or light chains of antibody genes (e.g. a plasmid or cosmid) by PCR (or similar technology) either in vitro or in bacterial and/or mammalian and/or yeast systems are considered to be within the scope of this present invention.

The terms "conservative sequence modifications" or "conservative substitutions" as used herein may refer to amino acid modifications to a target epitope of the invention that does not significantly affect or alter the binding characteristics of the anti-HIV-1 antibodies to the epitope(s). Such conservative modifications include amino acid substitutions, additions and deletions. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a target epitope that the anti-HIV-1 antibodies of the invention specifically bind to, e.g. epitopes on the viral envelope of HIV-1, e.g. epitopes on gp120 and/or gp140, can be replaced with other amino acid residues from the same side chain family and the antibodies of the present invention can be tested against the target epitope can be tested, for example using functional assays described herein or otherwise known in the art.

The term "biological sample" refers to a sample obtained from an organism (e.g., patient) or from components (e.g., cells) of an organism. The sample may be of any biological tissue, cell(s) or fluid. The sample may be a "clinical sample" which is a sample derived from a subject, such as a human patient. Such samples include, but are not limited to, saliva, sputum, blood, blood cells (e.g., white cells), bodily fluids, lavages, pancreatic juices, gastric juices, discharges, CSF, lymph amniotic fluid, plasma, semen, bone marrow, and tissue or fine needle biopsy samples, urine, stool, peritoneal fluid, and pleural fluid, or cells therefrom, and any combinations thereof. Biological samples may also include sections of tissues such as frozen sections taken for histological purposes. A biological sample may also be referred to as a "patient sample." A biological sample may also include a substantially purified or isolated protein, membrane preparation, or cell culture.

The term "bispecific antibody" refers to artificial immunoglobulin constructs that are comprised of fragments of two different monoclonal antibodies that bind to two different antigens. There are several distinct types of bispecific antibodies, including but not limited to trifunctional antibodies and chemically linked Fabs. The anti-HIV-1 antibodies of the present invention may comprise bispecific antibodies, and include fragments of one or more different anti-HIV-1 antibodies, including one or more different anti-HIV-1 antibodies of the present invention, e.g. BG18 and BG1, or one or more anti-HIV-1 antibodies of the present invention and known anti-HIV-1 antibodies, e.g. BG18 and 3BNC117 (described in US 2014/0328862), or BG18 aNd VRCO1, described in U.S. Pat. No. 8,637,036. Bispecific anti-HIV bNabs and methods of making and use thereof are described in PCT/US16/64713, hereby incorporated by reference.

The terms "effective amount" or "therapeutically effective amount" as used herein may refer to an amount of the compound or agent that is capable of producing a medically desirable result in a treated subject. The treatment method can be performed in vivo or ex vivo, alone or in conjunction with other drugs or therapy. A therapeutically effective amount can be administered in one or more administrations, applications or dosages and is not intended to be limited to a particular formulation or administration route.

The terms "specific binding," "selective binding," "selectively binds," and "specifically binds," may refer to antibody binding to an epitope on a predetermined antigen but not to other antigens. Typically, the antibody binds with an equilibrium dissociation constant ($K_D$) of approximately less than $10^{-6}$ M, such as approximately less than $10^{-7}$ M, $10^{-8}$ M, $10^{-9}$ M or $10^{-10}$ M or even lower when determined by, e.g., equilibrium dialysis or surface plasmon resonance (SPR) technology in a BIACORE® 2000 surface plasmon resonance instrument using the predetermined antigen, e.g., an epitope on the viral envelope of HIV-1, e.g. gp120, as the analyte and the antibody as the ligand, or Scatchard analysis of binding of the antibody to antigen positive cells, and (ii) binds to the predetermined antigen with an affinity that is at least two-fold greater than its affinity for binding to a non-specific antigen (e.g., BSA, casein) other than the predetermined antigen or a closely-related antigen.

The term "homology" as used herein may refer to the existence of shared structure between two compositions. The term "homology" in the context of proteins may refer to the amount (e.g. expressed in a percentage) of overlap between two or more amino acid and/or peptide sequences. In the context of nucleic acids, the term may refer to the amount (e.g. expressed in a percentage) of overlap between two or more nucleic acid sequences. As used herein, the percent (%) homology between two sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm. Such homology is well-represented in the art via local alignment tools and/or algorithms, e.g. BLAST and/or BLAST 2.0, and may include pairwise alignment, multiple sequence alignment methods, structural alignment methods, and/or phylogenetic analysis methods.

The terms "co-administration," "co-administered," and "in combination with" as used herein may refer to the administration of at least two agents or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. For example, the anti-HIV-1 antibodies of the present invention may be co-administered with each other, or may be co-administered alongside other antibodies, e.g. other broadly neutralizing antibodies, such as, for example, those broadly neutralizing anti-HIV antibodies disclosed in US 2014/0328862, e.g. 3BNC117, or VRC01, described in U.S. Pat. No. 8,637,036, hereby incorporated by reference in its entirety, or optionally, co-administered with other HIV agents. Co-administration may or may not occur simultaneously, e.g. one or more anti-HIV-1 antibody of the present invention may be administered prior to or after another anti-HIV-1 antibody of the present invention (or other anti-HIV antibody or other HIV agents), or may be administered at the same or substantially similar time. One of ordinary skill in the art will appreciate that co-administration is not meant to be limiting in time as it is meant to describe administration alongside other compounds and/or therapies as part of a patient regimen.

The term "HIV agent" as used herein may refer to a therapy for the treatment of HIV that does not, by itself, comprise an anti-HIV-1 antibody. For example, non-nucleoside reverse transcriptase inhibitors (NNRTIs), nucleoside reverse transcriptase inhibitors (NRTIs), protease inhibitors (PIs), fusion inhibitors, CCR5 antagonists/entry inhibitors, integrase strand transfer inhibitors (INSTIs), and combinations thereof, would all be considered "HIV agents", as they are non-antibody based therapeutic treatments that can be co-administered with one or more anti-HIV-1 antibodies of the present invention, and/or additional anti-HIV-1 antibodies. One of ordinary skill in the art will appreciate that this list should not be considered exhaustive and as the state of the art advances and additional treatments become available, they are considered within the scope of this definition.

The term "carriers" as used herein may include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include, but not limited to, buffers such as phosphate, citrate, and other organic acids; antioxidants including, but not limited to, ascorbic acid; low molecular weight (less than about 10 residues) polypeptide; proteins, such as, but not limited to, serum albumin, gelatin, or immunoglobulins; hydrophilic polymers such as, but not limited to, polyvinylpyrrolidone; amino acids such as, but not limited to, glycine, glutamine, asparagine, arginine or lysine; monosaccharides, disaccharides, and other carbohydrates including, but not limited to, glucose, mannose, or dextrins; chelating agents such as, but not limited to, EDTA; sugar alcohols such as, but not limited to, mannitol or sorbitol; salt-forming counterions such as, but not limited to, sodium; and/or nonionic surfactants such as, but not limited to, TWEEN.; polyethylene glycol (PEG), and PLURONICS.

The term "treating" or "treatment" of a disease refers to executing a protocol, which may include administering one or more drugs to a patient (human or otherwise), in an effort to alleviate signs or symptoms of the disease. Alleviation can occur prior to signs or symptoms of the disease appearing as well as after their appearance. Thus, "treating" or "treatment" includes "preventing" or "prevention" of disease. The terms "prevent" or "preventing" refer to prophylactic and/or preventative measures, wherein the object is to prevent or slow down the targeted pathologic condition or disorder. For example, in the case of infection with immunodeficiency virus 1 (HIV-1), "preventing" or "preventing" may arise in a situation where a course of treatment is advanced in order to prevent or stall infection by HIV-1, such as through passive vaccination. Such "preventing" or "prevention" also arise in the case of latent infection by HIV-1, for example in those individuals who are seropositive but are not exhibiting any symptoms (i.e. has not progressed to symptoms of AIDS), in which the object would be to prevent active infection and/or clear a patient of said HIV-1 infection. In addition, "treating" or "treatment" does not require complete alleviation of signs or symptoms, does not require a cure, and specifically includes protocols that have only a marginal, yet positive, effect on the patient.

The term "epitope" as used herein may refer to the region of an antigen to which an antibody or T cell binds, e.g. a region of the viral envelope of HIV-1, including but not limited to a glycoprotein, e.g. gp120, or a region on a glycoprotein. An "antigen" refers to a substance that elicits an immunological reaction or binds to the products of that reaction.

The terms "purified" or "isolated" antibody, peptide, polypeptide, or protein refers to a peptide, polypeptide, or protein, as used herein, may refer to a peptide, polypeptide, or protein that has been separated from other proteins, lipids, and nucleic acids with which it is naturally associated. The polypeptide/protein can constitute at least 10% (i.e., any percentage between 10% and 100%, e.g., 20%, 30%, 40%, 50%, 60%, 70%, 80%, 85%, 90%, 95%, and 99%) by dry weight of the purified preparation. Purity can be measured by any appropriate standard method, for example, by column chromatography, polyacrylamide gel electrophoresis, or HPLC analysis. An isolated polypeptide/protein (e.g., anti-HIV-1 antibodies) described in the invention can be produced by recombinant DNA techniques.

B. Broadly Neutralizing Anti-HIV-1 Antibodies

The present invention relates to broadly neutralizing anti-HIV-1 antibodies (bNabs) and antigen-binding portions thereof. In particular, the present invention relates to several distinct monoclonal antibodies, BG18, NC37, and BG1, their antigen-binding portions including but not limited to their complementarity determining regions (CDRs), and derivatives and variants thereof, which display broad and potent neutralization of HIV-1 in vivo (see Example 1 infra). Thus, the anti-HIV-1 antibodies of the present invention possess strong therapeutic utility, either alone or in combination with one another, or with other bNabs, or with other HIV treatments, as discussed herein.

Each of BG18, NC37 and BG1 has distinct, non-overlapping epitopes. NC37 recognizes the CD4bs. NC37 and its clonal variants display characteristics of both $V_H1$-2 and $V_H1$-46-derived bNAbs; however, structural analyses suggest that NC37 recognizes Env in a $V_H1$-46-type manner. Without wishing to be bound by theory, the long CDRH3 of NC37 is predicted to make contacts with the adjacent protomer on the trimer, thereby recognizing a quaternary trimer epitope, the core of which overlaps with the CD4bs.

BG1 binds to the V1V2 region of Env, another frequent target of bNAbs arising during natural infection. BG1 represents the first antibody in this class (bNAbs) to be isolated from a Clade B-infected donor. Its potency is similar to members of the VRC26 antibody family, such as those disclosed in N. A. Doria-Rose et al, Developmental pathway for potent V1V2-directed HIV-neutralizing antibodies. *Nature* 509, 55-62 (2014), but is less potent than PG9/16 and PGDM1400 bNAbs. Like other VIV2 bNAbs isolated to date, BG1 has a long, tyrosine-rich CDRH3.

BG18, the most potent of each of BG18, NC37 and BG1, is directed against the $Asn332_{gp120}$-centered glycan patch at the base of V3 loop. This is a heavily glycosylated region that includes carbohydrates at positions $Asn332_{gp120}$, $Asn301_{gp120}$, $Asn386_{gp120}$, $Asn392_{gp120}$, $Asn137_{gp120}$, $Asn156_{gp120}$. A number of monoclonal bNAbs that bind to both protein and carbohydrate components at this site have been isolated, including PGT121-124, as described in L. M. Walker et al., Broad neutralization coverage of HIV by multiple highly potent antibodies. *Nature* 477, 466-470 (2011) and 10-1074, as described in H. Mouquet et al., Complex-type N-glycan recognition by potent broadly neutralizing HIV antibodies. *Proceedings of the National Academy of Sciences of the United States of America* 109, E3268-3277 (2012). All of these bNAbs were isolated from a Clade A donor and can be sub-classified into those that rely exclusively on the $Asn332_{gp120}$ glycan (10-1074 and PGT124), and those that also make contacts with surrounding glycans in the V3 glycan patch (PGT121-123). BG18 and its clonal variants resemble 10-1074 in that they rely on $Asn332_{gp120}$, but BG18 is more potent than published anti-V3 bNAbs and the first to be isolated from a Clade B donor.

BG18 differs from previously characterized members of this class by a surprisingly distinctive orientation of the CDRH3 and the light chain domain. In addition, BG18 differs from other members of this group of antibodies in that it has a shorter CDRH3 and no insertions or deletions, while without wishing to be bound by theory, suggests that BG18-like antibodies may be easier to elicit. In the absence of a high-resolution structure of a BG18-Env complex, it is difficult to predict how the shorter CDRH3 of BG18 interacts with Env. Structural studies of Env complexes with PGT122 and 10-1074 Fabs demonstrate that they adopt a similar angle of approach, which is approximately perpendicular to the gp120 protomers within an Env trimer.

The BG18-Env EM structure, although not of sufficient resolution to resolve detailed interactions, nevertheless demonstrates that BG18 approaches Env from a different angle, which is shifted by up to 40° towards the gp120 promoter relative to the approach angles of 10-1074 and PGT122. BG18 clonal variants and derivatives, including 354BG8, 354BG18, 354BG42, 354BG33, 354BG129, 354BG188, 354BG411, and 354BG426 along with their full-length sequences, heavy and light chain complementarity-determining regions (CDRs), are set forth below in Table 1. A dendrogram of BG18 variants is set forth in FIG. 6 and discussed in Example 1 infra. BG1 clonal variants and derivatives, including BG1, BG22, and BG47, along with their full-length sequences, heavy and light chain complementarity-determining regions (CDRs), are set forth below in Table 2.

TABLE 1

Sequences of BG18 variants

| Name | SEQ ID NO: | Sequence |
|---|---|---|
| 354BG8IgH | 1 | EVQLRESGPRLVKPSETLSLSCDVFGDSRPSDHSWTWVRQPPGK ALEWIGDVHYNGDNTYNPSLRGRVKIDVDRSTHRFSLTLKSLTA ADTGIYFCARNVIRVFGVISLGEWFHYGMDVWGPGTAVIVSS |
| CDR1 | 2 | GDSRPSDHS |
| CDR2 | 3 | VHYNGDN |
| CDR3 | 4 | NVIRVFGVISLGEWFHYGMDV |
| 354BG8 IgL | 5 | SSELTQAPSVSVSPGQTATIACSGPPLASRYTYWYRQKPGQAPV LIIFRDRQFPSGVSGRFSASKSGTTATLTIRDVQVEDEGDYYCQ SSDTSDSYKMFGGGTTLTVL |
| CDR1 | 6 | PLASRY |
| CDR2 | 7 | RDR |
| CDR3 | 8 | QSSDTSDSYKM |
| 354BG18 IgH | 9 | QVQLRESGPGLVKPSETLSLSCTVSNDSRPSDHSWTWVRQSPGK ALEWIGDIHYNGATTYNPSLRSRVRIELDQSIPRFSLKMTSMTA ADTGMYYCARNAIRIYGVVALGEWFHYGMDVWGQGTAVTVSS |
| CDR1 | 10 | NDSRPSDHS |
| CDR2 | 11 | IHYNGAT |
| CDR3 | 12 | NAIRIYGVVALGEWFHYGMDV |
| 354BG18 IgL | 13 | SSELTQPPSVSVSPGQTARITCSGAPLTSRFTYWYRQKPGQAPV LIISRSSQRSSGWSGRFSASWSGTTVTLTIRGVQADDEADYYCQ SSDTSDSYKMFGGGTKLTVL |
| CDR1 | 14 | PLTSRF |
| CDR2 | 15 | RSS |
| CDR3 | 16 | QSSDTSDSYKM |
| 354BG42 IgH | 17 | EVQLRESGPGLVKPSETLSLSCDVFGDSRPSDHSWTWVRQPPGK ALEWIGDVHYNGDTTYNPSLRGRVKIDVDRSTHRFSLTLNSLTA ADTGIYFCARNVIRVFGVISLGEWFHYGMDVWGQGTAVTVSS |
| CDR1 | 18 | GDSRPSDHS |
| CDR2 | 19 | VHYNGDT |
| CDR3 | 20 | NVIRVFGVISLGEWFHYGMDV |
| 354BG42 IgL | 21 | SSELTQAPSVSVSPGQTATIACSGPPLASRYTYWYRQKPGQAPV LIIFRDRQFPSGVSGRFSASKSGTTATLTIRDVQVEDEGDYYCQ SSDTSDSYKMFGGGTTLTVL |
| CDR1 | 22 | PLASRY |
| CDR2 | 23 | RDR |
| CDR3 | 24 | QSSDTSDSYKM |
| 354BG33 IgH | 25 | QVQLRESGPGLVKPSETLSLTCTVSNDSRPSDHSWTWVRQSPGK ALEWIGDIHYNGATTYNPSLRSRVRIELDQSIPRFSLKMTSMTA ADTGMYYCARNAIRIYGVVALGEWFHYGMDVWGQGTAVTVSS |
| CDR1 | 26 | NDSRPSDHS |
| CDR2 | 27 | IHYNGAT |
| CDR3 | 28 | NAIRIYGVVALGEWFHYGMDV |
| 354BG33 IgL | 29 | SSELTQPPSVSVSPGQTAKITCSGAALTSRFTYWYRQKPGQAPV LIISRTSQRSSGWSGRFSASWSGTTVTLTIRGVQADDEGDYYCQ SSDTSDSYKMFGGGTKLTVL |

TABLE 1-continued

Sequences of BG18 variants

| Name | SEQ ID NO: | Sequence |
|---|---|---|
| CDR1 | 30 | ALTSRF |
| CDR2 | 31 | RTS |
| CDR3 | 32 | QSSDTSDSYKM |
| 354BG129 IgH | 33 | EVQLRESGPGLVKPSGNMALTCTISGDSRPSDHSWTWVRQSPGK ALEWIGDIHYGGDITYNPSLRSRVKLEVDTSTNRFFLKMTSLTV ADTGIYFCARNVIRVFGVIALGEWFHYGMDVWGQGTAITVSP |
| CDR1 | 34 | GDSRPSDHS |
| CDR2 | 35 | IHYGGDI |
| CDR3 | 36 | NVIRVFGVIALGEWFHYGMDV |
| 354BG129 IgL | 37 | SSELTQTPSVTVSPGETARIACSGPPLASRYCYWYRQKPGQAPV LIIFRDRQFSSGMSGRFASSHSGTTVTLTIRDVRVEDEADYYCQ SSDINDSYKMFGGGTKVTVL |
| CDR1 | 38 | PLASRY |
| CDR2 | 39 | RDR |
| CDR3 | 40 | QSSDINDSYKM |
| 354BG188 IgH | 41 | EVQLRESGPGLVKPSGNMALTCTISGDSRPSDHSWTWVRQSPGK TLEWIGDIHYGGDITYNPSLRSRVKLEVDTSSNRFFLKMTSLTV ADTGIYFCARNVIRVFGVIALGEWFHYGMDVWGQGTAITVSP |
| CDR1 | 42 | GDSRPSDHS |
| CDR2 | 43 | IHYGGDI |
| CDR3 | 44 | NVIRVFGVIALGEWFHYGMDV |
| 354BG188 IgL | 45 | SSELTQTASVTVSPGETARIACSGPPLASRYCYWYRQKPGQAPV LIIFRDRQFSSGISGRFSSSQSGTTVTLTIRDVRVEDEADYYCQ SSDTSDSFKMFGGGTKLTVL |
| CDR1 | 46 | PLASRY |
| CDR2 | 47 | RDR |
| CDR3 | 48 | QSSDTSDSFKM |
| 354BG411 IgH | 49 | QVQLRESGPGLVKPSGNMALTCTISGDSRPSDHSWTWVRQSPGK ALEWIGDIHYGGDITYNPSLRSRVELEVDRSTNRFFLKMTSLSV ADTGMYFCARNVIRVFGVIALGEWFHYGMDVWGQGTAITVSP |
| CDR1 | 50 | GDSRPSDHS |
| CDR2 | 51 | IHYGGDI |
| CDR3 | 52 | NVIRVFGVIALGEWFHYGMDV |
| 354BG411 IgL | 53 | SSELTQAPSVTVSPGDTARIACSGPPLATRYCYWYRQKSGQAPV LIIFRDRQFSSGVSGRFSSSQSGSTVTLTIRDVRVEDEADYYCQ SSDTSDSYKMFGGGTKLTVL |
| CDR1 | 54 | PLATRY |
| CDR2 | 55 | RDR |
| CDR3 | 56 | QSSDTSDSYKM |
| 354BG419 IgH | 57 | QVQLRESGPGLVKPSETLSLSCDVFGDSRPSDHSWTWVRQPPGK ALEWIGDIHYNGDKTYNPSLRGRVKIDVDRSTHRFSLTLNSLTA ADTGMYFCARNVIRVFGVISLGEWFHYGMDVWGPGTAVTVSS |
| CDR1 | 58 | GDSRPSDHS |
| CDR2 | 59 | IHYNGDK |
| CDR3 | 60 | NVIRVFGVISLGEWFHYGMDV |

TABLE 1-continued

Sequences of BG18 variants

| Name | SEQ ID NO: | Sequence |
|---|---|---|
| 354BG419 IgL | 61 | SSELTQAPSVSVSPGQTARIACSGPPLASRYTYWYRQKPGQAPV LIIFRDRQFPSGVSGRFSASKSGTTGTLTIRDVQAEDEGDYYCQ SSDTSDSYKMFGGGTTLTVL |
| CDR1 | 62 | PLASRY |
| CDR2 | 63 | RDR |
| CDR3 | 64 | QSSDTSDSYKM |
| 354BG426 IgH | 65 | QVQLRESGPGLVKPSGNMALTCTISGDSRPSDHSWTWVRQSPGK ALEWIGDIHYGGDITYNPSLRSRVKLEVDTSSNRFFLKMTSLTV ADTGIYFCARNVIRVFGVIALGEWFHYGMDVWGQGTAITVSP |
| CDR1 | 66 | GDSRPSDHS |
| CDR2 | 67 | IHYGGDI |
| CDR3 | 68 | NVIRVFGVIALGEWFHYGMDV |
| 354BG426 IgL | 69 | SSELTQAPSVTLSPGETARIACSGPPLASRYCYWYRQKPGQAPV LIIFRDRQFSSGISGRFSSSQSGTTVTLTIRDVRVEDEADYYCQ SSDNSDSFKMFGGGTKLTVL |
| CDR1 | 70 | PLASRY |
| CDR2 | 71 | RDR |
| CDR3 | 72 | QSSDNSDSFKM |

TABLE 2

Sequences of BG1 variants

| Name | SEQ ID NO: | Sequence |
|---|---|---|
| BG1IgH | 73 | AEQLVESGGGLVPPGRSLRLSCSASGFYFPDYAMAWVRQAPGQG LQWVGFMRGWAYGGSAQFAAFAVGKFAISRDDGRNVVYLDKNP TFEDTGVYFCAREQRNKDYRYGQEGFGYSYGMDVWGRGTTVVVS T |
| CDR1 | 74 | GFYFPDYA |
| CDR2 | 75 | MRGWAYGGSA |
| CDR3 | 76 | EQRNKDYRYGQEGFGYSYGMDV |
| BG1 IgL | 77 | DIHMTQSPVSLSASVGDRVTITCRASHFIANYVNWYQQKPGKAP TLLIFESSTLQRGVPSRFSAYGDGTEFTLSINTLQPEDFASYIC QQSHSPPVTFGAGTRVDQK |
| CDR1 | 78 | HFIANY |
| CDR2 | 79 | ESS |
| CDR3 | 80 | QQSHSPPVT |
| BG22 IgH | 81 | EERLVESGGGLVPPGRSLRLSCSAFDFYFPDYAMAWVRQAPGKG LEWIGFIRGWAYGQAAQYGKSASGRMTISRDDSRRVVYLDIKSP IEEDTGAYFCAREQRGGDGRYSGDGFGYPYGMDVWGRGTMVTVS A |
| CDR1 | 82 | DFYFPDYA |
| CDR2 | 83 | IRGWAYGQAA |
| CDR3 | 84 | EQRGGDGRYSGDGFGYPYGMDV |

TABLE 2-continued

Sequences of BG1 variants

| Name | SEQ ID NO: | Sequence |
|---|---|---|
| BG22 IgL | 85 | DILMTQSPVSLSASIGERITITCRAS<u>HFIANY</u>VNWYQQRPGKAP<br>KLLIF<u>QSW</u>TLNRGIPSRFSGYGDGTEFTLSISALQSEDFGTYIC<br><u>QQSHSPPLS</u>FGGGTRVDQT |
| CDR1 | 86 | <u>HFIANY</u> |
| CDR2 | 87 | <u>QSW</u> |
| CDR3 | 88 | <u>QQSHSPPLS</u> |
| BG47 IgH | 89 | EERLVESGGGLVPPGRSLRLSCSAF<u>DFYFPDYA</u>MAWVRQAPGRA<br>LEWIGF<u>IRGWAYGQSA</u>QYGKSASGRMTISRDDSRRVVYLDIKSP<br>THEDTGVYFCAR<u>EQRGANGRYGGDGFGYSYGMDV</u>WGRGTMVSVS<br>A |
| CDR1 | 90 | <u>DFYFPDYA</u> |
| CDR2 | 91 | <u>IRGWAYGQSA</u> |
| CDR3 | 92 | <u>EQRGANGRYGGDGFGYSYGMDV</u> |
| BG47 IgL | 93 | DIQMTQSPFTLSASVGERVTITCRAS<u>HFIANY</u>VNWYQQRPGRAP<br>KLLIF<u>ESS</u>TLNRGVPSRFSGSGDGTEFTLSISALQSEDFATYIC<br><u>QQSHSPPVS</u>FGGGTRVDQT |
| CDR1 | 94 | <u>HFIANY</u> |
| CDR2 | 95 | <u>ESS</u> |
| CDR3 | 96 | <u>QQSHSPPVS</u> |

One of ordinary skill in the art will appreciate that the complementarity determining regions ("CDRs") of most antibodies, e.g., NC37, BG1, including all variants of BG1, and BG18, including all variants of BG18, largely determine the biological activity of the antibodies by forming the paratope on the antibody, with the CDRH3 possessing the most distinctive character. Accordingly, the antibodies of the present invention may comprise NC37, its CDRs, BG1, its CDRs, and BG18, and its CDRs, including all variants of NC37, BG1, and BG18 and their respective CDRs. One of ordinary skill in the art will also realize that the antibodies of the present invention may contain conservative substitutions, including in the CDRs, and still be within the scope of the invention. Accordingly, some embodiments of the present invention are directed to antibodies and antigen-binding portions thereof expressing the CDRs listed in Tables 1 and 2.

For example, some embodiments of the present invention are directed to antibodies or antigen-binding portions thereof having a heavy chain comprising one or more of SEQ ID NOs: 1, 9, 17, 25, 33, 41, 49, 57, 65, 73, 81, and 89 or a certain degree of homology with one or more of SEQ ID NOs: 1, 9, 17, 25, 33, 41, 49, 57, 65, 73, 81, and 89, e.g. at least 75%, 80%, 85%, 90%, 95%, 96%, 97%, 98%, 99%, and any intervening ranges therein. One or more of SEQ ID NOs: 1, 9, 17, 25, 33, 41, 49, 57, 65, 73, 81, and 89 may have conservative substitutions. Some embodiments of the present invention are directed to antibodies or antigen-binding portions thereof having a light chain comprising one or more of SEQ ID NOs: 5, 13, 21, 20, 37, 45, 53, 61, 69, 77, 85, and 93 or a certain degree of homology with one or more of SEQ ID NOs: 55, 13, 21, 20, 37, 45, 53, 61, 69, 77, 85, and 93, e.g at least 75%, 80%, 85%, 90%, 95%, 96%, 97%, 98%, 99%, and any intervening ranges therein. One or more of SEQ ID NOs: 5, 13, 21, 20, 37, 45, 53, 61, 69, 77, 85, and 93 may have conservative substitutions.

IgG heavy chains are typically bout 400 to about 600 amino acids in size, more typically 450 to about 550 amino acids. The variable region of each heavy chain, irrespective of antibody class, is typically about 100-140 amino acids long, most typically about 110-130 amino acids. The light chains are typically about 210-220 amino acids long, more typically 211-217. The variable region of light chains are typically around 100-120 amino acids long.

Some embodiments of the present invention are directed to antibodies or antigen-binding portions thereof having one or more CDRs within the heavy chain comprising one or more of SEQ ID NOs: 2-4, 10-12, 18-20, 26-28, 34-36, 42-44, 50-52, 58-60, 66-68, 74-76, 82-84, and 90-92 or a certain degree of homology with one or more of SEQ ID NOs: 2-4, 10-12, 18-20, 26-28, 34-36, 42-44, 50-52, 58-60, 66-68, 74-76, 82-84, and 90-92, e.g at least 75%, 80%, 85%, 90%, 95%, 96%, 97%, 98%, 99%, and any intervening ranges therein. One or more of SEQ ID NOs: 2-4, 10-12, 18-20, 26-28, 34-36, 42-44, 50-52, 58-60, 66-68, 74-76, 82-84, and 90-92 may have conservative substitutions.

Some embodiments of the present invention are directed to antibodies or antigen-binding portions thereof having one or more CDRs within the light chain comprising one or more of SEQ ID NOs: 6-8, 14-16, 22-24, 30-32, 38-40, 46-48, 54-56, 62-64, 70-72, 78-80, 86-88, and 94-96 or a certain degree of homology with one or more of SEQ ID NOs: 6-8, 14-16, 22-24, 30-32, 38-40, 46-48, 54-56, 62-64, 70-72, 78-80, 86-88, and 94-96, e.g. at least 75%, 80%, 85%, 90%, 95%, 96%, 97%, 98%, 99%, and any intervening ranges therein. One or more of SEQ ID NOs: 6-8, 14-16, 22-24, 30-32, 38-40, 46-48, 54-56, 62-64, 70-72, 78-80, 86-88, and 94-96 may have conservative substitutions.

Furthermore, the antibodies of the present invention may be comprised of antigen binding portions, e.g. CDRs, from different individual bNabs, including but not limited to those bNabs of the present invention. Purely by way of example, an engineered derivative may comprise a light chain from one of NC37, BG1, or BG18, including any variants, and a heavy chain from a different bNab, including one of NC37, BG1, or BG18, including any variants. Or, an engineered derivative may comprise a light chain from one variant of BG18 and a heavy chain from another variant of BG18. One skilled in the art will recognize that recombinant antibody production methods allow for a significant number of recombinant antibodies, each of which is expressly considered to be within the scope of the present disclosure. Accordingly, the bNabs of the present invention may be made by recombinant DNA methods, such as those described in U.S. Pat. No. 4,816,567. DNA encoding the monoclonal antibodies of the invention can be readily isolated and sequenced using conventional procedures (e.g, by using oligonucleotide probes that are capable of binding specifically to genes encoding the heavy and light chains of murine antibodies). Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Once produced, recombinantly or otherwise, the anti-HIV-1 antibodies may be purified or isolated, such that the antibodies are substantially free from, for example, any serum, supernatant, or other cellular cultures or related materials. Methods of antibody purification are known in the art, and may include selective enrichment or specific isolation methods. For example, affinity purification may be used, such as class-specific affinity. Fractionation methods may also be employed at the outset to help isolate subset of sample proteins that include immunoglobulins. Typically, antigen-specific affinity is applied to isolate antibodies that bind to the antigen. The antibodies may then be combined with a carrier, buffer, diluent, solvent, and/or preservatives, etc., that serve to create pharmaceutically acceptable anti-HIV-1 antibody compositions.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking. In vitro methods are also suitable for preparing monovalent antibodies. Digestion of antibodies to produce fragments thereof, particularly, Fab fragments, can be accomplished using routine techniques known in the art.

Human monoclonal antibodies can be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1); 86-95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al, Bio/Technology 10, 779-783 (1992); Lonberg et al, Nature 368 856-859 (1994); Morrison, Nature 368, 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

Some embodiments of the invention are directed to vectors and vector systems containing nucleotide sequences that code for the variable regions, including but not limited to CDRs of the anti-HIV-1 antibodies of the present invention, e.g. NC37, BG1, and BG18, including any variants, and antigen-binding portions thereof. The vector may be, for example but not necessarily, a plasmid; other recombinant vectors are known in the art and may include, e.g. phage vectors such as a λ phage vector, other viral vectors such as non-replicating adenoviral vector, cosmids, and/or artificial chromosomes. A vector system may or may not be separately inducible, i.e. have different promoter and/or repressor elements. Common to most engineered vectors are origin of replications, multicloning sites, and selectable markers, so as long as a vector (including systems of vectors, e.g. multiple plasmids) contain such a system they are considered to be covered by the scope of this invention. It is well within one of ordinary skill in the art to derive nucleic acid sequences from a given peptide sequence and clone them into a system of choice. Accordingly, some embodiments, the present invention is directed to a vector or system of vectors containing one or more nucleic acid sequences encoding one or more of SEQ ID NO: 1, 5, 9, 13, 17, 21, 25, 29, 33, 37, 41, 45, 49, 53, 57, 61, 65, 73, 77, 81, 85, 89, and 93. In some embodiments, the present invention is directed to a vector or system of vectors containing one or more nucleic acid sequences encoding one or more CDRs of one or more heavy and/or light chains of one or more of the anti-HIV-1 antibodies of the present invention, e.g. nucleotide sequence or sequences coding for one or more of SEQ ID NOs: 2-4, 6-8, 10-12, 14-16, 18-20, 22-24, 26-28, 30-32, 34-36, 38-40, 42-44, 46-48, 50-52, 54-56, 58-60, 62-64, 66-68, 70-72, 74-76, 78-80, 82-84, 86-88, 90-92, and 94-96 and combinations thereof. These nucleotides encoding the heavy/light chains and/or CDRs may have conservative substitutions and for those encoding the CDRs, independent of such conservative substitutions, may share a certain degree of homology (e.g. at least 75%, 80%, 85%, 90%, 95%, 96%, 97%, 98%, or 99%) with the nucleotide sequences. The vector or vector system of the present invention may be introduced into one or more cells (i.e. the cells are "transformed" with the vector), and such means are known within the art.

C. Pharmaceutical Formulations and Delivery

One embodiment of the present invention is directed towards pharmaceutical compositions comprising at least one anti-HIV-1 antibody or antigen-binding portion thereof of the present invention, as well as their methods of use in treating a patient in need thereof. The patient may have a latent or active infection by HIV-1. The anti-HIV-1 antibodies or antigen-binding portions thereof utilized in these compositions and methods may be any anti-HIV-1 antibody or antigen-binding portion thereof of the present invention, but of particular utility are those anti-HIV antibodies or antigen-binding portions thereof that comprise BG18 or variants, including recombinantly produced variants, and/or engineered derivatives thereof.

A pharmaceutically acceptable anti-HIV-1 antibody or antigen-binding portions thereof composition suitable for patient administration will contain an effective amount of the anti-HIV-1 antibody or antibodies or antigen-binding portions thereof in a formulation which both retains biological activity while also promoting maximal stability during storage within an acceptable temperature range. The pharmaceutical compositions can also include, depending on the formulation desired, pharmaceutically acceptable diluents, pharmaceutically acceptable carriers and/or pharmaceutically acceptable excipients, or any such vehicle commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. The amount of an excipient that is useful in the pharmaceutical composition or formulation of this invention is an amount that serves to uniformly distribute the antibody throughout the composition so that it can be uniformly dispersed when it is to be delivered to a subject in need thereof. It may serve to dilute the antibody to a concentration which provides the desired beneficial palliative or curative results while at the same time minimizing any adverse side effects that might occur from too high a concentration. It may also have a preservative effect. Thus, for antibodies having a high physiological activity, more of the excipient will be employed. On the other hand, for any active ingredient(s) that exhibit a lower physiological activity, a lesser quantity of the excipient will be employed.

The pharmaceutically acceptable composition may be in liquid form or solid form. A solid formulation is generally, but not necessarily, lyophilized and brought into solution prior to administration for either single or multiple dosing. The formulations should not be exposed to extreme temperature or pH so as to avoid thermal denaturation. Thus, it is essential to formulate an antibody composition of the present invention within a biologically relevant pH range. A solution buffered to maintain a proper pH range during storage is often necessary, especially for liquid formulations stored for longer periods of time between formulation and administration. Typically, both liquid and solid formulations require storage at lower temperatures (usually 2-8° C.) in order to retain stability for longer periods. Formulated antibody compositions, especially liquid formulations, may contain a bacteriostat to prevent or minimize proteolysis during storage, including but not limited to effective concentrations (usually <1% w/v) of benzyl alcohol, phenol, m-cresol, chlorobutanol, methylparaben, and/or propylparaben. A bacteriostat may be contraindicated for some patients. Therefore, a lyophilized formulation may be reconstituted in a solution either containing or not containing such a component. Additional components may be added to either a buffered liquid or solid antibody formulation, including but not limited to sugars as a cryoprotectant (including but not necessarily limited to polyhydroxy hydrocarbons such as sorbitol, mannitol, glycerol and dulcitol and/or disaccharides such as sucrose, lactose, maltose or trehalose) and, in some instances, a relevant salt (including but not limited to NaCl, KCl or LiCl). Such antibody formulations, especially liquid formulations slated for long term storage, will rely on a useful range of total osmolarity to both promote long term stability at temperature of 2-8° C., or higher, while also making the formulation useful for parenteral injection. For example, but not necessarily, an effective range of total osmolarity (the total number of molecules in solution) may be from about 200 mOs/L to about 800 mOs/L. It will be apparent that the amount of a cyroprotectant, such as sucrose or sorbitol, will depend upon the amount of salt in the formulation in order for the total osmolarity of the solution to remain within an appropriate range. Therefore a salt free formulation may, but not necessarily, contain from about 5% to about 25% sucrose.

Alternatively, a salt free sorbitol-based formulation may, but not necessarily, contain sorbitol within a range from about 3% to about 12%. Salt-free formulations may warrant increased ranges of the respective cryoprotectant in order to maintain effective osmolarity levels. These formulation may also contain a divalent cation (including but not necessarily limited to $MgCl_2$, $CaCl_2$ and $MnCl_2$); and a non-32 ionic surfactant (including but not necessarily limited to Polysorbate-80 (Tween 80®), Polysorbate-60 (Tween 60®), Polysorbate-40 (Tween 40®) and Polysorbate-20 (Tween 20®), polyoxyethylene alkyl ethers, including but not limited to Brij 58®, Brij 35®, as well as others such as Triton X-100®, Triton X 114®, NP40®, Span 85 and the Pluronic series of non-ionic surfactants (e.g., Pluronic 121)). Any combination of such components, including probable inclusion of a bacteriostat, may be useful to fill the antibody-containing formulations of the present invention. The anti-HIV-1 antibodies or antigen-binding portions thereof of the present invention may also be a "chemical derivative", which describes antibodies that contain additional chemical moieties which are not normally a part of the immunoglblulin molecule (e.g., pegylation). Such moieties may improve the solubility, half-life, absorption, etc. of the base molecule. Alternatively the moieties may attenuate undesirable side effects of the base molecule or decrease the toxicity of the base molecule.

For in vivo treatment, the patient is administered or provided a pharmaceutical formulation including at least one anti-HIV antibody or antigen-binding portion thereof of the present invention. When used for in vivo therapy, the anti-HIV antibodies or antigen-binding portions thereof of the invention are administered to the patient in therapeutically effective amounts (i.e., amounts that eliminate or reduce the total viral load, as described in Example 1 infra). The antibodies are administered to a human patient, in accord with known methods, such as intravenous administration, for example, as a bolus or by continuous infusion over a period of time, by intramuscular, intraperitoneal, intracerobrospinal, subcutaneous, intra-articular, intrasynovial, intrathecal, oral, topical, or inhalation routes. The antibodies or antigen-binding portions thereof can be administered parenterally, when possible, at the target cell site, or intravenously. In some embodiments, antibody is administered by intravenous or subcutaneous administration. Therapeutic compositions of the invention may be administered to a patient or subject systemically, parenterally, or locally. The above parameters for assessing successful treatment and improvement in the disease are readily measurable by routine procedures familiar to a physician.

For parenteral administration, the anti-HIV-1 antibodies or antigen-binding portions thereof may be formulated in a unit dosage injectable form (solution, suspension, emulsion) in association with a pharmaceutically acceptable, parenteral vehicle. Examples of such vehicles include, but are not limited to, water, saline, Ringer's solution, dextrose solution, and 5% human serum albumin. Non-aqueous vehicles include, but are not limited to, fixed oils and ethyl oleate. Liposomes can be used as carriers. The vehicle may contain minor amounts of additives such as substances that enhance isotonicity and chemical stability, such as, for example, buffers and preservatives.

The anti-HIV-1 antibodies or antigen-binding portions thereof of the present invention may be administered to the host in any manner, strategy and/or combination available in the art in amounts sufficient to offer a therapeutic treatment against HIV-1. These compositions may be provided to the individual by a variety of routes known in the art, especially parenteral routes, including but in no way limited to parenteral routes such as intravenous (IV), intramuscular (IM); or subcutaneous (SC) administration, with IV administration being the norm within the art of therapeutic antibody administration. These compositions may be administered as separate or multiple doses (i.e., administration of the antibody at staggered times by maintaining the sterile condition of the formulation through the treatment regime).

The dose and dosage regimen depends upon a variety of factors readily determined by a physician, such as the nature of the infection, for example, its therapeutic index, the patient, and the patient's history. Generally, a therapeutically effective amount of an antibody is administered to a patient. In some embodiments, the amount of antibody administered is in the range of about 0.001 mg/kg to about 100 mg/kg of patient body weight, and any range in between. Depending on the type and severity of the infection, about 0.1 mg/kg to about 50 mg/kg body weight (for example, about 0.1-15 mg/kg/dose) of antibody is an initial candidate dosage for administration to the patient, whether, for example, by one or more separate administrations, or by continuous infusion. The anti-HIV-1 antibodies can be delivered relatively low volume rates, for example but not necessarily from about 0.001 ml/day to 10 ml/day so as to minimize tissue disturbance or trauma near the site where the formulation is released. The formulation may be released at a rate of, depending on the specific biological agent(s), at a low dose, e.g., from about 0.01 µg/hr or 0.1 µg/hr, 0.25 µg/hr, 1 µg/hr, generally up to about 200 µg/hr, or the formulation is delivered at a low volume rate e.g., a volume rate of from about 0.001 mL/day to about 1 mL/day, for example, 0.01 micrograms per day up to about 20 milligrams per day. Dosage depends on a number of factors such as potency, bioavailability, and toxicity of the active ingredient used (e.g. the anti-HIV-1 antibodies or antigen-binding portions thereof) and the requirements of the subject. The progress of this therapy is readily monitored by conventional methods and assays and based on criteria known to the physician or other persons of skill in the art. The above parameters for assessing successful treatment and improvement in the disease are readily measurable by routine procedures familiar to a physician.

Specific embodiments for delivery vehicles for anti-HIV-1 antibodies of the present invention include PLGA microspheres, as discussed herein and as further known in the art, as well as polymer-based non-degradable vehicles comprising poly (ethylene-co-vinyl acetate; PEVAc). Additionally, controlled-release and localized delivery of antibody-based therapeutic products is reviewed in Grainger, et al., 2004, *Expert Opin. Biol. Ther.* 4(7): 1029-1044). Suitable microcapsules capable of encapsulating the antibody may also include hydroxymethylcellulose or gelatin-microcapsules and polymethyl methacrylate microcapsules prepared by coacervation techniques or by interfacial polymerization. See PCT publication WO 99/24061 entitled "Method for Producing IGF-1 Sustained-Release Formulations," wherein a protein is encapsulated in PLGA microspheres, this reference which is hereby incorporated herein by reference in its entirety. In addition, microemulsions or colloidal drug delivery systems such as liposomes and albumin microspheres, may also be used. Other preferred sustained-release compositions employ a bioadhesive to retain the antibody at the site of administration. As noted above, the sustained-release formulation may comprise a biodegradable polymer into which the antibody is disposed, which may provide for non-immediate release. Non-injectable devices may be described herein as an "implant", "pharmaceutical depot implant", "depot implant", "non-injectable depot" or some such similar term. Common depot implants may include, but are not limited to, solid biodegradable and non-biodegradable polymer devices (such as an extended polymer or coaxial rod shaped device), as well as numerous pump systems also known in the art. Injectable devices are split into bolus injections (release and dissipation of the drug subsequent to injection), and repository or depot injections, which provide a storage reservoir at the site of injection, allowing for sustained-release of the biological agent over time. A depot implant may be surgically tethered to the point of delivery so as to provide an adequate reservoir for the prolonged release of the antibody over time. Such a device will be capable of carrying the drug formulation in such quantities as therapeutically or prophylactically required for treatment over the pre-selected period. The depot implant may also provide protection to the formulation from degradation by body processes (such as proteases) for the duration of treatment. As known in the art, the term "sustained-release" refers to the gradual (continuous or discontinuous) release of such an agent from the block polymer matrix over an extended period of time. Regardless of the specific device, the sustained-release of the composition will result in a local biologically effective concentrations of the antibody. A sustained release of the biological agent(s) will be for a period of a single day, several days, a week or more; but most likely for a month and more, or up to about six months, depending on the formulation. Natural or synthetic polymers known in the art will be useful as a depot implant due to characteristics such as versatile degradation kinetics, safety, and biocompatibility. These copolymers can be manipulated to modify the pharmacokinetics of the active ingredient, shield the agent from enzymatic attack, as well as degrading over time at the site of attachment or injection. The artisan will understand that there are ample teachings in the art to manipulate the properties of these copolymers, including the respective production process, catalysts used, and final molecular weight of the sustained-release depot implant or depot injection. Natural polymers include but are not limited to proteins (e.g., collagen, albumin or gelatin); polysaccharides (cellulose, starch, alginates, chitin, chitosan, cyclodextrin, dextran, hyaluronic acid) and lipids. Biodegradable synthetic polymers may include but are not limited to various polyesters, copolymers of L-glutamic acid and gamma ethyl-L-glutamate (Sidman et al., 1983, Biopolymers 22:547-556), polylactides ([PLA]; U.S. Pat. No. 3,773,919 and EP 058,481), polylactate polyglycolate (PLGA) such as polylactide-co-glycolide (see, for example, U.S. Pat. Nos. 4,767,628 and 5,654,008), polyglycolide (PG), polyethylene glycol (PEG) conjugates of poly(α-hydroxy acids), polyorthoesters, polyaspirins, polyphosphagenes, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, polyorthoesters (POE), or any combinations thereof, as described above (see, for example, U.S. Pat. No. 6,991, 654 and U.S. Pat. Appl. No. 20050187631, each of which is incorporated herein by reference in its entirety, hydrogels (see, for example, Langer et al., 1981, J. Biomed. Mater. Res. 15:167-277; Langer, 1982, Chem. Tech. 12:98-105, non-degradable ethylene-vinyl acetate (e.g. ethylene vinyl acetate disks and poly(ethylene-co-vinyl acetate)), degradable lactic acid-glycolic acid copolyers such as the Lupron Depot™, poly-D-(−)-3-hydroxybutyric acid (EP 133,988), hyaluronic acid gels (see, for example, U.S. Pat. No. 4,636, 524), alginic acid suspensions, polyorthoesters (POE), and the like. Polylactide (PLA) and its copolymers with glycolide (PLGA) have been well known in the art since the commercialization of the Lupron Depot™, approved in 1989 as the first parenteral sustained-release formulation utilizing PLA polymers. Additional examples of products which utilize PLA and PLGA as excipients to achieve sustained-release of the active ingredient include AMIDOX (PLA; periodontal disease), NUTROPIN DEPOT (PLGA; with hGH), and the TRELSTAR DEPOT (PLGA; prostate cancer). Other synthetic polymers included but are not limited to poly(c-caprolactone), poly3-hydroxybutyrate, poly(β-malic acid) and poly(dioxanone)]; polyanhydrides, polyurethane (see WO 2005/013936), polyamides, cyclodestrans, polyorthoesters, n-vinyl alcohol, polyethylene oxide/polyethylene terephthalate, polyphosphate, polyphosphonate, polyorthoester, polycyanoacrylate, polyethylenegylcol, polydihydropyran, and polyacytal. Non-biodegradable devices include but are not limited to various cellulose derivatives (carboxymethyl cellulose, cellulose acetate, cellulose acetate propionate, ethyl cellulose, hydroxypropyl methyl cellulose) silicon-based implants (polydimethylsiloxane), acrylic polymers, (polymethacrylate, polymethylmethacrylate, polyhydroxy(ethylmethylacrylate), as well as polyethylene-co-(vinyl acetate), poloxamer, polyvinylpyrrolidone, poloxamine, polypropylene, polyamide, polyacetal, polyester, poly ethylene-chlorotrifluoroethylene (PTFE or "Teflon™"), styrene butadiene rubber, polyethylene, polypropylene, polyphenylene oxide-polystyrene, poly-a-chloro-p-xylene, polymethylpentene, polysulfone and other related biostable polymers. Carriers suitable for sustained-release depot formulations include, but are not limited to, micospheres, films, capsules, particles, gels, coatings, matrices, wafers, pills or other pharmaceutical delivery compositions. Examples of such sustained-release formulations are described above. See also U.S. Pat. Nos. 6,953,593; 6,946, 146; 6,656,508; 6,541,033; and 6,451,346, the contents of each which are incorporated herein by reference. The dosage form must be capable of carrying the drug formulation in such quantities and concentration as therapeutically required for treatment over the pre-selected period, and must provide sufficient protection to the formulation from degradation by body processes for the duration of treatment. For example, the dosage form can be surrounded by an exterior made of a material that has properties to protect against degradation from metabolic processes and the risk of, e.g., leakage, cracking, breakage, or distortion. This can prevent expelling of the dosage form contents in an uncontrolled manner under stresses it would be subjected to during use, e.g., due to physical forces exerted upon the drug release device as a result of normal joint articulation and other movements by the subject or for example, in convective drug delivery devices, physical forces associated with pressure generated within the reservoir. The drug reservoir or other means for holding or containing the drug must also be of such material as to avoid unintended reactions with the active agent formulation, and is preferably biocompatible (e.g, where the dosage form is implanted, it is substantially non-reactive with respect to a subject's body or body fluids). Generally, the anti-HIV-1 antibodies are administered to an individual for at least 12 hours to at least a week, and most likely via an implant designed to deliver a drug for at least 10, 20, 30, 100 days or at least 4 months, or at least 6 months, 12 months, 24 months or more, as required.

In some embodiments, the anti-HIV-1 antibodies or antigen-binding portions thereof of the present invention may be co-administered with one or more additional treatments for HIV-1, e.g. co-administered with one or more HIV agents (e.g. non-nucleoside reverse transcriptase inhibitors (NNRTTs), nucleoside reverse transcriptase inhibitors (NRTTs), protease inhibitors (PIs), fusion inhibitors, CCR5 antagonists/entry inhibitors, integrase strand transfer inhibitors (INSTIs), and combinations thereof) and/or additional anti-HIV-1 antibodies or antigen-binding portions thereof, including but not limited to additional anti-HIV-1 antibodies or antigen-binding portions thereof of the present invention. As shown in Example 1 infra, a 1:1:1 administration of NC17, BG1, and BG18 was effective to reduce viral load in vivo. While not wishing to be bound by theory, the data indicates that monoclonal bNAbs and very low levels of neutralization sensitive viruses co-exist in EB354 suggesting that antibodies contribute to elite control in this individual. According to another embodiment, the present invention provides a passive vaccine or pharmaceutical compositions containing at least one anti-HIV-1 antibody or antigen-binding portions thereof of the invention and a pharmaceutically acceptable carrier. According to one embodiment, the vaccine or pharmaceutical compositions is a composition containing at least one antibody described herein and a pharmaceutically acceptable excipient. The vaccine can include a plurality of the antibodies having the characteristics described herein in any combination and can further include other anti-HIV-1 antibodies or antigen-binding portions thereof. The passive vaccine may comprise one or more pharmaceutically acceptable preservatives, carriers, and/or excipients, which are known in the art. In other embodiments, the present invention provides an active vaccine or pharmaceutical compositions containing HIV-1 or an antigenic fragment thereof. If HIV-1 is used, it may be attenuated. It may be heat-killed. If antigenic fragments are utilized, it may be preferable, although not necessary, to use glycoprotein gp120, although fragments of glycoprotein gp120 may be acceptable.

The present compositions may be used in an immunogenic composition to immunize an animal. Such immunogenic composition according to the invention may be used for the preparation of a vaccine. Preferably a prophylactic and/or therapeutic vaccine is produced. Thus, within the scope of this invention is an immunogenic or vaccine composition that contains a pharmaceutically acceptable carrier and an effective amount of an antigen as described supra. The carriers used in the composition can be selected on the basis of the mode and route of administration, and standard pharmaceutical practice. The composition can also contain an adjuvant. Examples of an adjuvant include a cholera toxin, *Escherichia coli* heat-labile enterotoxin, liposome, unmethylated DNA (CpG) or any other innate immune-stimulating complex. Various adjuvants that can be used to further increase the immunological response depend on the host species and include Freund's adjuvant (complete and incomplete), mineral gels such as aluminum hydroxide, surface-active substances such as lysolecithin, pluronic polyols, polyanions, peptides, oil emulsions, keyhole limpet hemocyanin, and dinitrophenol.

A vaccine formulation may be administered to a subject per se or in the form of a pharmaceutical or therapeutic composition. Compositions of the invention and an adjuvant may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the antigens of the invention into preparations which can be used pharmaceutically. Proper formulation is dependent upon the route of administration chosen.

For injection, vaccine preparations may be formulated in aqueous solutions, preferably in physiologically compatible buffers such as Hanks' solution, Ringer's solution, phosphate buffered saline, or any other physiological saline buffer. The solution may contain formulatory agents such as suspending, stabilizing and/or dispersing agents. Alternatively, the composition may be in powder form for constitution with a suitable vehicle, e.g., sterile pyrogen-free water, before use.

The amount of a composition administered depends, for example, on the particular antigen in the composition, whether an adjuvant is co-administered with the antigen, the type of adjuvant co-administered, the mode and frequency of administration, and the desired effect (e.g., protection or treatment), as can be determined by one skilled in the art. Determination of an effective amount of the vaccine formulation for administration is well within the capabilities of those skilled in the art, especially in light of the detailed disclosure provided herein. An effective dose can be estimated initially from in vitro assays. For example, a dose can be formulated in animal models to achieve an induction of an immune response using techniques that are well known in the art. One having ordinary skill in the art could readily optimize administration to all animal species based on results described herein. Dosage amount and interval may be adjusted individually. For example, when used as a vaccine, the vaccine formulations of the invention may be administered in about 1 to 3 doses for a 1-36 week period. Vaccination may continue indefinitely depending on the circumstances, particularly with passive vaccination. Preferably, 1 or 2 doses are administered, at intervals of about 3 weeks to about 4 months, and booster vaccinations may be given periodically thereafter. Alternative protocols may be appropriate for individual animals. A suitable dose is an amount of the vaccine formulation that, when administered as described above, is capable of raising an immune response in an immunized animal sufficient to protect the animal from an infection for at least 4 to 12 months. In general, the amount of the antigen present in a dose ranges from about 1 pg to about 100 mg per kg of host, typically from about 10 pg to about 1 mg, and preferably from about 100 pg to about 1 pg. Suitable dose range will vary with the route of injection and the size of the subject, but will typically range from about 0.1 mL to about 5 mL. Additional boosters can be given as needed.

D. Kits and Diagnostic Methods

One embodiment of the present invention is directed to kits for detecting HIV-1 present in a sample. These kits may comprise an anti-HIV-1 antibody or antigen-binding portion thereof of the present invention and various reagents, for example, reagents that aid in detection of binding between the anti-HIV-1 antibody and an epitope present on HIV-1, e.g. gp120 and/or gp140, or an antigenic fragment thereof.

The kits may be in vitro assays, such as immunoassays, e.g. enzyme immune assays (EIA), enzyme linked immunosorbent assay (ELISA), ELISPOT (enzyme-linked immunospot), radioimmunoassays (RIAs), immunofluorescence, and other assays known in the art, including but not limited to Western Blot analysis and/or immunoprecipitation methods. The in vitro assays may be competitive, or indirect, such as in a sandwich assay, or may be an antibody capture method. For example in a direct ELISA, a buffered solution of an antigen, e.g. a sample containing HIV-1 or an antigenic fragment thereof or a biological sample containing or suspected of containing HIV-1, is added to a well of a microtiter plate, e.g. a 96-well plate. A solution of non-reacting protein, e.g. bovine serum albumin or casein is then added to the well. The anti-HIV-1 antibody or antigen-binding portions thereof conjugated to a reporter molecule enzyme is added, e.g. conjugated to horse-radish peroxidase, although that is not necessarily the enzyme, as other common enzymes include alkaline phosphatase, or β-D-galactosidase, although other enzymes are conceivable and considered embodied by the present invention. A substrate for the enzyme is then added, which leads to a detectable signal. For example, adding TMB to horseradish peroxidase leads to a colored product, in which case the ELISA is a colorimetric assay. ELISAs may be run in a qualitative or quantitative format. Qualitative results provide a simple positive or negative result (yes or no) for a sample. The cutoff between positive and negative is determined by the analyst and may be statistical. Sandwich ELISAs generally follow the following protocol. Capture anti-HIV-1 antibody or antigen-binding portions thereof is bound to (i.e. "immobilized") on a substrate, e.g. a mictotiter plate. Antigen-containing sample (i.e. sample containing HIV-1 or an antigenic fragment thereof, is then added to the substrate at which point it is captured by the anti-HIV-1 antibodies. The substrate is then washed to remove unbound antigen. A second anti-HIV-1 antibody or antigen-binding portions thereof is added, which binds to a different epitope on HIV-1, such as different epitopes on gp120, or on different antigens, such as gp140. The second anti-HIV-1 antibody or antigen-binding portions thereof is bound to a reporter molecule, e.g. an enzyme, although the reporter molecule may be any molecule which leads to a detectable signal. The plate may be washed a second time, and in those instances where the reporter molecule is an enzyme, a substrate may be added, e.g. TMB, that results in a detectable signal (also a colorimetric assay). A third type of common ELISA is competitive ELISA. In these embodiments, unlabeled anti-HIV-1 antibody or antigen-binding portions thereof is incubated in the presence of an antigen-containing sample which are then added to an antigen-coated well. The plate is washed so as to remove unbound antibodies. A secondary antibody that is specific to the primary antibody, e.g. a secondary antibody specific to anti-HIV-1 antibodies. The secondary antibody is bound to a reporter molecule, as described herein, such as an enzyme (or any other molecule that may lead to a detectable signal). Some competitive ELISA utilize labeled antigens rather than labeled antibodies; the less antigen in the sample, the more labeled antigen is retained and the stronger a detectable signal results.

Other forms of common in vitro assays include radioimmunoassays (RIAs). Typically a known quantity of an antigen is linked to a radioactive tracer, e.g. I-125 although others are suitable for use, such as $^{99}$Tc, which is then mixed with a known amount of antibody specific for the antigen, e.g. anti-HIV-1 antibodies or antigen-binding portions thereof. Then, a sample containing unknown quantity of an antigen is added, (e.g. a biological sample that contains or is suspected of containing HIV-1 or an antigenic fragment thereof) is added. This is a direct competitive for specific binding; as the concentration of unlabeled antigen is increased, the binding between the anti-HIV-1 antibodies and the labeled standard is decreased, which is directly measurable by measuring radioactivity. Other assays are known and a person of ordinary skill in the art would readily recognize their applicability.

In some embodiments, the invention is directed to a method of detecting HIV-1 or an antigenic fragment thereof in a sample. Such methods may utilize any of the assays described herein, or others that are known in the art. Several of the assays described herein are capable of quantifying the amount of antigen present in a sample, and so accordingly, in some embodiments, the present invention is directed to methods of quantifying the amount of HIV-1 or antigenic fragments thereof present in a sample, e.g. a biological sample.

The assays containing anti-HIV-1 antibodies or antigen-binding portions thereof of the present invention may or may not be utilized for diagnostic purposes. Accordingly, in some embodiments, the invention is directed to methods of diagnostic use of the anti-HIV-1 antibodies or antigen-binding portions thereof of the present invention. Because of the specificity of the anti-HIV-1 antibodies or antigen-binding portions thereof of the present invention, immunoassays containing anti-HIV-1 antibodies or antigen-binding portions thereof of the present invention may be sufficient to diagnose an individual as having an active or latent infection of HIV-1. The antibodies or antigen-binding portions thereof need not be restricted to any particular epitopes, so long as the antibodies or antigen-binding portions thereof used are specific to HIV-1. For example, in a sandwich assay, the first anti-HIV-1 antibody or antigen-binding portions thereof may bind to a first epitope, such as on gp120, and the second anti-HIV-1 antibody or antigen-binding portions thereof (which is bound to a reporter molecule) may bind to a second epitope, which may or may not be present on the same antigen. Accordingly, kits and methods used to detect or quantify the amount of HIV-1 or an antigenic fragment thereof may contain BG18, NC37, and BG1, including antigen-binding portions thereof, and would be considered within the scope of this invention. Or, any of BG18, NC37, and BG1, including antigen-binding portions thereof, and any other anti-HIV-1 antibody, so long as they are suitable for incorporation into such kits/methods. One will appreciate that the anti-HIV-1 antibodies or antigen-binding portions thereof used for purposes of detecting and/or quantifying HIV-1 present in a sample or even for diagnostic purposes do not necessarily need to be capable of broadly neutralizing HIV-1 to possess utility for such purposes.

E. Equivalents

Where a value of ranges is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference in their entireties.

As used herein and in the appended claims, the singular forms "a", "and" and "the" include plural references unless the context clearly dictates otherwise.

The term "about" refers to a range of values which would not be considered by a person of ordinary skill in the art as substantially different from the baseline values. For example, the term "about" may refer to a value that is within 20%, 15%, 10%, 9%, 8%, 7%, 6%, 5%, 4%, 3%, 2%, 1%, 0.5%, 0.1%, 0.05%, or 0.01% of the stated value, as well as values intervening such stated values.

Publications disclosed herein are provided solely for their disclosure prior to the filing date of the present invention. Nothing herein is to be construed as an admission that the present invention is not entitled to antedate such publication by virtue of prior invention. Further, the dates of publication provided may be different from the actual publication dates which may need to be independently confirmed.

Each of the applications and patents cited in this text, as well as each document or reference, patent or non-patent literature, cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference in their entirety. More generally, documents or references are cited in this text, either in a Reference List before the claims; or in the text itself; and, each of these documents or references ("herein-cited references"), as well as each document or reference cited in each of the herein-cited references (including any manufacturer's specifications, instructions, etc.), is hereby expressly incorporated herein by reference.

The following non-limiting examples serve to further illustrate the present invention.

EXAMPLES

1. Co-Existence of Potent HIV-1 Broadly Neutralizing Antibodies and Antibody-Sensitive Viruses in a Virenuc Controller A. Methods HIV-1-Infected Subject EB354

Purified IgG from donor EB354 ranked in the top 1% for neutralization breadth and potency in a cohort of 394 HIV-1 infected long-term non-progressors. Donor EB354 was diagnosed with HIV-1 Clade B in 1986. He received treatment with didanosine and stavudine between 1995 and 1998, but has had no antiretroviral therapy since that time. He has been clinically followed frequently since 2002 (Table 3: HLA A*01:01, 24:02, B*27:05, 57:01, C*01:02, 06:02). Most individuals rapidly develop strain specific antibodies shortly after infection. This response is associated with selection for resistant viral variants that in some cases elicit bNAbs. However, the individuals studied in detail differ from EB354 in that the development of bNAbs is associated with rapid selection of autologous plasma viruses, which are resistant to co-existing bNAbs. EB354 is significant because sensitive and resistant viral strains co-exist with bNAbs and the resistant strains fail to produce high levels of viremia either because they are in some way partially effective or kept in check by CD8+ T cells. Thus the bNAb sensitive plasma viruses were unable to escape immune pressure in this individual, resulting in bNAb:virus equilibrium, where the virus persists, but is incapable of producing high levels of viremia. EB354 is unusual in being both an elite controller and elite neutralizer. HIV-1 elite controllers are infected individuals that maintain low viral loads for many years. These individuals are less likely to transmit the virus and they maintain long-term AIDS-free survival. HLA alleles B57*01 and/or B27*05 are found in 85% of HIV-1 elite controllers. These alleles are associated with enhanced CD8 T cell cytotoxic activity. Compared to viremic progressors (i.e., patients with high viral loads), elite controllers are less likely to develop bNAbs. Irrespective of robust CD8+ T cell responses that may have partially controlled infection, there was sufficient HIV-1 replication in EB354 to support bNAb development and affinity maturation. As discussed herein, the bNAbs that account for serologic neutralizing activity in donor EB354 recognize several non-overlapping epitopes.

TABLE 3

Clinical information regarding donor EB354

| diagnosis date | 1986 | | |
|---|---|---|---|
| HLA | A101, 2402 | B2705, 5701 | Cw102, 602 |
| visit date | Viral Load | CD4abs | CD8abs |
| Apr. 24, 2002 | 310 | 957 | 1406 |
| Aug. 7, 2002 | 653 | 554 | |
| Dec. 3, 2002 | 2520 | 983 | 1787 |
| Mar. 11, 2004 | 1035 | 1323 | 1634 |
| Jun. 18, 2004 | 171 | 1231 | 1753 |
| Aug. 20, 2004 | 467 | | |
| Oct. 7, 2004 | 182 | 789 | |
| Feb. 28, 2005 | 1048 | 1227 | |
| Aug. 25, 2005 | <400 | 1080 | |
| Nov. 17, 2005 | 1665 | 1551 | |
| Aug. 3, 2006 | <400 | | |
| Oct. 24, 2006 | <400 | 744 | 1132 |
| Nov. 15, 2006 | 206 | 814 | |
| Apr. 6, 2007 | <400 | 564 | |
| Nov. 28, 2007 | <400 | 781 | |
| Jul. 17, 2008 | 149 | 815 | |
| Mar. 17, 2009 | 107 | 734 | |
| Feb. 19, 2010 | 170 | 900 | 1933 |
| Aug. 10, 2010 | 65 | 1096 | 1706 |
| Jul. 13, 2011 | 380 | 795 | 1512 |
| Mar. 28, 2013 | 414 | 1127 | 1809 |
| Sep. 18, 2013 | 547 | 674 | 1152 |
| Jul. 21, 2014 | 454 | 697 | 1321 |
| Jul. 17, 2015 | 461 | 605 | 1224 |

B Cell Sorting and Antibody Isolation

Single-cell sorting of bait+CD19+IgG+ B cells from donor EB354 PBMCs was conducted as described in J. F. Scheid et al., A method for identification of HIV gp140 binding memory B cells in human blood. *Journal of immunological methods* 343, 65-67 (2009). Memory B cells were pre-enriched with anti-CD19 magnetic beads (MACS) and stained using four different baits: the gp120 2CC core protein as bait, gp140YU2, a 1:1 mixture of gp140$_{92\ UG37.8}$ (Clade A)+gp140$_{CZA79012}$ (Clades C) and BG505 SOSIP.664. Rescue primers were used to amplify both heavy chains and Igλ genes and regular primers were used for IgK chain. All PCR products were sequenced and analyzed for Ig gene usage, CDR3, and the number of $V_H/V_L$ somatic hypermutations (IgBLAST and IMGT). Purified, digested PCR products were cloned into human Igγ1-, Igκ or Igλ-expression vectors as previously described in T. Tiller et al., Efficient generation of monoclonal antibodies from single human B cells by single cell RT-PCR and expression vector cloning. *Journal of immunological methods* 329, 112-124 (2008) and produced by transient transfection of IgH, IgK and IgL expression plasmids into exponentially growing HEK 293-6E cells as described in F. Klein et al., Enhanced HIV-1 immunotherapy by commonly arising antibodies that target virus escape variants. *The Journal of experimental medicine* 211, 2361-2372 (2014).

Neutralization Studies

HIV-1 neutralization was evaluated using the luciferase-based TZM.bl cell assay. Briefly, envelope pseudoviruses were incubated with fivefold serial dilutions of single antibodies and applied to TZM.bl cells that carry a luciferase reporter gene. After 48 hours, cells were lysed and luminescence was measured. $IC_{50}$ and $IC_{80}$ reflect single antibody concentrations that caused a reduction in relative luminescence units (RLU) by 50% and 80%, respectively. Coverage curves were built using the Antibody Database computational tool.

Crystallization, X-ray Data Collection and Structure Determinations

Crystals of BG18 Fab in which a potential A-linked glycosylation site at heavy chain position 26 was removed by mutating Asn26HC to Gln showed superior size and morphology compared with crystals of wild-type BG18 Fab, thus the structure determination was done using BG18$_{N26Q}$ Fab. Crystals of BG18$_{N26Q}$ Fab (space group P2$_1$; a=46.12 Å, b=71.04 Å, c=69.54 Å; β=98.48°; 1 molecule per asymmetric unit) were obtained by combining 0.2 μL of an 18 mg/mL protein solution with 0.2 mL of 0.1 M sodium acetate pH 4.5, 26.8% (v/v) polyethylene glycol (PEG) 400 and 13.4% (w/v) PEG 8,000 at 20° C., cryoprotected in mother liquor supplemented with 20% (v/v) ethylene glycol, and flash cooled in liquid nitrogen. Crystals of NC102 Fab (space group P2$_1$2$_1$2$_1$; a=60.2 Å, b=82.5 Å, c=117.2 Å; 1 molecule per asymmetric unit) were produced by vapor diffusion in sitting drops with a reservoir of 0.1 M sodium acetate trihydrate pH 4.6 and 2.0 M ammonium sulfate using 250 nL drops with a 1.5:1 protein:reservoir ratio. Crystals were cryoprotected in mother liquor supplemented with 25% (v/v) ethylene glycol and flash cooled in liquid nitrogen. Crystals of a NC37-93TH057 complex (space group P2$_1$2$_1$2$_1$; a=63.6 Å, b=67.4 Å, c=210.4 Å; 1 complex per asymmetric unit) were produced by vapor diffusion in 250 nL sitting drops by incubating protein and reservoir (comprising 0.1 M HEPES pH 7.5 and 20% (w/v) PEG 10,000) at a 1.5:1 protein:reservoir ratio. Crystals were cryoprotected in mother liquor supplemented with 20% (w/v) PEG 400 and flash cooled in liquid nitrogen.

X-ray diffraction data were collected at the Stanford Synchrotron Radiation Lightsource beamline 12-2 outfitted with a Pilatus 6M pixel detector (Dectris). XDS was used to index, integrate and scale the data. Crystals of BG18$_{N26Q}$ Fab diffracted to 1.5 Å, and the structure was solved by molecular replacement using 10-1074 Fab (PDB code 4FQ2) $V_HV_L$ with CDR loops removed and $C_H1C_L$ as search models. The structure was refined using an iterative approach of refinement with Phenix and manual model building in Coot. The final model of BG18$_{N26Q}$ Fab ($R_{work}$=18.0%, $R_{free}$=18.9%) had 98.3%, 1.7% and 0% of residues in the favored, allowed, and disallowed regions, respectively, of the Ramachandran plot. NC102 Fab diffracted to 1.6 Å, and the structure was solved by molecular replacement using a model of NIH45-46 (PDB code 3U7W) with $V_H V_L$ with CDR loops removed and $C_H 1 C_L$ as search models. The final model of NC102 Fab ($R_{work}$=18.0%, $R_{free}$=20.0%) had 98%, 2% and 0% of residues in the favored, allowed, and disallowed regions, respectively, of the Ramachandran plot. The NC37-93TH057 gp120 complex structure was solved by molecular replacement using search models of NC102 $V_H V_L$, $C_H 1 C_L$, and a truncated gp120 core (from PDB 3U7Y) as search models. The final model of the NC37-93TH057 complex ($R_{work}$=21.0%, $R_{free}$=26.0%) had 96%, 4% and 0% of residues in the favored, allowed, and disallowed regions, respectively, of the Ramachandran plot. Data collection and refinement statistics are presented in Table 4.

picked using swarm picking in EMAN2.1, and the CTF correction was done using EMAN2.1. Initial reference-free 2D class averaging was performed using RELION and all particles were sorted into 250 classes. 9,827 particles corresponding to good class averages were selected, and the particles were further sorted using 3D classification in RELION, after which 7,925 particles were selected for refinement. To obtain a reference structure for 3D classification and refinement, data was collected from an independent BG505 SOSIP.664-BG18-179NC75 complex sample by cryoelectron tomography and a 40 Å sub-tomogram averaged structure was obtained using methods described in Scharf, L., el al., Broadly Neutralizing Antibody 8ANC195 Recognizes Closed and Open States of HIV-1 Env. *Cell* 2015. 162(6): p. 1379-90. The sub-tomogram averaged structure was low-pass filtered to 80 Å for use as the reference structure for single particle reconstruction. The resolution of the final single particle reconstruction was ~25 Å calculated using RELION and a gold-standard FSC with a 0.143 cutoff, recommended for resolution estimations for single particle EM reconstructions.

TABLE 4

Data collection and refinement statistics.

|  | 354BG18 Fab | 354NC37 + 93TH057 | 354NC102 Fab |
|---|---|---|---|
| Resolution range (Å) | 35.44-1.3 (1.346-1.3) | 38.6-2.7 (2.8-2.7) | 38.91-1.60 (1.66-1.60) |
| Space group | $P2_1$ | $P2_1 2_1 2_1$ | $P2_1 2_1 2_1$ |
| Unit cell dimensions |  |  |  |
| a, b, c (Å) | 46.12, 71.04, 69.54 | 63.60, 67.41, 210.42 | 60.22, 82.50, 117.21 |
| a, b, g (°) | 90, 98.48, 90 | 90, 90, 90 | 90, 90, 90 |
| Total reflections | 634239 (60770) | 172153 (17052) | 515918 (48175) |
| Unique reflections | 106792 (10428) | 25596 (2517) | 77546 (7649) |
| Multiplicity | 5.9 (5.7) | 6.7 (6.8) | 6.7 (6.3) |
| Completeness (%) | 0.98 (0.98) | 1.00 (1.00) | 1.00 (1.00) |
| Mean I/sigma (I) | 14.48 (0.86) | 14.80 (2.73) | 11.12 (1.68) |
| Wilson B-factor (Å$^2$) | 14.92 | 41.63 | 15.84 |
| R-merge | 0.06152 (1.772) | 0.1272 (0.7028) | 0.108 (1.031) |
| CC1/2 | 0.999 (0.318) | 0.996 (0.832) | 0.997 (0.996) |
| CC* | 1 (0.694) | 0.999 (0.953) |  |
| $R_{work}$ | 0.180 | 0.21 | 0.18 |
| $R_{free}$ | 0.189 | 0.26 | 0.2 |
| Number of atoms | 3616 | 6161 | 4159 |
| macromolecules | 3167 | 5924 | 3402 |
| ligands |  | 235 | 25 |
| solvent | 449 | 2 | 732 |
| Protein residues | 432 | 781 | 448 |
| RMS (bonds) (Å) | 0.009 | 0.005 | 0.007 |
| RMS (angles) (°) | 1 | 0.96 | 1.145 |
| Clashscore | 6.17 | 13.99 | 3.41 |
| Average B-factor (Å$^2$) | 22.89 | 36.55 | 20.37 |
| macromolecules | 21.3 | 35.77 | 17.77 |
| ligands |  | 56.03 | 34.45 |
| solvent | 34.17 | 34.8 | 31.96 |

Statistics for the highest-resolution shell are shown in parentheses.

The structure of a BG505 SOSIP.664-BG18-179NC75 complex was solved by cryo-electron tomography/sub-tomogram averaging to ~40 Å resolution and used as a reference structure to solve a single particle EM structure from negatively-stained samples. Purified BG505 SOSIP.664-BG18-179NC75 complexes were diluted to 10 µg/mL in TBS immediately before adding 3 µL to a glow-discharged ultrathin C film on holey carbon support film, 400 mesh, Cu grids (Ted Pella, Inc.). Samples on the grids were cross-linked using glutaraldehyde vapor and then stained with 3% uranyl acetate. Data were collected using a FEI Tecnai T12 transmission electron microscope operating at 120 keV equipped with a Gatan Ultrascan 2k×2 k CCD. Images were acquired using a 0.5 second exposure time at a nominal magnification of 42,000× at 1 µm defocus, resulting in 2.5 Å per pixel. A total of 25,639 particles were Fitting of EM Density Maps EM structures were visualized using USCF Chimera. Coordinates from crystal structures were fit into the sub-tomogram averaged or negative stain single particle EM structures using the fit in map utility within UCSF Chimera with the following options: real-time correlation/average update, use map simulated from atoms, resolution 25 Å. A BG505 SOSIP.664 structure (PDB 4TVP) was first fitted into the density, and then coordinates for BG18 Fab and CH103 Fab (PDB 4JAM; as a model for 179NC75 Fab) into corresponding densities individually. The $C_H 1$-$C_L$ domain regions of the Fabs exhibited poor densities.

Protein Production and Purification for Structural Determination Studies

6x-His-tagged BG18, BG18$_{N26Q}$, NC102, and NC37 Fabs were expressed by transient transfection in HEK293-6E cells and purified from transfected cell supernatants using Ni2+-NTA affinity chromatography (GE Healthcare) and Superdex 200 16/60 size exclusion chromatography (SEC) (GE Healthcare). Truncated, His-tagged 93TH057 gp120 core protein was produced in baculovirus-infected insect cells and purified as described using Ni$^{2+}$ affinity chromatography (GE Healthcare) (Diskin et al. *Science* 2011; Diskin et al. NSMB 2010). Prior to crystallization trials, purified NC37 and 93TH057 proteins were coincubated (2:1 molar ratio of Fab to gp120 core) and treated with 5 kU of Endoglycosidase H per mg of gp120 protein for 3 hours at 25° C. Endoglycosidase H-treated complex was purified by size exclusion chromatography using a Superdex 200 10/300 GL column (GE Healthcare).

Soluble BG505 SOSIP.664 trimers for EM studies were constructed as described in Sanders, R. W., et al., A next-generation cleaved, soluble HIV-1 Env trimer, BG505 SOSIP.664 gp140, expresses multiple epitopes for broadly neutralizing but not non-neutralizing antibodies. *PLoS Pathog*, 2013. 9(9): p. e1003618. HEK293-6E cells treated with 5 µM kifunensine (Sigma) were co-transfected with plasmids encoding BG505 SOSIP.664 and soluble furin at a ratio of 4:1. BG505 SOSIP.664 protein was harvested from cell supernatants using a 2G12 immunoaffinity column made by covalently coupling 2G12 IgG monomer to an NHS-activated Sepharose column (GE Healthcare). Protein was eluted with 3M MgCb followed by immediate buffer exchange into Tris-buffered saline (TBS) pH 7.4 (50 mM NaCl). Trimers were further purified using Mono Q 5/50 GL (GE Healthcare) followed by Superose 6 10/300 SEC (GE Healthcare).

Autologous Viruses

Single genome sequencing (SGS) of HIV-1 env genes HIV-1-RNA was extracted from patient plasma using the Qiagen MinElute Virus Spin Kit according to manufacturer's instructions. Extracted RNA was subjected to Env specific cDNA Synthesis using Superscript III Reverse Transcriptase and HIV-1 specific primer envB3out:

```
envB5out:
                              (SEQ ID NO: 97)
5'-TAGAGCCCTGGAAGCATCCAGGAAG-3' envB3out:
                              (SEQ ID NO: 98)
5'-TTGCTACTTGTGATTGCTCCATGT-3' envB5in:
                              (SEQ ID NO: 99)
5'-TTAGGCATCTCCTATGGCAGGAAGAAG-3' envB3in:
                              (SEQ ID NO: 100)
5'-GTCTCGAGATACTGCTCCCACCC-3'
```

First round PCR was performed in a 20 µL volume containing 1× High Fidelity buffer, 2 mM MgSO4, 0.2 mM dNTPs and 0.5 units of High Fidelity Platinum Taq using 0.2 µM each of primers envB5out and envB3out. Second round PCR was performed using 1 µL of PCR 1 and 0.2 µM of primers of envB5in and envB3in. PCR conditions were the same as PCR-1 except for 45 cycles and an increased annealing temperature of 58° C. PCR-2 products were checked using 1% 96-well E-Gels (Invitrogen). Bands from PCRs with amplification efficiencies lower than 30% were subjected to library preparation and sequenced using the Illumina Nextera DNA Sample Preparation Kit (Illumina). CMV-Env expression cassettes were generated according to protocol set forth in J. L. Kirchherr et al., High throughput functional analysis of HIV-1 env genes without cloning. *J Virol Methods* 143, 104-111 (2007). 500 ng of CMV-env were co-transfected with pSG3 Δenv in 6-well plates into 293T cells and supernatant was harvested after 48 hours. All plasmids were sequence validated before expression. Supernatants were subjected to neutralization testing by TZM-bl assays.

TZM-bl Assays of Env Glycol-Mutant Viruses

Pseudoviruses were generated by transfection of 293T cells (ATCC) with an HIV-1 Env expressing plasmid and the Env-deficient genomic backbone plasmid called pSG3 ΔEnv as described in Li, M., et al., Human immunodeficiency virus type 1 env clones from acute and early subtype B infections for standardized assessments of vaccine-elicited neutralizing antibodies. *J Virol*, 2005. 79(16): p. 10108-25. Pseudoviruses were harvested 72 hours post-transfection for use in neutralization assays. Neutralizing activity was assessed using a single round of replication pseudovirus assay and TZM-B1 target cells, as described in Li et al. above. Briefly, TZM-bl cells were seeded in a 96-well flat bottom plate. To this plate was added pseudovirus, which was pre-incubated with serial dilutions of antibody for 1 hour at 37° C. Luciferase reporter gene expression was quantified 72 hours after infection upon lysis and addition of Bright-Glo™ Luciferase substrate (Promega). To determine IC$_{50}$ values, dose-response curves were fit by nonlinear regression.

Synthesis of the HIV-1 V3 Glycopeptides

The synthesis of the V3 glycopeptides derived from several HIV-1 strains was achieved by using a chemoenzymatic method that consisting of automated solid-phase peptide synthesis of the GlcNAc-peptide precursor and subsequent enzymatic transglycosylation of the GlcNAc-peptide to provide the target glycopeptides, following the procedures set forth in Amin, M. N., et al, Synthetic glycopeptides reveal the glycan specificity of HIV-neutralizing antibodies. *Nat Chem Biol*, 2013. 9(8): p. 521-6. The interactions between the biotinylated synthetic glycopeptides and the BG18 and BG8 IgG antibodies were evaluated by SPR using a BIAcore T200 system (GE Healthcare) at 25° C. Biotinylated glycopeptides were immobilized on neutravidin-coated CM5 sensor chips in HBS-P buffer (10 mM HEPES, 150 mM NaCl, P20 surfactant 0.05% v/v, pH 7.4) until 200 response unit (RU) was achieved. BG18 (or BG8) was injected at two-fold series dilutions of concentration starting at 4 µM in BS-P buffer with a flow rate of 40 µL/min. for 180 s. BS-P buffer with a flow rate of 40 µL/min was then injected for 1210s to allow for dissociation. Regeneration was performed by injection of 3M MgCh with a flow rate of 50 µL/min. for 3 minutes followed by injection of HBS-P buffer with a flow rate of 50 µL/min. for 5 minutes.

In vivo Mouse Model

Humanized NOD Rag1$^{-/-}$Il2rg$^{null}$ (NOD.Cg-Rag1$^{tm1Mom}$ Il2rg$^{tm1Wjl}$/SzJ) mice (The Jackson Laboratory) were treated with 1 mg of each antibody sub-cutaneously (s.c.) twice a week for a period of 3 weeks, getting a total of six antibody injections. Control hu-mice were reconstituted with human cells from the same donor and infected with HIV-1YU2 but not treated with antibodies. Plasma viral loads were measured weekly. The gp120 sequences from mice with rebounding virus were obtained as described in F. Klein et al., HIV therapy by a combination of broadly neutralizing antibodies in humanized mice. *Nature* 492, 118-122 (2012).

ELISAs

High-binding 96-well ELISA plates (Costar) were coated overnight with 5 µg/mL of purified 2CC core, gp120.YU2 (wild type or mutants) or gp140.YU2 foldon trimer in PBS. After washing 6 times with PBS+0.05% Tween 20, the plates were blocked for 2 h with 2% BSA, 1 µM EDTA and 0.05% Tween-PBS ("blocking buffer"), and then incubated for 1 hour with IgGs that were added as seven consecutive 1:4 dilutions in PBS from an initial concentration of 4 µg/mL. After additional washing, the plates were developed by incubation with goat HRP-conjugated anti-human IgG antibodies (Jackson ImmunoResearch) (at 0.8 µg/mL in blocking buffer) for 1 hour followed by horseradish peroxidase (HRP) chromogenic substrate (ABTS solution; Invitrogen). For competition ELISAs, the plates were coated with 0.5 µg/mL BG505.SOSIP.664, washed, blocked for 2 hours with blocking buffer and then incubated for 1 hour with IgGs added as seven consecutive 1:4 dilutions in PBS from an initial concentration of 32 µg/mL, and in the presence of biotinylated antibody at a constant concentration of 4 µg/mL. The plates were then developed using HRP-congugated streptavidin (Jackson ImmunoReseach) (at 1 µg/mL in blocking buffer).

For ELISAs using BG505 SOSIP.664 trimers with a D7324 epitope tag (BG505 SOSIP.664-D7324) the plates were coated overnight with 5 µg/mL of D7324 antibody as described in Sanders, R. W., et al., A next-generation cleaved, soluble HIV-1 Env trimer, BG505 SOSIP.664 gp140, expresses multiple epitopes for broadly neutralizing but not non-neutralizing antibodies. *PLoS Pathog*, 2013. 9(9): p. e1003618, and then washed and incubated with 500 ng/mL of the trimer. After a further wash, IgGs were added for 1 h as seven consecutive 1:4 dilutions in PBS from initial concentrations of 4 µg/mL. The endpoint was generated by incubation with goat HRP-conjugated anti-human IgG antibodies, as described above. All experiments were performed at least 3 times.

Generation of CMV-Env Viruses

CMV-env expression cassettes were generated according to an established protocol (52). Briefly, the CMV promoter was amplified from pcDNA 3. 1D/V5-His-TOPO Expression vector using the following primers:

```
CMVenv:
                                   (SEQ ID NO: 101)
5'-AGTAATCAATTACGGGGTCATTAGTTCAT-3'
and CMVenv1A
                                   (SEQ ID NO: 102)
5'-CATAGGAGATGCCTAAGCCGGTGGAGCTCTGCTTATATAGACC
TC-3'.
```

The PCR product was purified using the Macherey-Nagel PCR and Gel Purification Kit. 1 ul of first round PCR product was amplified using the following primers:
env 1 ATOPO 5'-CACCGGCTTAGGCATCTCC-TATGGCAGGAAGAA-3' (SEQ ID NO: 103) and
Rev19 5'-ACTTTTTGACCACTTGCCACCCAT-3' (SEQ ID NO: 104) in a 20 µL volume containing 1× High Fidelity Buffer, 2 mM MgSO$_4$, 0.2 mM dNTPs, 0.5 units of High Fidelity Platinum Taq and 0.2 µM of each primer. Cycling conditions were 94° C. 2 min.; (94° C. 15 seconds; 55° C. 30 seconds; 68° C. 4 minutes)×35; 68° C. 10 minutes. The presence of env was validated by analysis on a 0.7% Agarose gel and the product was purified using the Macherey-Nagel Gel and PCR Purification Kit. 10 ng of envelope and 0.5 ng of CMV were then subjected to overlapping PCR with primers CMVenv and Rev19 in triplicates. Total reaction volume 6 was 50 µL containing 1× High Fidelity Buffer, 0.2 µM MgSO$_4$, 0.2 mM dNTPs, 1 unit of High Fidelity Platinum Taq and 0.4 µM of each primer. PCR was carried out at 94° C., 2 min.; (94° C., 30 seconds; 60° C. 30 seconds; 68° C., 4 minutes)×25; 68° C. 10 min. 500 ng of CMV-env were co-transfected with pSG3 Δenv in 6-well plates into 293T cells and supernatant was harvested after 48 hours. Supernatants were subjected to neutralization testing by TZM-bl as described supra.

Culture Virus (VOA)

Virus from donor EB354 was obtained by co-culture of patient peripheral blood mononuclear cells (PBMCs) with healthy donor PBMCs as described in van't Wout el al., Isolation and propagation of HIV-1 on peripheral blood mononuclear cells. *Nat Protoc*, 2008. 3(3): p. 363-70. Healthy donor PBMCs were obtained from patients by leukapheresis under study protocol MNU-0628 at Rockefeller University. Healthy donor PBMCs were pre-stimulated at a density of $5 \times 10^6$ cells per mL in IMDM containing 10% FBS, 1% Penicillin-Streptomycin and PHA at 1 µg/mL for 2-3 days at 37° C. and 5% $CO_2$. $6 \times 10^6$ of the stimulated donor PBMCs were then transferred to IMDM containing 10% FBS, 1% Penicillin-Streptomycin, 10 IU/mL IL-2 and 5 µg/mL polybrene and co-cultured with $5$-$10 \times 10^6$ EB354 PBMCs at 37° C. and 5% $CO_2$. Media was replaced weekly and the presence of p24 in culture supernatant was quantified by Lenti-X p24 Rapid Titer Kit (Clontech). Cultures exceeding 1 ng of p24 per mL of supernatant were frozen and stored at −80° C. Determination of tissue culture infectious dose 50 ($TCID_{50}$) and subsequent testing for sensitivity of autologous viruses to different broadly neutralizing antibodies and autologous serum IgG was carried out using a TZM-bl neutralization assay according to protocols described supra. All neutralization assays were run in duplicates.

HIV-1$_{YU2}$ Envelope Mutants

Single, double and triple mutations were introduced into wild-type HIV-1$_{YU2}$ envelope using the QuikChange (multi-) site-directed mutagenesis kit, according to the manufacturer's specifications (Agilent Technologies).

Analysis of Viral Evolution

Alignments of env nucleotide sequences were generated using ClustalW (version 2.11) or via manual alignment using Geneious (version 8.1.6) sequence analysis software. Regions that could not be unambiguously aligned were removed for phylogenetic analysis and diversity calculations. Evolutionary model classes for maximum likelihood phylogenetic analyses were selected using jModelTest. Maximum likelihood phylogenetic trees were generated using PhyML (version 3) with joint estimation of model parameter values and phylogenies. Pairwise genetic diversity was compared among samples using a two-sample U statistic test in the DIVEIN webtool.

Bioinformatic Processing of MiSeq Env-Sequences

Sequence adapters were removed using Cutadapt v1.8.3. Read assembly for each virus was performed in three steps. First, de novo assembly was performed using Spades v3.6.1 to yield long contig files. Contigs longer than 255 bp were subsequently aligned to an HIV envelope reference sequence and a consensus sequence was generated using Geneious 8. Finally, reads were re-aligned to the consensus sequence to close gaps and a final consensus was generated. Sequences with double peaks (cutoff consensus identity for any residue <75%) were omitted from downstream analysis.

Statistical Analyses

Statistical differences were analyzed by the Mann-Whitney test. GraphPad Prism software was used for analysis, and data were considered significant at *p≤0.05, p≤0.01, and *p≤0.001.

B. Results

Multiple bNAbs

Purified IgG from donor EB354 ranked in the top 1% for neutralization breadth and potency in a cohort of 394 HIV-1 infected long-term non-progressors. This donor was diagnosed with HIV-1 Clade B in 1986. EB354 received treatment with didanosine and stavudine between 1995 and 1998, but has had no antiretroviral therapy since that time. In 2002 EB354's viral load was <400 copies/mL and CD4 and CD8 counts were 954 and 1046 cells/mm$^3$, respectively. EB354 had three documented peaks in viremia between 2002 and 2006 (FIG. 1A). Serologic neutralizing potency and breadth were first assessed in 2006 when viral load was <400 copies/ml (FIGS. 1A and 1B and Table 3). The neutralizing activity increased until 2010, and has remained broad and potent since that time (FIG. 1B). HLA typing revealed HLA A*01:01, 24:02, B*27:05, 57:01, C*01:02, 06:02 (Table 3).

Figures 1D, 1E, 1F:
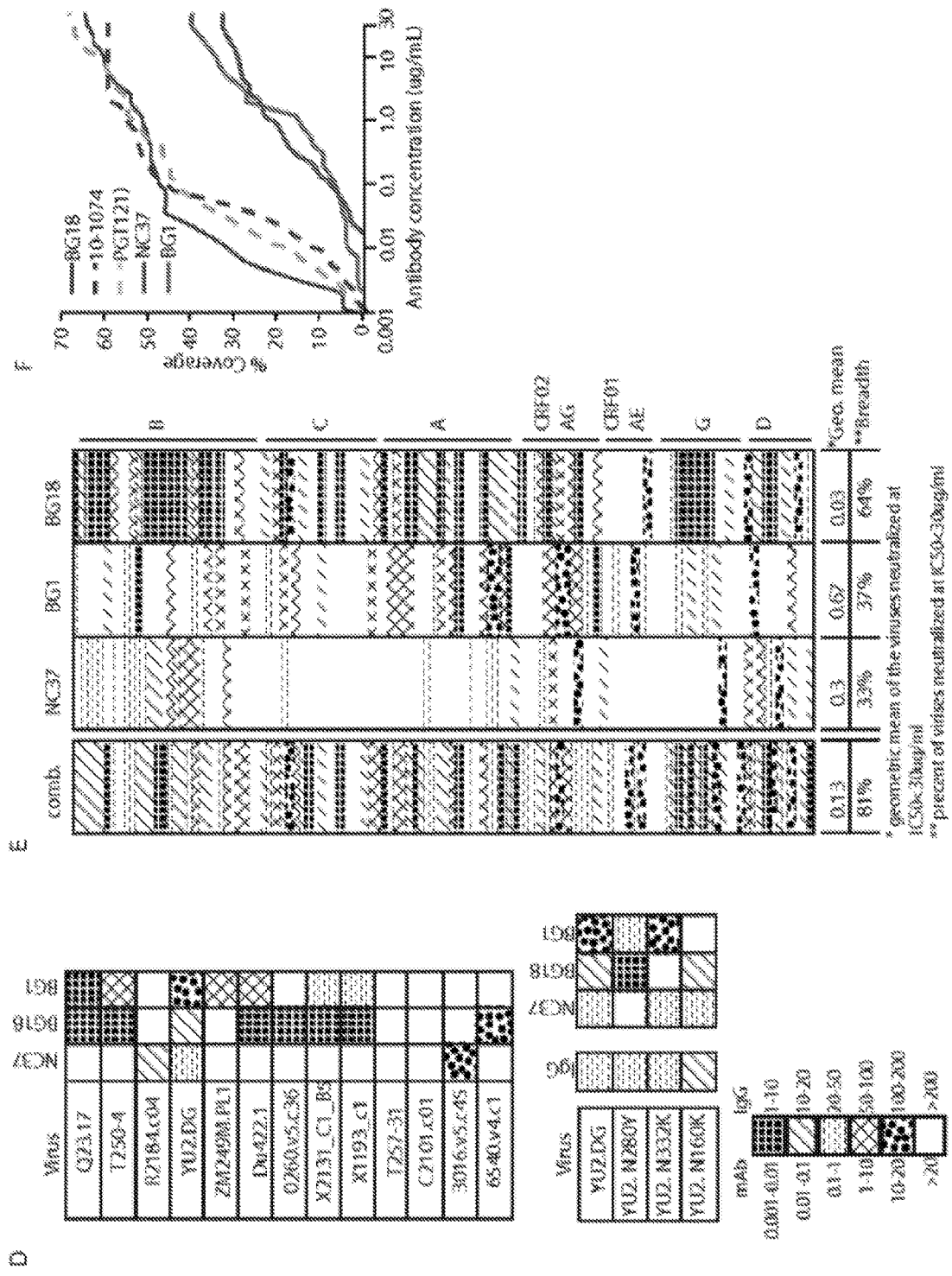

To isolate the antibodies that account for this subject's serologic activity, single cells were sorted using four different HIV-1 baits; 2CC core, gp140$_{YU2}$, a 1:1 mixture of gp140$_{92UG7.8}$ (Clade A)+gp140$_{CZA79012}$ (Clades C) and BG505 SOSIP.664 (FIG. 1C). A total of 241 paired heavy and light chains were isolated, of which 152 antibodies formed 22 different clones. Antibodies from 3 clones showed tier 2 neutralizing activity (FIG. 1C and Table 13). When compared to serum IgG from years 2010-2015, antibodies belonging to the clone as exemplified by antibody BG18 (FIG. 1C), recapitulated most of the serologic activity (FIG. 1D). Antibodies belonging to the other 2 neutralizing clones, exemplified by antibody NC37 and antibody BG1 (FIG. 1C), were less potent but complemented the activity of BG18 (FIG. 1D).

Figures 5A, 5B:
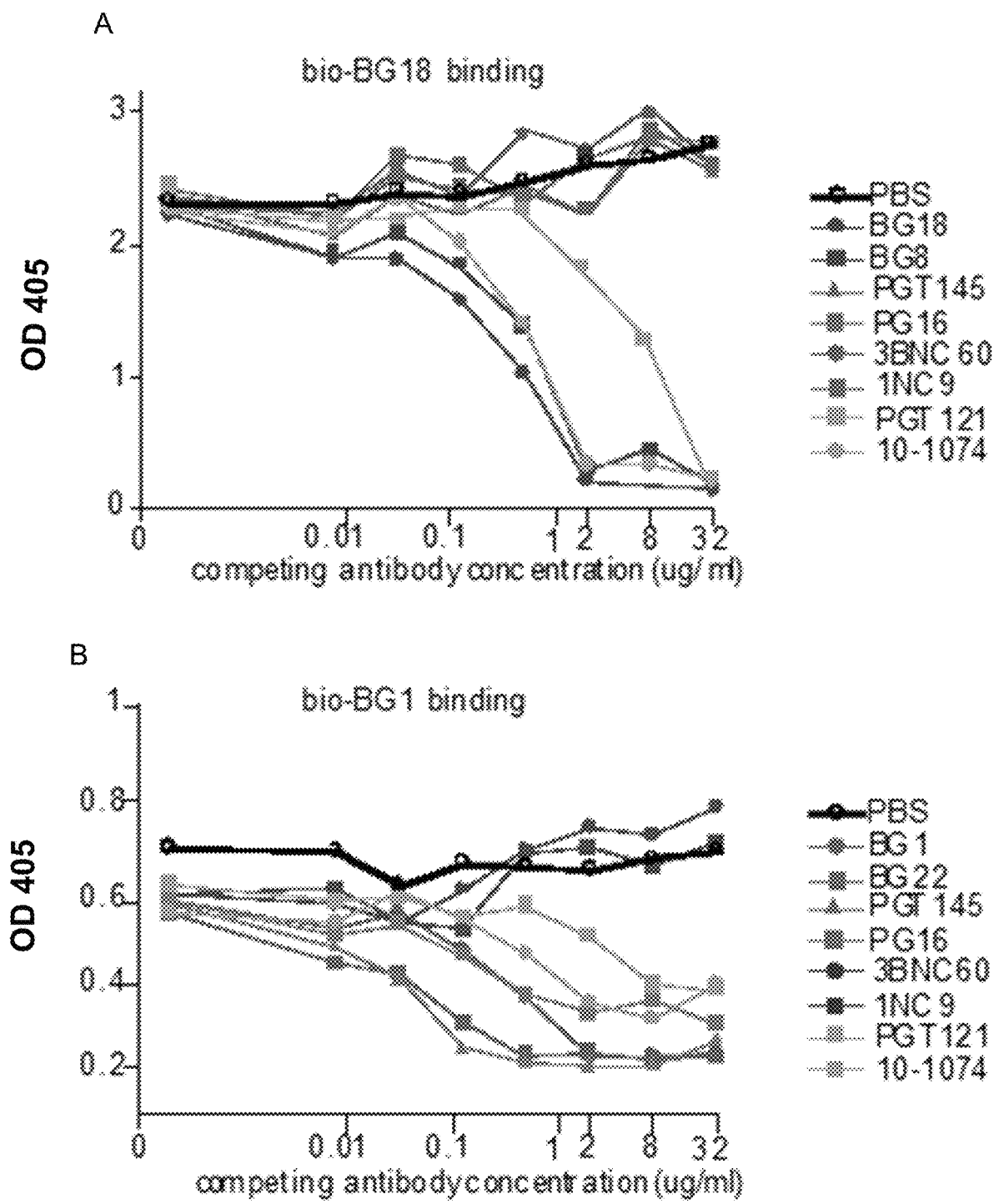
FIGS. 5A, 5B represent competition ELISA results. Each one of the neutralizing antibodies (equal amounts) was assayed for binding in ELISA to BG505 SOSIP.664 in the presence of increasing amounts of various competing antibodies. The black line indicates biotinylated antibody binding in the absence of competition.

To map the binding sites of the antibodies in the 3 neutralizing clones, TZM-bl assays were performed using HIV-1YU2 variants carrying epitope specific point mutations in Env. Whereas the polyclonal IgG showed no measurable change in sensitivity to the mutants, antibody BG18 was sensitive to YU2N332K (glycan-V3), antibody BG1 to YU2$_{NI60K}$ (V1V2), and antibody NC37 to YU2$_{N280Y}$ (CD4bs) (FIG. 1D). Consistent with the neutralization results, BG18 binding by ELISA was competitively inhibited by PGT121 and 10-1074; and BG1 binding was reduced by PGT145 (FIG. 5).

BG18 neutralized 64% of viruses in a 118-virus panel (FIG. 1E, Table 5) with a geometric mean IC$_{50}$ of 0.03 µg/ml and was and was comparable in breadth but more potent than either PGT121 or 10-1074 (FIG. 1F, Tables 5 through 10). Antibodies NC37 and BG1 showed geometric mean IC$_{50}$s of 0.3 µg/mL and 0.67 µg/mL, and 33% and 37% breadth, respectively. (FIGS. 1E and 1F, Tables 6 and 7). The 1:1:1 mix of the three bNAbs neutralized 81% of the viruses in the 118-virus panel with a geometric mean IC$_{50}$ of 0.130 µg/mL, indicating an additive effect (FIG. 1E, Table 11)

TABLE 5

IC50 and IC80 values in TZM-bl assay for BG18.

| Virus ID | Clade | IC50 | IC80 |
|---|---|---|---|
| 6535.3 | B | 0.001 | 0.005 |
| QH0692.42 | B | 0.013 | 0.042 |
| SC422661.8 | B | 0.005 | 0.021 |
| PVO.4 | B | 0.003 | 0.013 |
| TRO.11 | B | 0.001 | 0.002 |
| AC10.0.29 | B | 0.001 | 0.003 |
| RHPA4259.7 | B | 1.437 | >30 |
| THRO4156.18 | B | >30 | >30 |
| REJO4541.67 | B | >30 | >30 |
| TRJO4551.58 | B | 3.341 | 26.938 |
| WITO4160.33 | B | 0.018 | 0.250 |
| CAAN5342.A2 | B | 0.008 | 0.040 |
| WEAU_d15_410_787 | B (T/F) | 0.003 | 0.012 |
| 1006_11_C3_1601 | B (T/F) | 0.001 | 0.004 |
| 1054_07_TC4_1499 | B (T/F) | 0.005 | 0.022 |
| 1056_10_TA11_1826 | B (T/F) | 0.007 | 0.045 |
| 1012_11_TC21_3257 | B (T/F) | 0.003 | 0.012 |
| 6240_08_TA5_4622 | B (T/F) | 0.003 | 0.010 |
| 6244_13_B5_4576 | B (T/F) | 0.011 | 0.049 |
| 62357_14_D3_4589 | B (T/F) | 3.008 | >30 |
| SC05_8C11_2344 | B (T/F) | 0.003 | 0.016 |
| Du156.12 | C | 0.003 | 0.010 |
| Du172.17 | C | >30 | >30 |
| Du422.1 | C | 0.009 | 0.057 |
| ZM197M.PB7 | C | >30 | >30 |
| ZM214M.PL15 | C | >30 | >30 |
| ZM233M.PB6 | C | 2.866 | 29.805 |
| ZM249M.PL1 | C | >30 | >30 |
| ZM53M.PB12 | C | >30 | >30 |
| ZM109F.PB4 | C | >30 | >30 |
| ZM135M.PL10a | C | 0.029 | 0.161 |
| CAP45.2.00.G3 | C | >30 | >30 |
| CAP210.2.00.E8 | C | 3.469 | 10.748 |
| HIV-001428-2.42 | C | 0.004 | 0.021 |
| HIV-0013095-2.11 | C | 10.516 | 29.966 |
| HIV-16055-2.3 | C | >30 | >30 |
| HIV-16845-2.22 | C | 0.019 | 0.090 |
| Ce1086_B2 | C (T/F) | >30 | >30 |
| Ce0393_C3 | C (T/F) | >30 | >30 |
| Ce1176_A3 | C (T/F) | 0.004 | 0.012 |
| Ce2010_F5 | C (T/F) | >30 | >30 |
| Ce0682_E4 | C (T/F) | >30 | >30 |
| Ce1172_H1 | C (T/F) | 0.002 | 0.007 |
| Ce2060_G9 | C (T/F) | >30 | >30 |
| Ce703010054_2A2 | C (T/F) | >30 | >30 |
| BF1266.431a | C (T/F) | >30 | >30 |
| 246F C1G | C (T/F) | 0.034 | 0.257 |
| 249M B10 | C (T/F) | >30 | >30 |
| ZM247v1 (Rev-) | C (T/F) | 1.454 | 8.725 |
| 7030102001E5 (Rev-) | C (T/F) | 0.002 | 0.008 |
| 1394C9G1 (Rev-) | C (T/F) | 0.029 | 0.350 |
| Ce704809221_1B3 | C (T/F) | 4.394 | >30 |
| CNE19 | BC | >30 | >30 |
| CNE20 | BC | 0.002 | 0.006 |
| CNE21 | BC | 0.002 | 0.007 |
| CNE17 | BC | 0.020 | 0.109 |
| CNE30 | BC | 0.019 | 0.059 |
| CNE52 | BC | 0.012 | 0.045 |
| CNE53 | BC | 0.003 | 0.011 |
| CNE58 | BC | 0.024 | 0.073 |
| MS208.A1 | A | >30 | >30 |
| Q23.17 | A | 0.006 | 0.020 |
| Q461.e2 | A | >30 | >30 |
| Q769.d22 | A | >30 | >30 |
| Q259.d2.17 | A | >30 | >30 |
| Q842.d12 | A | 13.986 | >30 |
| 3415.v1.c1 | A | 0.023 | 0.087 |
| 3365.v2.c2 | A | 0.013 | 0.037 |
| 191955_A11 | A (T/F) | >30 | >30 |
| 191084 B7-19 | A (T/F) | 0.011 | 0.043 |
| 9004SS_A3_4 | A (T/F) | 0.005 | 0.056 |
| T257-31 | CRF02_AG | >30 | >30 |
| 928-28 | CRF02_AG | 0.761 | 3.934 |
| 263-8 | CRF02_AG | 1.380 | 7.548 |
| T250-4 | CRF02_AG | 0.001 | 0.006 |
| T251-18 | CRF02_AG | 0.086 | 0.328 |
| T278-50 | CRF02_AG | 2.947 | 12.875 |
| T255-34 | CRF02_AG | >30 | >30 |
| 211-9 | CRF02_AG | 1.299 | 5.529 |
| 235-47 | CRF02_AG | 0.005 | 0.017 |

TABLE 5-continued

IC50 and IC80 values in TZM-bl assay for BG18.

BG18

| Virus ID | Clade | IC50 | IC80 |
|---|---|---|---|
| 620345.c01 | CRF01_AE | >30 | >30 |
| CNE8 | CRF01_AE | >30 | >30 |
| C1080.c03 | CRF01_AE | 5.369 | >30 |
| R2184.c04 | CRF01_AE | >30 | >30 |
| R1166.c01 | CRF01_AE | >30 | >30 |
| R3265.c06 | CRF01_AE | >30 | >30 |
| C2101.c01 | CRF01_AE | >30 | >30 |
| C3347.c11 | CRF01_AE | >30 | >30 |
| C4118.c09 | CRF01_AE | >30 | >30 |
| CNE5 | CRF01_AE | >30 | >30 |
| BJOX009000.02.4 | CRF01_AE | 24.376 | >30 |
| BJOX015000.11.5 | CRF01_AE (T/F) | >30 | >30 |
| BJOX010000.06.2 | CRF01_AE (T/F) | >30 | >30 |
| BJOX025000.01.1 | CRF01_AE (T/F) | >30 | >30 |
| BJOX028000.10.3 | CRF01_AE (T/F) | 0.474 | 14.851 |
| X1193_c1 | G | 0.005 | 0.022 |
| P0402_c2_11 | G | 0.005 | 0.029 |
| X1254_c3 | G | 0.004 | 0.012 |
| X2088_c9 | G | 0.004 | 0.009 |
| X2131_C1_B5 | G | 0.002 | 0.008 |
| P1981_C5_3 | G | 0.006 | 0.019 |
| X1632_S2_B10 | G | >30 | >30 |
| 3016.v5.c45 | D | >30 | >30 |
| A07412M1.vrc12 | D | 0.081 | 1.715 |
| 231965.c01 | D | >30 | >30 |
| 231966.c02 | D | >30 | >30 |
| 191821_E6_1 | D (T/F) | 14.076 | >30 |
| 3817.v2.c59 | CD | 0.219 | 1.059 |
| 6480.v4.c25 | CD | 0.016 | 0.116 |
| 6952.v1.c20 | CD | 0.005 | 0.011 |
| 6811.v7.c18 | CD | 0.001 | 0.006 |
| 89-F1_2_25 | CD | >30 | >30 |
| 3301.v1.c24 | AC | 0.025 | 0.082 |
| 6041.v3.c23 | AC | >30 | >30 |
| 6540.v4.c1 | AC | 28.197 | >30 |
| 6545.v4.c1 | AC | >30 | >30 |
| 0815.v3.c3 | ACD | 0.160 | 5.964 |
| 3103.v3.c10 | ACD | 0.002 | 0.005 |
| BG505/T332N | A | <0.0001 | 0.002 |
| YU2_WT | B | 0.033 | 0.198 |
| YU2_N276D | B | 0.012 | 0.036 |
| YU2_N332K | B | >30 | >30 |
| YU2_N160K | B | 0.028 | 0.150 |
| YU2_N280Y | B | 0.005 | 0.016 |

TABLE 6

IC50 and IC80 values in TZM-bl assay for NC37.

NC37

| Virus ID | Clade | IC50 | IC80 |
|---|---|---|---|
| 6535.3 | B | >30 | >30 |
| QH0692.42 | B | 0.582 | 2.054 |
| SC422661.8 | B | 0.071 | 0.321 |
| PVO.4 | B | 0.412 | 2.825 |
| TRO.11 | B | 0.337 | 1.761 |
| AC10.0.29 | B | >30 | >30 |
| RHPA4259.7 | B | 0.345 | 2.289 |
| THRO4156.18 | B | >30 | >30 |
| REJO4541.67 | B | 0.104 | 0.304 |
| TRJO4551.58 | B | 0.143 | 1.615 |
| WITO4160.33 | B | 0.733 | 17.779 |
| CAAN5342.A2 | B | 0.911 | 3.694 |
| WEAU_d15_410_787 | B (T/F) | 0.037 | 0.133 |
| 1006_11_C3_1601 | B (T/F) | 0.054 | 0.207 |
| 1054_07_TC4_1499 | B (T/F) | >30 | >30 |
| 1056_10_TA11_1826 | B (T/F) | 1.048 | 5.510 |
| 1012_11_TC21_3257 | B (T/F) | 0.099 | 0.638 |
| 6240_08_TA5_4622 | B (T/F) | 1.236 | 6.388 |
| 6244_13_B5_4576 | B (T/F) | 5.574 | >30 |
| 62357_14_D3_4589 | B (T/F) | 1.860 | 29.422 |
| SC05_8C11_2344 | B (T/F) | 0.202 | 0.714 |
| Du156.12 | C | >30 | >30 |
| Du172.17 | C | >30 | >30 |
| Du422.1 | C | >30 | >30 |
| ZM197M.PB7 | C | 3.098 | 17.368 |
| ZM214M.PL15 | C | >30 | >30 |
| ZM233M.PB6 | C | >30 | >30 |
| ZM249M.PL1 | C | >30 | >30 |
| ZM53M.PB12 | C | >30 | >30 |
| ZM109F.PB4 | C | >30 | >30 |
| ZM135M.PL10a | C | >30 | >30 |
| CAP45.2.00.G3 | C | >30 | >30 |
| CAP210.2.00.E8 | C | >30 | >30 |
| HIV-001428-2.42 | C | 0.124 | 2.275 |
| HIV-0013095-2.11 | C | >30 | >30 |
| HIV-16055-2.3 | C | >30 | >30 |
| HIV-16845-2.22 | C | >30 | >30 |
| Ce1086_B2 | C (T/F) | 2.322 | 20.996 |
| Ce0393_C3 | C (T/F) | >30 | >30 |
| Ce1176_A3 | C (T/F) | >30 | >30 |
| Ce2010_F5 | C (T/F) | >30 | >30 |
| Ce0682_E4 | C (T/F) | >30 | >30 |
| Ce1172_H1 | C (T/F) | >30 | >30 |
| Ce2060_G9 | C (T/F) | >30 | >30 |
| Ce703010054_2A2 | C (T/F) | >30 | >30 |
| BF1266.431a | C (T/F) | >30 | >30 |
| 246F C1G | C (T/F) | >30 | >30 |
| 249M B10 | C (T/F) | >30 | >30 |
| ZM247v1 (Rev-) | C (T/F) | >30 | >30 |
| 7030102001E5 (Rev-) | C (T/F) | >30 | >30 |
| 1394C9G1 (Rev-) | C (T/F) | >30 | >30 |
| Ce704809221_1B3 | C (T/F) | >30 | >30 |
| CNE19 | BC | >30 | >30 |
| CNE20 | BC | >30 | >30 |
| CNE21 | BC | >30 | >30 |
| CNE17 | BC | >30 | >30 |
| CNE30 | BC | 0.915 | 11.813 |
| CNE52 | BC | >30 | >30 |
| CNE53 | BC | >30 | >30 |
| CNE58 | BC | >30 | >30 |
| MS208.A1 | A | >30 | >30 |
| Q23.17 | A | >30 | >30 |
| Q461.e2 | A | >30 | >30 |
| Q769.d22 | A | 0.242 | 1.574 |
| Q259.d2.17 | A | >30 | >30 |
| Q842.d12 | A | 0.255 | 1.821 |
| 3415.v1.c1 | A | 0.183 | 0.654 |
| 3365.v2.c2 | A | >30 | >30 |
| 191955_A11 | A (T/F) | >30 | >30 |
| 191084 B7-19 | A (T/F) | 0.064 | 0.208 |
| 9004SS_A3_4 | A (T/F) | >30 | >30 |
| T257-31 | CRF02_AG | >30 | >30 |
| 928-28 | CRF02_AG | >30 | >30 |
| 263-8 | CRF02_AG | 0.269 | 1.523 |
| T250-4 | CRF02_AG | >30 | >30 |
| T251-18 | CRF02_AG | 1.835 | 7.857 |
| T278-50 | CRF02_AG | >30 | >30 |
| T255-34 | CRF02_AG | >30 | >30 |
| 211-9 | CRF02_AG | >30 | >30 |
| 235-47 | CRF02_AG | 14.369 | >30 |
| 620345.c01 | CRF01_AE | >30 | >30 |
| CNE8 | CRF01_AE | >30 | >30 |
| C1080.c03 | CRF01_AE | >30 | >30 |
| R2184.c04 | CRF01_AE | 0.025 | 0.082 |
| R1166.c01 | CRF01_AE | >30 | >30 |
| R3265.c06 | CRF01_AE | >30 | >30 |
| C2101.c01 | CRF01_AE | >30 | >30 |
| C3347.c11 | CRF01_AE | >30 | >30 |
| C4118.c09 | CRF01_AE | >30 | >30 |
| CNE5 | CRF01_AE | >30 | >30 |
| BJOX009000.02.4 | CRF01_AE | >30 | >30 |
| BJOX015000.11.5 | CRF01_AE (T/F) | >30 | >30 |
| BJOX010000.06.2 | CRF01_AE (T/F) | >30 | >30 |
| BJOX025000.01.1 | CRF01_AE (T/F) | >30 | >30 |
| BJOX028000.10.3 | CRF01_AE (T/F) | >30 | >30 |

TABLE 6-continued

IC50 and IC80 values in TZM-bl assay for NC37.
NC37

| Virus ID | Clade | IC50 | IC80 |
|---|---|---|---|
| X1193_c1 | G | >30 | >30 |
| P0402_c2_11 | G | >30 | >30 |
| X1254_c3 | G | >30 | >30 |
| X2088_c9 | G | >30 | >30 |
| X2131_C1_B5 | G | >30 | >30 |
| P1981_C5_3 | G | >30 | >30 |
| X1632_S2_B10 | G | >30 | >30 |
| 3016.v5.c45 | D | 23.592 | >30 |
| A07412M1.vrc12 | D | >30 | >30 |
| 231965.c01 | D | >30 | >30 |
| 231966.c02 | D | >30 | >30 |
| 191821_E6_1 | D (T/F) | 9.963 | >30 |
| 3817.v2.c59 | CD | >30 | >30 |
| 6480.v4.c25 | CD | 3.060 | >30 |
| 6952.v1.c20 | CD | 0.104 | 0.477 |
| 6811.v7.c18 | CD | >30 | >30 |
| 89-F1_2_25 | CD | 17.963 | >30 |
| 3301.v1.c24 | AC | >30 | >30 |
| 6041.v3.c23 | AC | 0.018 | 0.054 |
| 6540.v4.c1 | AC | >30 | >30 |
| 6545.v4.c1 | AC | >30 | >30 |
| 0815.v3.c3 | ACD | 0.022 | 0.082 |
| 3103.v3.c10 | ACD | >30 | >30 |
| BG505/T332N | A | | |
| YU2_WT | B | 0.12 | |
| YU2_N276D | B | NT | |
| YU2_N332K | B | 0.05 | |
| YU2_N160K | B | 0.05 | |
| YU2_N280Y | B | >30 | |

TABLE 7

IC50 and IC80 values in TZM-bl assay for BG1.
BG1

| Virus ID | Clade | IC50 | IC80 |
|---|---|---|---|
| 6535.3 | B | 0.322 | 1.130 |
| QH0692.42 | B | >30 | >30 |
| SC422661.8 | B | >30 | >30 |
| PVO.4 | B | >30 | >30 |
| TRO.11 | B | >30 | >30 |
| AC10.0.29 | B | 0.012 | 0.043 |
| RHPA4259.7 | B | >30 | >30 |
| THRO4156.18 | B | >30 | >30 |
| REJO4541.67 | B | 0.342 | 1.662 |
| TRJO4551.58 | B | >30 | >30 |
| WITO4160.33 | B | 0.002 | 0.014 |
| CAAN5342.A2 | B | >30 | >30 |
| WEAU_d15_410_787 | B (T/F) | >30 | >30 |
| 1006_11_C3_1601 | B (T/F) | >30 | >30 |
| 1054_07_TC4_1499 | B (T/F) | >30 | >30 |
| 1056_10_TA11_1826 | B (T/F) | 5.428 | 29.924 |
| 1012_11_TC21_3257 | B (T/F) | >30 | >30 |
| 6240_08_TA5_4622 | B (T/F) | >30 | >30 |
| 6244_13_B5_4576 | B (T/F) | >30 | >30 |
| 62357_14_D3_4589 | B (T/F) | 0.638 | 2.889 |
| SC05_8C11_2344 | B (T/F) | >30 | >30 |
| Du156.12 | C | 1.525 | 6.031 |
| Du172.17 | C | >30 | >30 |
| Du422.1 | C | 1.804 | 13.708 |
| ZM197M.PB7 | C | >30 | >30 |
| ZM214M.PL15 | C | >30 | >30 |
| ZM233M.PB6 | C | >30 | >30 |
| ZM249M.PL1 | C | 1.223 | 6.795 |
| ZM53M.PB12 | C | >30 | >30 |
| ZM109F.PB4 | C | >30 | >30 |
| ZM135M.PL10a | C | >30 | >30 |
| CAP45.2.00.G3 | C | 0.149 | 0.383 |
| CAP210.2.00.E8 | C | >30 | >30 |
| HIV-001428-2.42 | C | 1.094 | 3.124 |
| HIV-0013095-2.11 | C | >30 | >30 |
| HIV-16055-2.3 | C | 4.296 | 16.939 |
| HIV-16845-2.22 | C | >30 | >30 |
| Ce1086_B2 | C (T/F) | >30 | >30 |
| Ce0393_C3 | C (T/F) | >30 | >30 |
| Ce1176_A3 | C (T/F) | 0.031 | 0.165 |
| Ce2010_F5 | C (T/F) | >30 | >30 |
| Ce0682_E4 | C (T/F) | >30 | >30 |
| Ce1172_H1 | C (T/F) | >30 | >30 |
| Ce2060_G9 | C (T/F) | >30 | >30 |
| Ce703010054_2A2 | C (T/F) | >30 | >30 |
| BF1266.431a | C (T/F) | >30 | >30 |
| 246F C1G | C (T/F) | >30 | >30 |
| 249M B10 | C (T/F) | 1.473 | 5.445 |
| ZM247v1 (Rev-) | C (T/F) | >30 | >30 |
| 7030102001E5 (Rev-) | C (T/F) | >30 | >30 |
| 1394C9G1 (Rev-) | C (T/F) | 1.279 | 7.249 |
| Ce704809221_1B3 | C (T/F) | 3.251 | 18.455 |
| CNE19 | BC | 1.267 | 10.883 |
| CNE20 | BC | 4.264 | >30 |
| CNE21 | BC | >30 | >30 |
| CNE17 | BC | >30 | >30 |
| CNE30 | BC | >30 | >30 |
| CNE52 | BC | 0.975 | 5.008 |
| CNE53 | BC | 1.318 | 7.470 |
| CNE58 | BC | >30 | >30 |
| MS208.A1 | A | 1.478 | 6.543 |
| Q23.17 | A | 0.008 | 0.016 |
| Q461.e2 | A | >30 | >30 |
| Q769.d22 | A | >30 | >30 |
| Q259.d2.17 | A | >30 | >30 |
| Q842.d12 | A | 1.395 | 4.297 |
| 3415.v1.c1 | A | 14.412 | >30 |
| 3365.v2.c2 | A | 1.161 | 4.272 |
| 191955_A11 | A (T/F) | 0.008 | 0.018 |
| 191084 B7-19 | A (T/F) | >30 | >30 |
| 9004SS_A3_4 | A (T/F) | >30 | >30 |
| T257-31 | CRF02_AG | >30 | >30 |
| 928-28 | CRF02_AG | >30 | >30 |
| 263-8 | CRF02_AG | >30 | >30 |
| T250-4 | CRF02_AG | 3.921 | >30 |
| T251-18 | CRF02_AG | 3.591 | 17.977 |
| T278-50 | CRF02_AG | 19.313 | >30 |
| T255-34 | CRF02_AG | 11.589 | >30 |
| 211-9 | CRF02_AG | 2.852 | 12.939 |
| 235-47 | CRF02_AG | 1.275 | 4.384 |
| 620345.c01 | CRF01_AE | 0.626 | 4.229 |
| CNE8 | CRF01_AE | >30 | >30 |
| C1080.c03 | CRF01_AE | 0.002 | 0.005 |
| R2184.c04 | CRF01_AE | >30 | >30 |
| R1166.c01 | CRF01_AE | >30 | >30 |
| R3265.c06 | CRF01_AE | 0.611 | 3.438 |
| C2101.c01 | CRF01_AE | >30 | >30 |
| C3347.c11 | CRF01_AE | >30 | >30 |
| C4118.c09 | CRF01_AE | 22.788 | >30 |
| CNE5 | CRF01_AE | 0.351 | 1.277 |
| BJOX009000.02.4 | CRF01_AE | >30 | >30 |
| BJOX015000.11.5 | CRF01_AE (T/F) | >30 | >30 |
| BJOX010000.06.2 | CRF01_AE (T/F) | >30 | >30 |
| BJOX025000.01.1 | CRF01_AE (T/F) | >30 | >30 |
| BJOX028000.10.3 | CRF01_AE (T/F) | >30 | >30 |
| X1193_c1 | G | 0.138 | 0.463 |
| P0402_c2_11 | G | >30 | >30 |
| X1254_c3 | G | 0.048 | 0.086 |
| X2088_c9 | G | >30 | >30 |
| X2131_C1_B5 | G | 0.116 | 0.313 |
| P1981_C5_3 | G | >30 | >30 |
| X1632_K_B10 | G | 0.079 | 0.250 |
| 3016.v5.c45 | D | >30 | >30 |
| A07412M1.vrc12 | D | >30 | >30 |
| 231965.c01 | D | >30 | >30 |
| 231966.c02 | D | >30 | >30 |
| 191821_E6_1 | D (T/F) | >30 | >30 |
| 3817.v2.c59 | CD | 11.147 | >30 |
| 6480.v4.c25 | CD | >30 | >30 |
| 6952.v1.c20 | CD | >30 | >30 |

TABLE 7-continued

IC50 and IC80 values in TZM-bl assay for BG1.

| Virus ID | BG1 Clade | IC50 | IC80 |
| --- | --- | --- | --- |
| 6811.v7.c18 | CD | >30 | >30 |
| 89-F1_2_25 | CD | >30 | >30 |
| 3301.v1.c24 | AC | >30 | >30 |
| 6041.v3.c23 | AC | 6.745 | 16.641 |
| 6540.v4.c1 | AC | >30 | >30 |
| 6545.v4.c1 | AC | >30 | >30 |
| 0815.v3.c3 | ACD | >30 | >30 |
| 3103.v3.c10 | ACD | >30 | >30 |
| BG505/T332N | A | 0.034 | 0.125 |
| YU2_WT | B | 15.816 | >30 |
| YU2_N276D | B | 18.765 | >30 |
| YU2_N332K | B | 19.434 | >30 |
| YU2_N160K | B | >30 | >30 |
| YU2_N280Y | B | 8.998 | 23.023 |

TABLE 8

IC50 and IC80 values in TZM-bl assay for BG8.

| Virus ID | BG8 Clade | IC50 | IC80 |
| --- | --- | --- | --- |
| 6535.3 | B | 0.007 | 0.022 |
| QH0692.42 | B | 0.106 | 0.383 |
| SC422661.8 | B | 0.058 | 0.368 |
| PVO.4 | B | 0.072 | 0.252 |
| TRO.11 | B | 0.011 | 0.039 |
| AC10.0.29 | B | 0.015 | 0.043 |
| RHPA4259.7 | B | 0.023 | 0.083 |
| THRO4156.18 | B | >10 | >10 |
| REJO4541.67 | B | >10 | >10 |
| TRJO4551.58 | B | 0.057 | 0.218 |
| WITO4160.33 | B | 0.111 | 0.828 |
| CAAN5342.A2 | B | 0.005 | 0.019 |
| WEAU_d15_410_787 | B (T/F) | 0.031 | 0.112 |
| 1006_11_C3_1601 | B (T/F) | 0.002 | 0.006 |
| 1054_07_TC4_1499 | B (T/F) | 0.048 | 0.222 |
| 1056_10_TA11_1826 | B (T/F) | 0.038 | 0.168 |
| 1012_11_TC21_3257 | B (T/F) | 0.011 | 0.047 |
| 6240_08_TA5_4622 | B (T/F) | 0.038 | 0.131 |
| 6244_13_B5_4576 | B (T/F) | 0.091 | 0.380 |
| 62357_14_D3_4589 | B (T/F) | >10 | >10 |
| SC05_8C11_2344 | B (T/F) | 0.017 | 0.048 |
| Du156.12 | C | 0.010 | 0.036 |
| Du172.17 | C | 0.049 | 0.194 |
| Du422.1 | C | 0.047 | 0.113 |
| ZM197M.PB7 | C | >10 | >10 |
| ZM214M.PE15 | C | 0.415 | 2.970 |
| ZM233M.PB6 | C | 0.058 | 0.371 |
| ZM249M.PL1 | C | >10 | >10 |
| ZM53M.PB12 | C | >10 | >10 |
| ZM109F.PB4 | C | >10 | >10 |
| ZM135M.PE10a | C | 0.061 | 0.263 |
| CAP45.2.00.G3 | C | >10 | >10 |
| CAP210.2.00.E8 | C | >10 | >10 |
| HIV-001428-2.42 | C | 0.035 | 0.126 |
| HIV-0013095-2.11 | C | >10 | >10 |
| HIV-16055-2.3 | C | >10 | >10 |
| HIV-16845-2.22 | C | 0.727 | 3.930 |
| Ce1086_B2 | C (T/F) | >10 | >10 |
| Ce0393_C3 | C (T/F) | >10 | >10 |
| Ce1176_A3 | C (T/F) | 0.022 | 0.070 |
| Ce2010_F5 | C (T/F) | >10 | >10 |
| Ce0682_E4 | C (T/F) | >10 | >10 |
| Ce1172_H1 | C (T/F) | 0.019 | 0.083 |
| Ce2060_G9 | C (T/F) | >10 | >10 |
| Ce703010054_2A2 | C (T/F) | >10 | >10 |
| BF1266.431a | C (T/F) | >10 | >10 |
| 246F C1G | C (T/F) | 0.035 | 0.119 |
| 249M B10 | C (T/F) | >10 | >10 |
| ZM247v1(Rev−) | C (T/F) | 0.042 | 0.146 |
| 7030102001E5(Rev−) | C (T/F) | 0.009 | 0.019 |
| 1394C9G1(Rev−) | C (T/F) | 0.031 | 0.093 |
| Ce704809221_1B3 | C (T/F) | 0.084 | 0.395 |
| CNE19 | BC | 0.075 | >10 |
| CNE20 | BC | 0.002 | 0.005 |
| CNE21 | BC | 0.047 | 0.124 |
| CNE17 | BC | 1.180 | 4.853 |
| CNE30 | BC | 0.261 | 0.678 |
| CNE52 | BC | 1.991 | 9.763 |
| CNE53 | BC | 0.013 | 0.058 |
| CNE58 | BC | 0.165 | 0.476 |
| MS208.A1 | A | >10 | >10 |
| Q23.17 | A | 0.005 | 0.015 |
| Q461.e2 | A | >10 | >10 |
| Q769.d22 | A | >10 | >10 |
| Q259.d2.17 | A | >10 | >10 |
| Q842.d12 | A | >10 | >10 |
| 3415.v1.c1 | A | >10 | >10 |
| 3365.v2.c2 | A | 0.057 | 0.200 |
| 191955_A11 | A (T/F) | >10 | >10 |
| 191084 B7-19 | A (T/F) | 0.026 | 0.108 |
| 9004SS_A3_4 | A (T/F) | 0.012 | 0.032 |
| T257-31 | CRF02_AG | >10 | >10 |
| 928-28 | CRF02_AG | 0.616 | 2.396 |
| 263-8 | CRF02_AG | 0.416 | 5.714 |
| T250-4 | CRF02_AG | 0.002 | 0.005 |
| T251-18 | CRF02_AG | 0.399 | 2.292 |
| T278-50 | CRF02_AG | 1.713 | >10 |
| T255-34 | CRF02_AG | >10 | >10 |
| 211-9 | CRF02_AG | 0.065 | 0.403 |
| 235-47 | CRF02_AG | 0.058 | 0.224 |
| 620345.c01 | CRF01_AE | >10 | >10 |
| CNE8 | CRF01_AE | >10 | >10 |
| C1080.c03 | CRF01_AE | >10 | >10 |
| R2184.c04 | CRF01_AE | >10 | >10 |
| R1166.c01 | CRF01_AE | >10 | >10 |
| R3265.c06 | CRF01_AE | >10 | >10 |
| C2101.c01 | CRF01_AE | >10 | >10 |
| C3347.c11 | CRF01_AE | >10 | >10 |
| C4118.c09 | CRF01_AE | >10 | >10 |
| CNE5 | CRF01_AE | >10 | >10 |
| BJOX009000.02.4 | CRF01_AE | >10 | >10 |
| BJOX015000.11.5 | CRF01_AE (T/F) | >10 | >10 |
| BJOX010000.06.2 | CRF01_AE (T/F) | >10 | >10 |
| BJOX025000.01.1 | CRF01_AE (T/F) | >10 | >10 |
| BJOX028000.10.3 | CRF01_AE (T/F) | >10 | >10 |
| X1193_c1 | G | 0.070 | 0.207 |
| P0402_c2_11 | G | 0.008 | 0.024 |
| X1254_c3 | G | 0.063 | 0.239 |
| X2088_c9 | G | 0.003 | 0.010 |
| X2131_C1_B5 | G | 0.014 | 0.056 |
| P1981_C5_3 | G | 0.004 | 0.013 |
| X1632_S2_B10 | G | >10 | >10 |
| 3016.v5.c45 | D | >10 | >10 |
| A07412M1.vrc12 | D | 0.011 | 0.037 |
| 231965.c01 | D | >10 | >10 |
| 231966.c02 | D | >10 | >10 |
| 191821_E6_1 | D (T/F) | >10 | >10 |
| 3817.v2.c59 | CD | 0.706 | 4.492 |
| 6480.v4.c25 | CD | 0.006 | 0.023 |
| 6952.v1.c20 | CD | 0.023 | 0.086 |
| 6811.v7.c18 | CD | 0.003 | 0.009 |
| 89-F1_2_25 | CD | >10 | >10 |
| 3301.v1.c24 | AC | 0.018 | 0.049 |
| 6041.v3.c23 | AC | >10 | >10 |
| 6540.v4.c1 | AC | >10 | >10 |
| 6545.v4.c1 | AC | >10 | >10 |
| 0815.v3.c3 | ACD | 0.043 | 0.197 |
| 3103.v3.c10 | ACD | 0.024 | 0.061 |

TABLE 9

IC50 and IC80 values in TZM-bl assay for 10-1074

| Virus ID | 10-1074 Clade | IC50 | IC80 |
|---|---|---|---|
| 6535.3 | B | 0.007 | 0.022 |
| QH0692.42 | B | 0.106 | 0.383 |
| SC422661.8 | B | 0.058 | 0.368 |
| PV0.4 | B | 0.072 | 0.252 |
| TRO.11 | B | 0.011 | 0.039 |
| AC10.0.29 | B | 0.015 | 0.043 |
| RHPA4259.7 | B | 0.023 | 0.083 |
| THRO4156.18 | B | >10 | >10 |
| REJO4541.67 | B | >10 | >10 |
| TRJO4551.58 | B | 0.057 | 0.218 |
| WITO4160.33 | B | 0.111 | 0.828 |
| CAAN5342.A2 | B | 0.005 | 0.019 |
| WEAU_d15_410_787 | B (T/F) | 0.031 | 0.112 |
| 1006_11_C3_1601 | B (T/F) | 0.002 | 0.006 |
| 1054_07_TC4_1499 | B (T/F) | 0.048 | 0.222 |
| 1056_10_TA11_1826 | B (T/F) | 0.038 | 0.168 |
| 1012_11_TC21_3257 | B (T/F) | 0.011 | 0.047 |
| 6240_08_TA5_4622 | B (T/F) | 0.038 | 0.131 |
| 6244_13_B5_4576 | B (T/F) | 0.091 | 0.380 |
| 62357_14_D3_4589 | B (T/F) | >10 | >10 |
| SC05_8C11_2344 | B (T/F) | 0.017 | 0.048 |
| Du156.12 | C | 0.010 | 0.036 |
| Du172.17 | C | 0.049 | 0.194 |
| Du422.1 | C | 0.047 | 0.113 |
| ZM197M.PB7 | C | >10 | >10 |
| ZM214M.PL15 | C | 0.415 | 2.970 |
| ZM233M.PB6 | C | 0.058 | 0.371 |
| ZM249M.PL1 | C | >10 | >10 |
| ZM53M.PB12 | C | >10 | >10 |
| ZM109F.PB4 | C | >10 | >10 |
| ZM135M.PE10a | C | 0.061 | 0.263 |
| CAP45.2.00.G3 | C | >10 | >10 |
| CAP210.2.00.E8 | C | >10 | >10 |
| HIV-001428-2.42 | C | 0.035 | 0.126 |
| HIV-0013095-2.11 | C | >10 | >10 |
| HIV-16055-2.3 | C | >10 | >10 |
| HIV-16845-2.22 | C | 0.727 | 3.930 |
| Ce1086_B2 | C (T/F) | >10 | >10 |
| Ce0393_C3 | C (T/F) | >10 | >10 |
| Ce1176_A3 | C (T/F) | 0.022 | 0.070 |
| Ce2010_F5 | C (T/F) | >10 | >10 |
| Ce0682_E4 | C (T/F) | >10 | >10 |
| Ce1172_H1 | C (T/F) | 0.019 | 0.083 |
| Ce2060_G9 | C (T/F) | >10 | >10 |
| Ce703010054_2A2 | C (T/F) | >10 | >10 |
| BF1266.431a | C (T/F) | >10 | >10 |
| 246FC1G | C (T/F) | 0.035 | 0.119 |
| 249MB10 | C (T/F) | >10 | >10 |
| ZM247v1(Rev−) | C (T/F) | 0.042 | 0.146 |
| 7030102001E5(Rev−) | C (T/F) | 0.009 | 0.019 |
| 1394C9G1(Rev−) | C (T/F) | 0.031 | 0.093 |
| Ce704809221_1B3 | C (T/F) | 0.084 | 0.395 |
| CNE19 | BC | 0.075 | >10 |
| CNE20 | BC | 0.002 | 0.005 |
| CNE21 | BC | 0.047 | 0.124 |
| CNE17 | BC | 1.180 | 4.853 |
| CNE30 | BC | 0.261 | 0.678 |
| CNE52 | BC | 1.991 | 9.763 |
| CNE53 | BC | 0.013 | 0.058 |
| CNE58 | BC | 0.165 | 0.476 |
| MS208.A1 | A | >10 | >10 |
| Q23.17 | A | 0.005 | 0.015 |
| Q461.e2 | A | >10 | >10 |
| Q769.d22 | A | >10 | >10 |
| Q259.d2.17 | A | >10 | >10 |
| Q842.d12 | A | >10 | >10 |
| 3415.v1.c1 | A | >10 | >10 |
| 3365.v2.c2 | A | 0.057 | 0.200 |
| 191955_A11 | A (T/F) | >10 | >10 |
| 191084 B7-19 | A (T/F) | 0.026 | 0.108 |
| 9004SS_A3_4 | A (T/F) | 0.012 | 0.032 |
| T257-31 | CRF02_AG | >10 | >10 |
| 928-28 | CRF02_AG | 0.616 | 2.396 |
| 263-8 | CRF02_AG | 0.416 | 5.714 |
| T250-4 | CRF02_AG | 0.002 | 0.005 |
| T251-18 | CRF02_AG | 0.399 | 2.292 |
| T278-50 | CRF02_AG | 1.713 | >10 |
| T255-34 | CRF02_AG | >10 | >10 |
| 211-9 | CRF02_AG | 0.065 | 0.403 |
| 235-47 | CRF02_AG | 0.058 | 0.224 |
| 620345.c01 | CRF01_AE | >10 | >10 |
| CNE8 | CRF01_AE | >10 | >10 |
| C1080.c03 | CRF01_AE | >10 | >10 |
| R2184.c04 | CRF01_AE | >10 | >10 |
| R1166.c01 | CRF01_AE | >10 | >10 |
| R3265.c06 | CRF01_AE | >10 | >10 |
| C2101.c01 | CRF01_AE | >10 | >10 |
| C3347.c11 | CRF01_AE | >10 | >10 |
| C4118.c09 | CRF01_AE | >10 | >10 |
| CNE5 | CRF01_AE | >10 | >10 |
| BJOX009000.02.4 | CRF01_AE | >10 | >10 |
| BJOX015000.11.5 | CRF01_AE (T/F) | >10 | >10 |
| BJOX010000.06.2 | CRF01_AE (T/F) | >10 | >10 |
| BJOX025000.01.1 | CRF01_AE (T/F) | >10 | >10 |
| BJOX028000.10.3 | CRF01_AE (T/F) | >10 | >10 |
| X1193_c1 | G | 0.070 | 0.207 |
| P0402_c2_11 | G | 0.008 | 0.024 |
| X1254_c3 | G | 0.063 | 0.239 |
| X2088_c9 | G | 0.003 | 0.010 |
| X2131_C1_B5 | G | 0.014 | 0.056 |
| P1981_C5_3 | G | 0.004 | 0.013 |
| X1632_S2_B10 | G | >10 | >10 |
| 3016.v5.c45 | D | >10 | >10 |
| A07412M1.vrc12 | D | 0.011 | 0.037 |
| 231965.c01 | D | >10 | >10 |
| 231966.c02 | D | >10 | >10 |
| 191821_E6_1 | D (T/F) | >10 | >10 |
| 3817.v2.c59 | CD | 0.706 | 4.492 |
| 6480.v4.c25 | CD | 0.006 | 0.023 |
| 6952.v1.c20 | CD | 0.023 | 0.086 |
| 6811.v7.c18 | CD | 0.003 | 0.009 |
| 89-F1_2_25 | CD | >10 | >10 |
| 3301.v1.c24 | AC | 0.018 | 0.049 |
| 6041.v3.c23 | AC | >10 | >10 |
| 6540.v4.c1 | AC | >10 | >10 |
| 6545.v4.c1 | AC | >10 | >10 |
| 0815.v3.c3 | ACD | 0.043 | 0.197 |
| 3103.v3.c10 | ACD | 0.024 | 0.061 |

TABLE 10

IC50 and IC80 values in TZM-bl assay for PGT121

| Virus ID | PGT121 Clade | IC50 | IC80 |
|---|---|---|---|
| 6535.3 | B | 0.003 | 0.010 |
| QH0692.42 | B | 0.498 | 8.507 |
| SC422661.8 | B | 0.079 | 0.373 |
| PV0.4 | B | 0.094 | 0.450 |
| TRO.11 | B | 0.011 | 0.037 |
| AC10.0.29 | B | 0.019 | 0.060 |
| RHPA4259.7 | B | 0.013 | 0.046 |
| THRO4156.18 | B | >10 | >10 |
| REJO4541.67 | B | >10 | >10 |
| TRJO4551.58 | B | 0.802 | >10 |
| WITO4160.33 | B | 0.301 | 3.200 |
| CAAN5342.A2 | B | 0.008 | 0.026 |
| WEAU_d15_410_787 | B (T/F) | 0.017 | 0.062 |
| 1006_11_C3_1601 | B (T/F) | 0.002 | 0.008 |
| 1054_07_TC4_1499 | B (T/F) | 0.041 | 0.299 |
| 1056_10_TA11_1826 | B (T/F) | 0.034 | 0.148 |
| 1012_11_TC21_3257 | B (T/F) | 0.008 | 0.034 |
| 6240_08_TA5_4622 | B (T/F) | 0.068 | 0.231 |
| 6244_13_B5_4576 | B (T/F) | 0.172 | 1.471 |
| 62357_14_D3_4589 | B (T/F) | 6.215 | >10 |
| SC05_8C11_2344 | B (T/F) | 0.030 | 0.108 |
| Du156.12 | C | 0.006 | 0.019 |
| Du172.17 | C | 0.062 | 0.531 |
| Du422.1 | C | 0.017 | 0.088 |

TABLE 10-continued

IC50 and IC80 values in TZM-bl assay for PGT121

| Virus ID | PGT121 Clade | IC50 | IC80 |
|---|---|---|---|
| ZM197M.PB7 | C | >10 | >10 |
| ZM214M.PE15 | C | 0.288 | 2.456 |
| ZM233M.PB6 | C | 2.809 | >10 |
| ZM249M.PL1 | C | >10 | >10 |
| ZM53M.PB12 | C | 0.001 | 0.005 |
| ZM109F.PB4 | C | 8.924 | >10 |
| ZM135M.PE10a | C | 0.730 | 5.727 |
| CAP45.2.00.G3 | C | 1.300 | >10 |
| CAP210.2.00.E8 | C | >10 | >10 |
| HIV-001428-2.42 | C | 0.020 | 0.126 |
| HIV-0013095-2.11 | C | >10 | >10 |
| HIV-16055-2.3 | C | 0.772 | 7.986 |
| HIV-16845-2.22 | C | 8.512 | >10 |
| Ce1086_B2 | C (T/F) | 0.003 | 0.016 |
| Ce0393_C3 | C (T/F) | >10 | >10 |
| Ce1176_A3 | C (T/F) | 0.022 | 0.063 |
| Ce2010_F5 | C (T/F) | >10 | >10 |
| Ce0682_E4 | C (T/F) | >10 | >10 |
| Ce1172_H1 | C (T/F) | 0.007 | 0.030 |
| Ce2060_G9 | C (T/F) | >10 | >10 |
| Ce703010054_2A2 | C (T/F) | >10 | >10 |
| BF1266.431a | C (T/F) | >10 | >10 |
| 246FC1G | C (T/F) | 0.082 | 0.363 |
| 249MB10 | C (T/F) | >10 | >10 |
| ZM247v1(Rev−) | C (T/F) | 0.036 | 0.123 |
| 7030102001E5(Rev−) | C (T/F) | 0.016 | 0.042 |
| 1394C9Gl(Rev−) | C (T/F) | 0.823 | 6.227 |
| Ce704809221_1B3 | C (T/F) | 0.043 | 0.285 |
| CNE19 | BC | 0.012 | 0.083 |
| CNE20 | BC | 0.003 | 0.006 |
| CNE21 | BC | 0.009 | 0.031 |
| CNE17 | BC | 3.962 | >10 |
| CNE30 | BC | 0.088 | 0.288 |
| CNE52 | BC | 4.914 | >10 |
| CNE53 | BC | 0.014 | 0.062 |
| CNE58 | BC | >10 | >10 |
| MS208.A1 | A | >10 | >10 |
| Q23.17 | A | 0.005 | 0.017 |
| Q461.e2 | A | >10 | >10 |
| Q769.d22 | A | >10 | >10 |
| Q259.d2.17 | A | 3.071 | >10 |
| Q842.d12 | A | 0.010 | 0.037 |
| 3415.v1.c1 | A | >10 | >10 |
| 3365.v2.c2 | A | 0.243 | 2.133 |
| 191955_A11 | A (T/F) | >10 | >10 |
| 191084 B7-19 | A (T/F) | 0.038 | 0.118 |
| 9004SS_A3_4 | A (T/F) | 0.006 | 0.016 |
| T257-31 | CRF02_AG | >10 | >10 |
| 928-28 | CRF02_AG | >10 | >10 |
| 263-8 | CRF02_AG | 0.647 | 4.680 |
| T250-4 | CRF02_AG | 0.003 | 0.009 |
| T251-18 | CRF02_AG | 5.183 | >10 |
| T278-50 | CRF02_AG | >10 | >10 |
| T255-34 | CRF02_AG | 2.631 | >10 |
| 211-9 | CRF02_AG | 0.866 | 6.631 |
| 235-47 | CRF02_AG | 0.259 | 1.601 |
| 620345.c01 | CRF01_AE | >10 | >10 |
| CNE8 | CRF01_AE | >10 | >10 |
| C1080.c03 | CRF01_AE | >10 | >10 |
| R2184.c04 | CRF01_AE | >10 | >10 |
| R1166.c01 | CRF01_AE | >10 | >10 |
| R3265.c06 | CRF01_AE | >10 | >10 |
| C2101.c01 | CRF01_AE | >10 | >10 |
| C3347.H1 | CRF01_AE | >10 | >10 |
| C4118.c09 | CRF01_AE | >10 | >10 |
| CNE5 | CRF01_AE | >10 | >10 |
| BJOX009000.02.4 | CRF01_AE | 9.001 | >10 |
| BJOX015000.11.5 | CRF01_AE (T/F) | >10 | >10 |
| BJOX010000.06.2 | CRF01_AE (T/F) | >10 | >10 |
| BJOX025000.01.1 | CRF01_AE (T/F) | >10 | >10 |
| BJOX028000.10.3 | CRF01_AE (T/F) | >10 | >10 |
| X1193_c1 | G | 0.022 | 0.088 |
| P0402_c2_11 | G | 0.007 | 0.022 |
| X1254_c3 | G | 0.029 | 0.085 |
| X2088_c9 | G | 0.007 | 0.022 |
| X2131_C1_B5 | G | 0.011 | 0.037 |
| P1981_C5_3 | G | 0.002 | 0.009 |
| X1632_S2_B10 | G | >10 | >10 |
| 3016.v5.c45 | D | >10 | >10 |
| A07412M1.vrc12 | D | 0.034 | 0.255 |
| 231965-c01 | D | >10 | >10 |
| 231966.c02 | D | >10 | >10 |
| 191821_E6_1 | D (T/F) | >10 | >10 |
| 3817.v2.c59 | CD | >10 | >10 |
| 6480.v4.c25 | CD | 0.008 | 0.029 |
| 6952.v1.c20 | CD | 0.049 | 0.348 |
| 6811.v7.c18 | CD | 0.002 | 0.007 |
| 89-F1_2_25 | CD | >10 | >10 |
| 3301.v1.c24 | AC | 0.013 | 0.041 |
| 6041.v3.c23 | AC | >10 | >10 |
| 6540.v4.c1 | AC | >10 | >10 |
| 6545.v4.c1 | AC | >10 | >10 |
| 0815.v3.c3 | ACD | 0.017 | 0.085 |
| 3103.v3.c10 | ACD | 0.024 | 0.073 |

TABLE 11

IC50 and IC80 values in TZM-bl assay of the 1:1:1 combination of NC37, BG1, and BG18 against a 118-virus panel.

| Virus ID | Titer in TZM.bl cells (ug/ml) NC37 + BG1 + BG18 Clade | IC50 | IC80 |
|---|---|---|---|
| 6535.3 | B | 0.006 | 0.030 |
| QH0692.42 | B | 0.033 | 0.130 |
| SC422661.8 | B | 0.024 | 0.089 |
| PV0.4 | B | 0.012 | 0.050 |
| TRO.11 | B | 0.004 | 0.015 |
| AC10.0.29 | B | 0.006 | 0.016 |
| RHPA4259.7 | B | 0.210 | 1.669 |
| THRO4156.18 | B | >50 | >50 |
| REJO4541.67 | B | 0.199 | 0.696 |
| TRJO4551.58 | B | 0.938 | 7.063 |
| WITO4160.33 | B | 0.021 | 0.075 |
| CAAN5342.A2 | B | 0.036 | 0.162 |
| YU2.DG | B | 0.052 | 0.147 |
| WEAU_d15_410_787 | B (T/F) | 0.022 | 0.074 |
| 1006_11_C3_1601 | B (T/F) | 0.005 | 0.013 |
| 1054_07_TC4_1499 | B (T/F) | 0.022 | 0.122 |

TABLE 11-continued

IC50 and IC80 values in TZM-bl assay of the 1:1:1 combination
of NC37, BG1, and BG18 against a 118-virus panel.

| Virus ID | Clade | Titer in TZM.bl cells (ug/ml) NC37 + BG1 + BG18 | |
|---|---|---|---|
| | | IC50 | IC80 |
| 1056_10_TA11_1826 | B (T/F) | 0.031 | 0.266 |
| 1012_11_TC21_3257 | B (T/F) | 0.012 | 0.055 |
| 6240_08_TA5_4622 | B (T/F) | 0.009 | 0.028 |
| 6244_13_B5_4576 | B (T/F) | 0.045 | 0.216 |
| 62357_14_D3_4589 | B (T/F) | 0.840 | 5.585 |
| SC05_8C11_2344 | B (T/F) | 0.045 | 0.083 |
| Du156.12 | C | 0.018 | 0.050 |
| Du172.17 | C | >50 | >50 |
| Du422.1 | C | 0.076 | 0.347 |
| ZM197M.PB7 | C | 4.123 | >50 |
| ZM214M.PL15 | C | >50 | >50 |
| ZM233M.PB6 | C | 7.814 | >50 |
| ZM249M.PL1 | C | 2.916 | 17.336 |
| ZM53M.PB12 | C | >50 | >50 |
| ZM109F.PB4 | C | >50 | >50 |
| ZM135M.PL10a | C | 6.018 | 31.451 |
| CAP45.2.00.G3 | C | 0.251 | 1.097 |
| CAP210.2.00.E8 | C | 19.144 | >50 |
| HIV-001428-2.42 | C | 0.029 | 0.075 |
| HIV-0013095-2.11 | C | 31.333 | >50 |
| HIV-16055-2.3 | C | 12.372 | 43.320 |
| HIV-16845-2.22 | C | 0.092 | 0.316 |
| Ce1086_B2 | C (T/F) | 2.088 | 13.998 |
| Ce0393_C3 | C (T/F) | >50 | >50 |
| Ce1176_A3 | C (T/F) | 0.013 | 0.030 |
| Ce2010_F5 | C (T/F) | >50 | >50 |
| Ce0682_E4 | C (T/F) | >50 | >50 |
| Ce1172_H1 | C (T/F) | 0.017 | 0.047 |
| Ce2060_G9 | C (T/F) | >50 | >50 |
| Ce703010054_2A2 | C (T/F) | >50 | >50 |
| BF1266.431a | C (T/F) | 45.589 | >50 |
| 246F C1G | C (T/F) | 0.172 | 1.220 |
| 249M B10 | C (T/F) | 4.422 | 17.159 |
| ZM247v1(Rev−) | C (T/F) | 6.417 | >50 |
| 7030102001E5(Rev−) | C (T/F) | 0.011 | 0.035 |
| 1394C9G1(Rev−) | C (T/F) | 0.078 | 1.405 |
| Ce704809221_1B3 | C (T/F) | 10.937 | >50 |
| CNE19 | BC | 1.576 | 17.656 |
| CNE20 | BC | 0.008 | 0.024 |
| CNE21 | BC | 0.009 | 0.022 |
| CNE17 | BC | 0.195 | 0.709 |
| CNE30 | BC | 0.067 | 0.183 |
| CNE52 | BC | 0.077 | 0.199 |
| CNE53 | BC | 0.015 | 0.036 |
| CNE58 | BC | 0.055 | 0.206 |
| MS208.A1 | A | 2.393 | 17.933 |
| Q23.17 | A | 0.009 | 0.024 |
| Q461.e2 | A | >50 | >50 |
| Q769.d22 | A | 0.364 | 2.151 |
| Q259.d2.17 | A | >50 | >50 |
| Q842.d12 | A | 0.405 | 1.371 |
| 0260.v5.c36 | A | 0.018 | 0.055 |
| 3415.v1.c1 | A | 0.039 | 0.187 |
| 3365.v2.c2 | A | 0.020 | 0.049 |
| 191955_A11 | A (T/F) | 0.830 | 4.335 |
| 191084 B7-19 | A (T/F) | 0.029 | 0.071 |
| 9004SS_A3_4 | A (T/F) | 0.027 | 0.090 |
| T257-31 | CRF02_AG | >50 | >50 |
| 928-28 | CRF02_AG | 1.919 | 7.522 |
| 263-8 | CRF02_AG | 0.544 | 3.759 |
| T250-4 | CRF02_AG | 0.005 | 0.029 |
| T251-18 | CRF02_AG | 0.133 | 0.639 |
| T278-50 | CRF02_AG | 9.069 | 44.006 |
| T255-34 | CRF02_AG | 37.020 | >50 |
| 211-9 | CRF02_AG | 1.976 | 18.953 |
| 235-47 | CRF02_AG | 0.013 | 0.046 |
| 620345.c01 | CRF01_AE | 1.325 | 8.233 |
| CNE8 | CRF01_AE | >50 | >50 |
| C1080.c03 | CRF01_AE | 0.012 | 0.042 |
| R2184.c04 | CRF01_AE | 0.084 | 0.376 |
| R1166.c01 | CRF01_AE | >50 | >50 |
| C2101.c01 | CRF01_AE | >50 | >50 |
| C3347.H1 | CRF01_AE | >50 | >50 |

TABLE 11-continued

IC50 and IC80 values in TZM-bl assay of the 1:1:1 combination
of NC37, BG1, and BG18 against a 118-virus panel.

| Virus ID | Titer in TZM.bl cells (ug/ml) NC37 + BG1 + BG18 Clade | IC50 | IC80 |
|---|---|---|---|
| C4118.c09 | CRF01_AE | >50 | >50 |
| CNE5 | CRF01_AE | 1.465 | 6.578 |
| BJOX009000.02.4 | CRF01_AE | >50 | >50 |
| BJOX015000.11.5 | CRF01_AE (T/F) | >50 | >50 |
| BJOX010000.06.2 | CRF01_AE (T/F) | >50 | >50 |
| BJOX025000.01.1 | CRF01_AE (T/F) | >50 | >50 |
| BJOX028000.10.3 | CRF01_AE (T/F) | >50 | >50 |
| X1193_c1 | G | 0.036 | 0.130 |
| P0402_c2_11 | G | 0.023 | 0.088 |
| X1254_c3 | G | 0.016 | 0.038 |
| X2088_c9 | G | 0.007 | 0.021 |
| X2131_C1_B5 | G | 0.016 | 0.036 |
| P1981_C5_3 | G | 0.022 | 0.063 |
| X1632_S2_B10 | G | 0.275 | 0.986 |
| 3016.v5.c45 | D | 8.359 | >50 |
| A07412M1.vrc12 | D | 0.189 | 2.455 |
| 231965.c01 | D | >50 | >50 |
| 231966.c02 | D | >50 | >50 |
| 191821_E6_1 | D (T/F) | >50 | >50 |
| 3817.v2.c59 | CD | 0.582 | 2.883 |
| 6480.v4.c25 | CD | 0.108 | 0.476 |
| 6952.vl.c20 | CD | 0.011 | 0.027 |
| 6811.v7.c18 | CD | 0.009 | 0.035 |
| 89-F1_2_25 | CD | 5.379 | >50 |
| 3301.v1.c24 | AC | 0.074 | 0.260 |
| 6041.v3.c23 | AC | 0.085 | 0.233 |
| 6540.v4.c1 | AC | >50 | >50 |
| 6545.v4.c1 | AC | >50 | >50 |
| 0815.v3.c3 | ACD | 0.071 | 0.321 |
| 3103.v3.c10 | ACD | 0.009 | 0.017 |

BG18

Figures 2A, 2B, 2C, 2D:
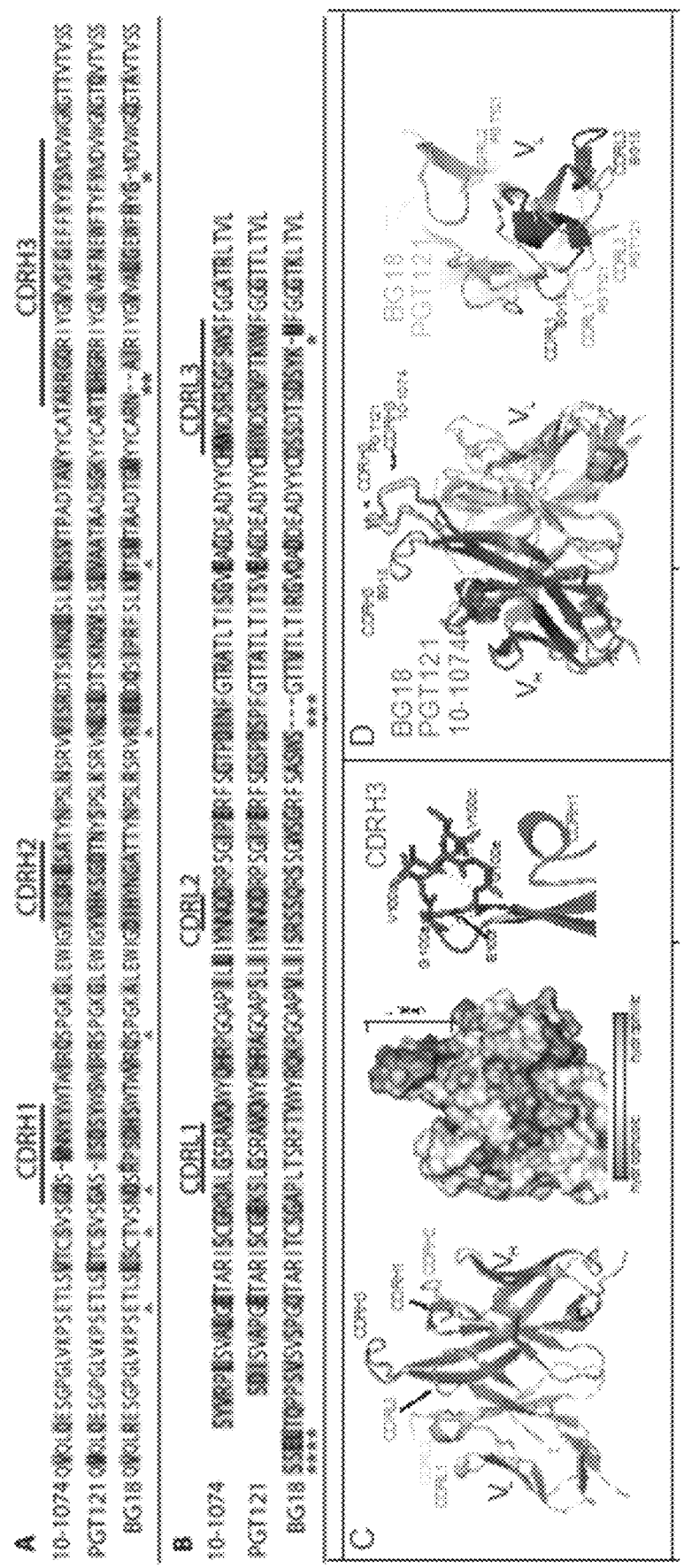
FIGS. 2A, 2B, 2C, 2D, 2E, 2F, 2G represent sequence and structural analysis of the BG18 bNab.
Figures 6A, 6B, 6C, 6D:
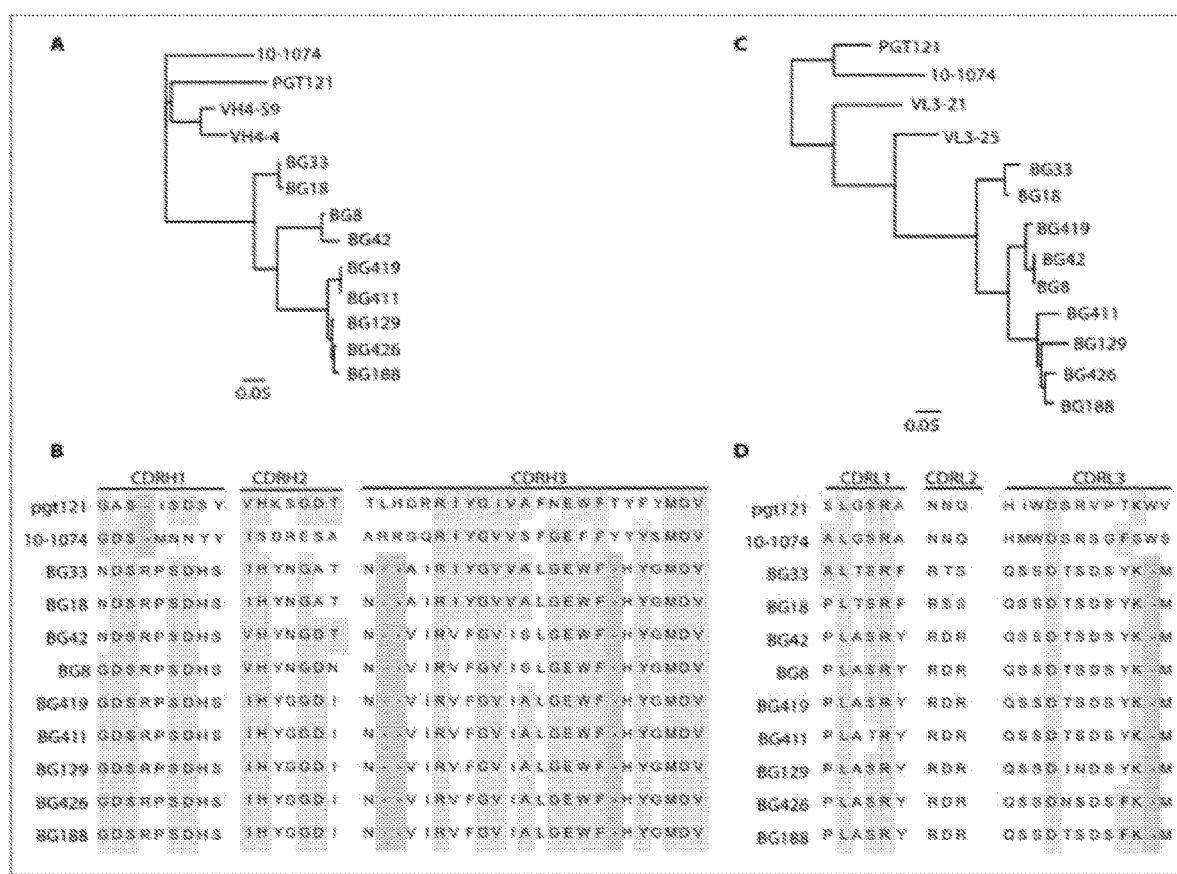
FIGS. 6A, 6B, 6C, 6D represent sequence comparison between BG18, PGT121 and 10-1074.

At the amino acid level BG18 is 63% and 62% identical to the heavy chains of 10-1074 and PGT121, respectively, both of which arise from a $V_H4$-59 germline precursor. BG18 arises from the closely related (90.8% identity) germline gene $V_H4$-4 (FIG. 6A). Alignment of the complementarity determining regions (CDRs) of the heavy chains of PGT121, 10-1074 and BG18 and its clonal variants shows a high degree of similarity between the CDRH1s and CDRH2s. The CDRH3 of BG18 is three residues shorter than PGT121/10-1074 (21 vs. 24 residues; FIG. 2A and FIG. 6B). In addition, BG18 shares 6 of the 7 mutations in the framework regions that are common to the PGT121 family (FIG. 2A), but unlike members of PGT121/10-1074 does not contain any insertions or deletions.

BG18 uses the VL gene segment $V_L2$-25, and is related by only 46% and 50% identity at the amino acid sequence level to the $V_L3$-2I gene segment used by PGT121 and 10-1074, respectively (FIG. 2B, FIG. 6C, and FIG. 6D). In addition, the light chains of BG18 and its variants are slightly more mutated compared to 10-1074 and PGT121, but as the heavy chains, do not contain any insertions or deletions. Thus, BG18 and its clonal variants display similar heavy chains to previously isolated PGT121/10-1074-class antibodies, but different light chains.

Figures 2E, 2F, 2G:
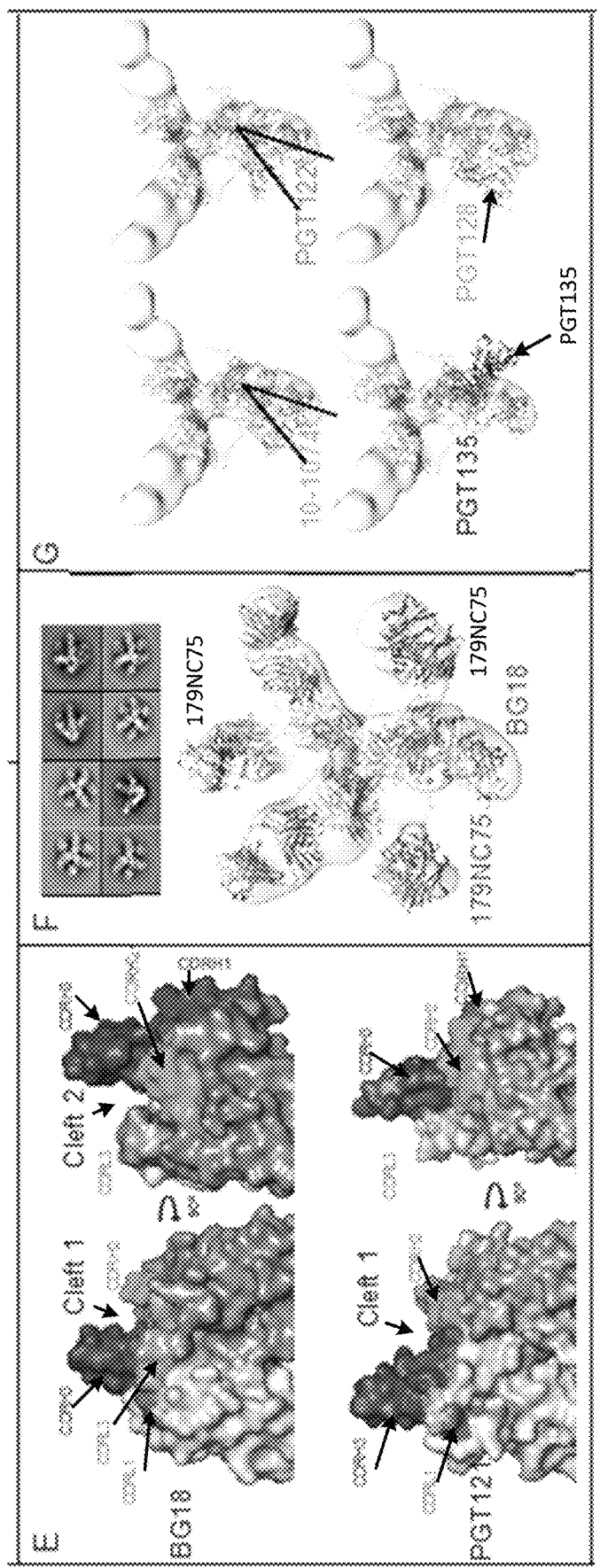
Figure 7:
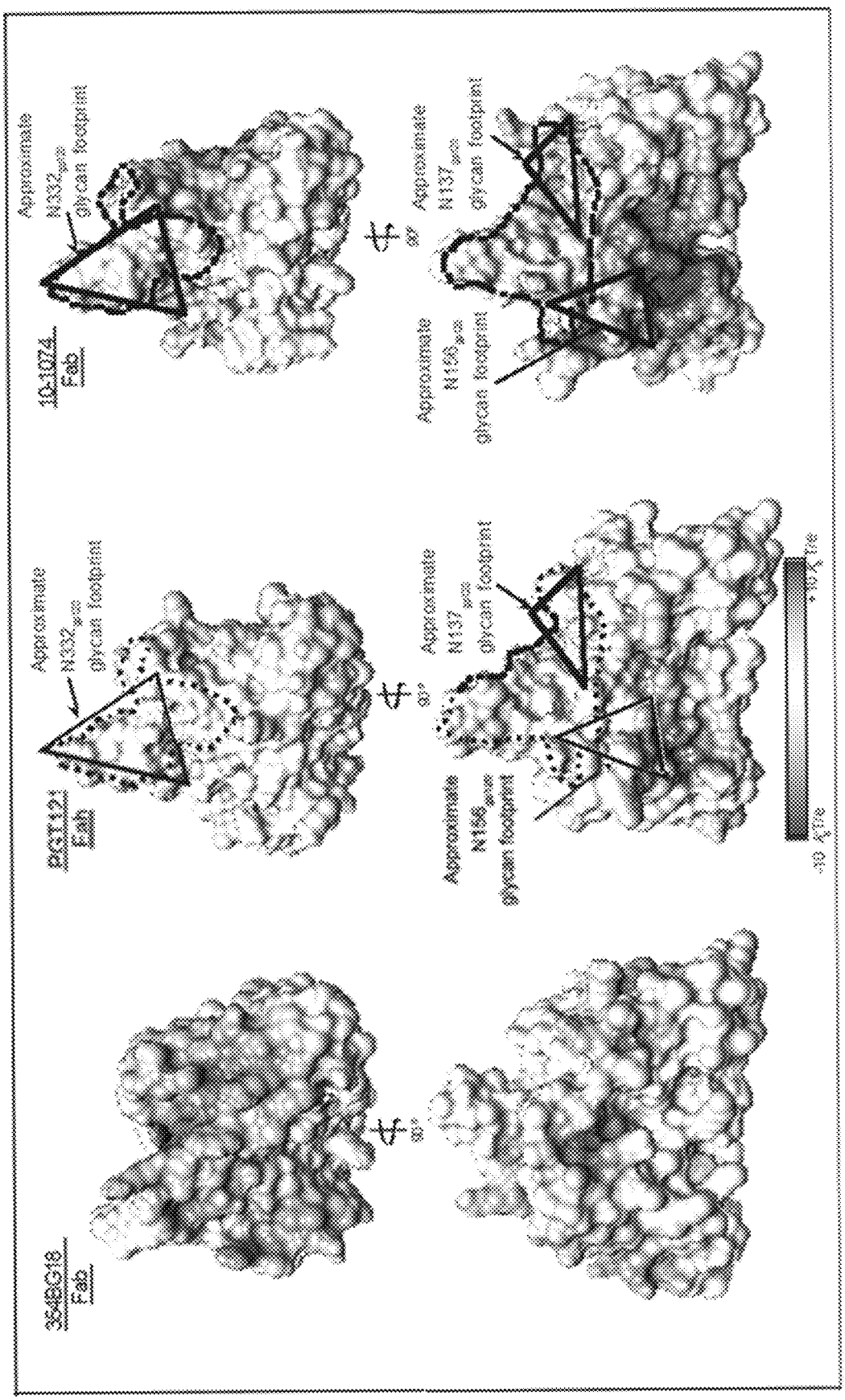
FIG. 7 represents the electrostatic potential of BG18. Electrostatic surface potentials of Fabs were calculated with APBS and surface representations were displayed in UCSF Chimera and shaded. The predicted binding interfaces are outlined with a dotted black line. The approximate footprints on the PGT121 and 10-1074 Fab surfaces of the gp120 glycans attached to $Asn137_{gp120}$, $Asn156_{gp120}$ and $Asn332_{gp120}$ are indicated with black triangles.

The 1.3 Å resolution crystal structure of BG18 Fab revealed that the CDR loops form a compact combining site, with the exception of CDRH3, which protrudes ~11 Å beyond the other CDRs, presenting a tip consisting predominantly of hydrophobic residues (FIG. 2C). Instead of extending fully, CDRH3 folds back on itself in a conformation stabilized by hydrogen bonds among CDRH3 residues Gly100a$_{HC}$, Val100b$_{HC}$, Val100c$_{HC}$, Gly100e$_{HC}$ and Glu100f$_{HC}$ (FIG. 2C). CDRL2 is disordered in the structure, suggesting that it can adopt multiple conformations in the unbound antibody. Superimposition of unbound BG18, PGT121 (PDB 4FQ1) and 10-1074 Fab (PDB 4FQ2) structures revealed that their $V_H$ domains aligned closely with the exception of the CDRH3, which is positioned over the $V_H$ domain in BG18 but leans markedly over $V_L$ in the PGT121 and 10-1074 Fab structures (FIG. 2D). Consistent with the low sequence identities relating the BG18 and PGT121 light chains (FIG. 2B, FIG. 6C and FIG. 6D), the aligned $V_L$ domains (root mean square deviations of 3.1 Å were found for superimposing 93 or 92 Cα atoms in comparisons of light chains in BG18-PGT121 and BG18-10-1074 superimpositions, respectively) showed differences in the orientations of all CDRL loops (FIG. 2D). Despite these differences, the cleft between CDRH2 and CDRH3 in PGT121 and 10-1074 is also seen in BG18 (FIG. 2E). Residues lining this cleft interacted with a complex-type A-glycan in a glycosylated PGT121 Fab structure and interact with the V-glycan attached to Asn137$_{gp120}$ in the PGT122-BG505 SOSIP complex structure (PDB 4TVP). BG18 displays a second cleft between CDRH3 and CDRL1/CDRL3, which cannot form in PGT121 and its clonal relatives due to the positioning of CDRH3 over the light chain in those antibodies (FIG. 2E). In addition to these structural differences, the electrostatic surface potential of the BG18 $V_H$-$V_L$ domains shows a different distribution of positively-charged patches compared with the surface potentials of PGT121 and 10-1074 (FIG. 7). Taken together, these results are consistent with differences in BG18 recognition of Env compared with recognition by the PGT121-related bNAbs.

To investigate how BG18 recognizes Env, a ~25 Å resolution negative stain single particle electron microscopy (EM) structure of BG505 SOSIP.664 trimer in complex with Fabs from BG18 and the CD4bs bNAb 179NC75 was resolved. Fitting the coordinates from the BG18 Fab crystal structure into the EM map (FIG. 2F) allowed comparison between the angles of approach and potential Env interactions of BG18 and other Asn332$_{gp120}$-V3 bNAbs (FIG. 2G). Similar to PGT122 (a variant of PGT121) and 10-1074, the CDRH3 of BG18 is predicted to interact with the Asn332$_{gp120}$ glycan and the $_{324}$GDIR$_{327}$ motif of gp120. However, whereas PGT122 and 10-1074 exhibit similar angles of approach for binding Env, BG18 contacts the Env trimer at a different angle, which is shifted by 34-41° relative to PGT122 and PGT124 (FIG. 2G).

Figures 9A, 9B, 9C, 9D, 9E, 9F:
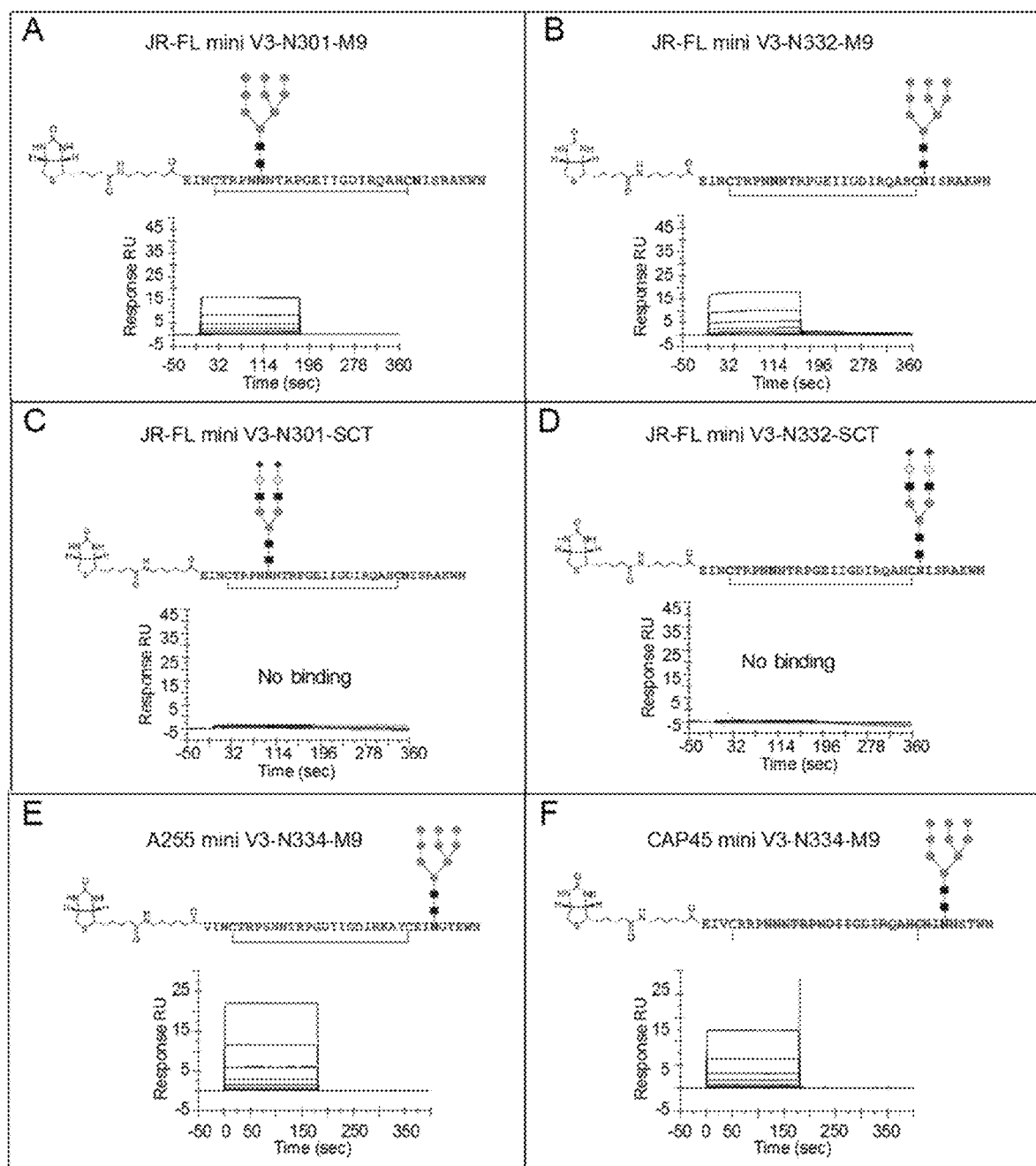
FIGS. 9A, 9B, 9C, 9D, 9E, 9F represent BG18 antibody binding to synthetic HIV-1 V3 glycopeptides. Biotin-tagged V3 glycopeptides were immobilized on a neotravidin chip and BG8 IgG was used as the analyte.

BG18 was evaluated for neutralization against a panel of HIV-1 pseudoviruses with deletions of specific A-linked glycosylation sites. The results indicated that none of the glycans at the base of V3 loop, with the exception of the Asn332$_{gp120}$, had an impact on neutralization activity (Table 12). Consistent with these data, BG18 bound preferentially to synthetic V3 glycopeptides containing oligomannose A-glycans at position Asn332$_{gp120}$ and not to glycopeptides containing complex-type A-glycans attached to this position or to other potential A-linked glycosylation sites within gp120 (FIG. 9). These data suggest that BG18 recognition properties are more similar to 10-1074 than to PGT121.

TABLE 12

IC50 and IC80 values in TZM-bl assay of BG18, BG8 PGT121 and control mAb 12A12 against selected V3 enelope mutants.

|  | BG8 | BG18 | PGT121 | 12A12 |
|---|---|---|---|---|
| BG505 (T332N) | 0.007 | 0.001 | 0.012 | 0.030 |
| N137A | 0.003 | 0.001 | 0.002 | 0.027 |
| N156A | 0.008 | 0.001 | 0.007 | 0.024 |
| N295A | 0.009 | 0.001 | 0.014 | 0.044 |
| N301A | 0.004 | 0.001 | 0.011 | 0.027 |
| N339A | 0.007 | 0.001 | 0.016 | ND |
| N386A | 0.004 | 0.001 | 0.015 | 0.030 |
| N392A | 0.005 | 0.001 | 0.006 | 0.012 |
| JR-CSF | 0.009 | 0.001 | 0.011 | 0.233 |
| N295A | 0.006 | 0.001 | 0.016 | 0.203 |
| N301A | 0.006 | 0.001 | 0.011 | 0.010 |
| N332A | >50 | >50 | >50 | 0.240 |
| N339A | 0.010 | 0.001 | 0.007 | 0.028 |
| N362A | 0.008 | 0.001 | 0.018 | 0.267 |
| N386A | 0.012 | 0.001 | 0.024 | 0.332 |
| N392A | 0.014 | 0.002 | 0.017 | 0.230 |
| G324A | 0.005 | 0.001 | 0.044 | 0.236 |
| D325A | 0.005 | 0.001 | 0.079 | 0.203 |
| I326A | 0.005 | 0.001 | 0.024 | 0.278 |
| R327A | 0.005 | 0.001 | 0.018 | 0.131 |
| Q328A | 0.023 | 0.001 | 0.057 | 0.038 |
| H330A | 0.050 | 0.001 | 0.017 | 0.288 |
| 92BR020 | 0.015 | 0.001 | 0.004 | 0.050 |
| N136A | 0.005 | 0.001 | 0.002 | 0.027 |
| N156A | 0.011 | 0.001 | 0.003 | 0.035 |
| N301A | 0.009 | 0.001 | 0.003 | 0.011 |
| N332A | >50 | >50 | 0.080 | 0.039 |
| N386A | 0.012 | 0.003 | 0.006 | 0.055 |
| N392A | 0.023 | 0.001 | 0.007 | 0.105 |
| D325A | 0.006 | 0.001 | 0.006 | 0.050 |
| I326A | 0.006 | 0.001 | 0.002 | 0.011 |
| R327A | 0.011 | 0.001 | 0.001 | 0.022 |
| Q328A | 0.018 | 0.001 | 0.002 | 0.028 |
| H330A | 0.018 | 0.001 | 0.003 | 0.073 |
| N136A + N332A | >50 | >50 | >1 | 0.025 |
| N156A + N332A | >50 | >50 | >1 | 0.023 |
| N301A + N332A | >50 | >50 | >1 | 0.007 |
| N136A + N156A + N301A | 0.001 | 0.001 | 0.001 | 0.013 |

NC37

Figures 8A, 8B, 8C:
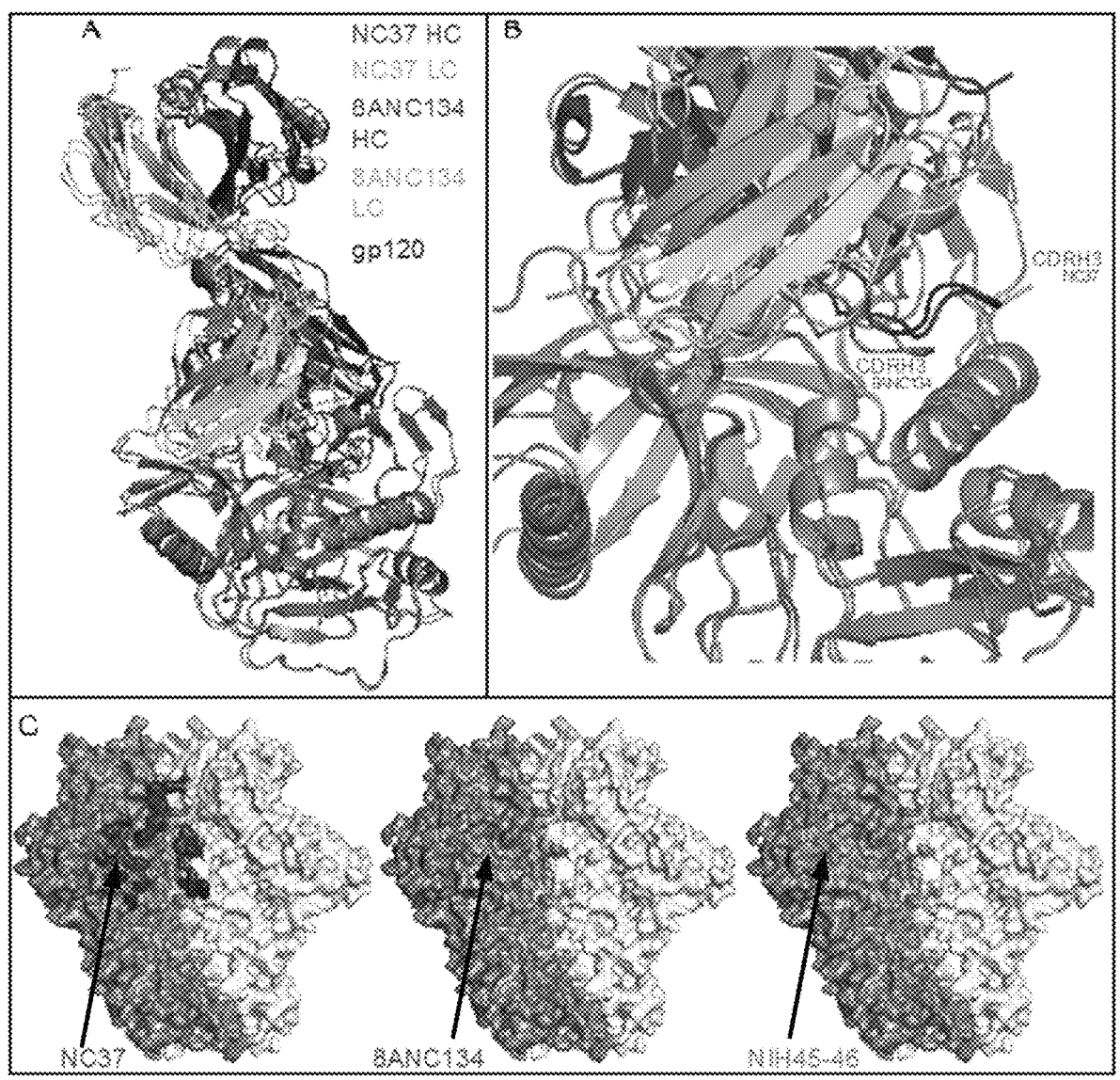
FIGS. 8A, 8B, 8C represent the NC37 Fab-gp120 complex structure.

A 2.7 Å resolution crystal structure of NC37 Fab (FIG. 1C) bound to a gp120 core verified that NC37 recognizes the CD4bs (FIGS. 8A and 8B). Based on sequence only, it was initially difficult to determine whether the V$_H$ of NC37 was derived from the V$_H$1-2 or V$_H$1-46 germline gene because some members of the NC37 family aligned to V$_H$1-2 while others aligned to V$_H$1-46 (Table 13). However, structural comparisons revealed that NC37 adopts a similar orientation and angle of binding as the V$_H$1-46-derived antibodies 8ANC131/134 (FIGS. 8A and 8B). As a consequence, NC37 uses its light chain to contact loop D residue Asn280$_{gp120}$, whereas V$_H$1-2-derived antibodies such as NIH45-46 use their heavy chains to contact Asn280$_{gp120}$. The CDRH3 of NC37 extends toward the gp120 inner domain, forming contacts between CDRH3 residue Tyr100G$_{HC}$ and gp120 inner domain residues Lys97$_{gp120}$ and Glu102$_{gp120}$. Superposing the NC37 Fab-gp120 complex onto a SOSIP trimer structure suggests that the NC37 CDRH3 makes contacts with the adjacent protomer within the Env trimer (FIG. 8C).

NC37 was isolated in 2010, whereas BG1 and BG18 were isolated from PBMCs collected in 2014. Available PBMCs were examined from 2010 and 2013 using PCR primers specific for BG1 and BG18. Whereas BG1 transcripts were detected at both time points, BG18 was first detected in 2013. This indicates that BG18 emerged between 2010 and 2013, while BG1 and NC37 developed earlier.

Autologous Neutralization

Figures 3A, 3B, 3C, 3D, 3E:
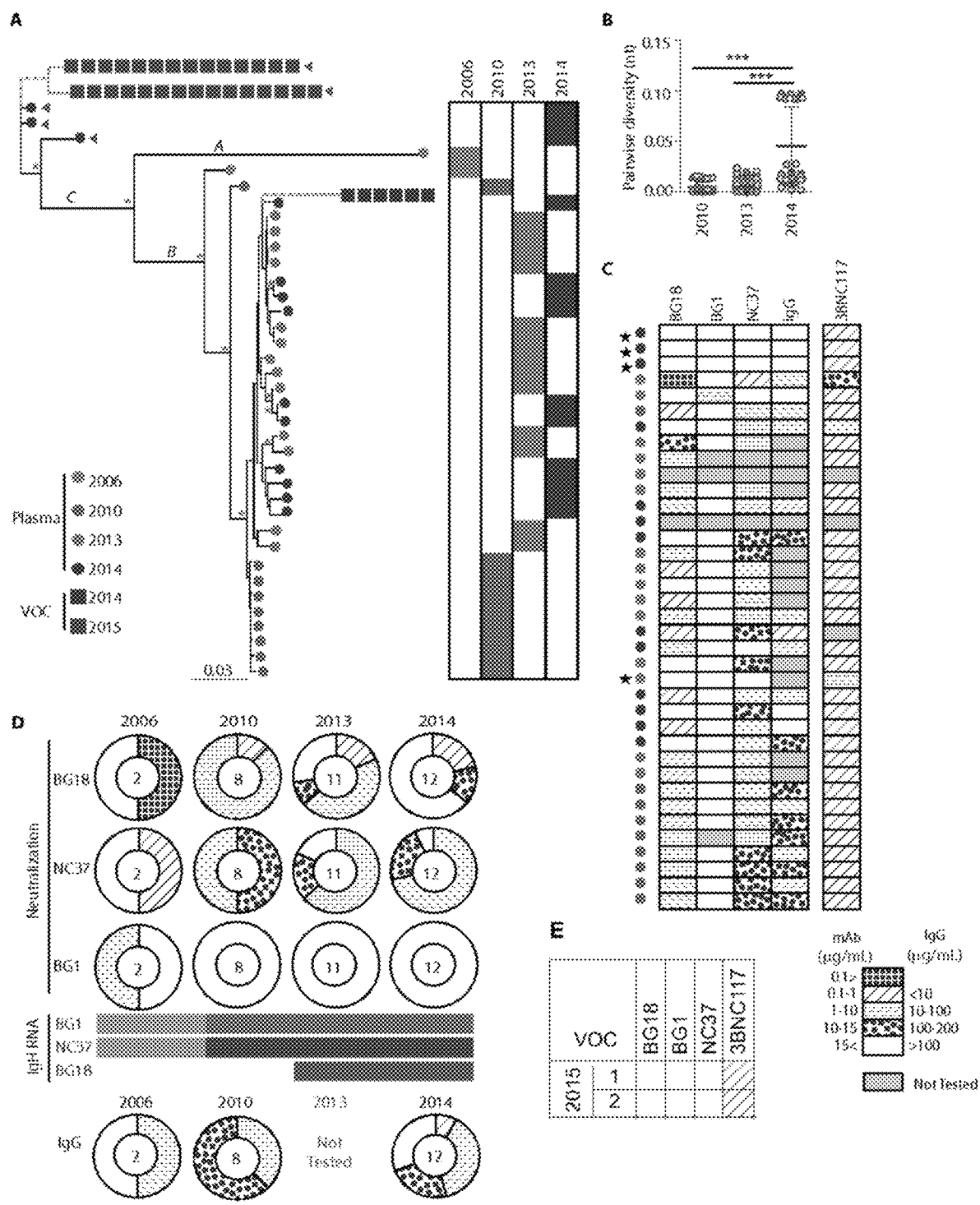
FIGS. 3A, 3B, 3C, 3D, 3E represent autologous plasma viruses in donor EB354.
Figures 10A, 10B, 10C:
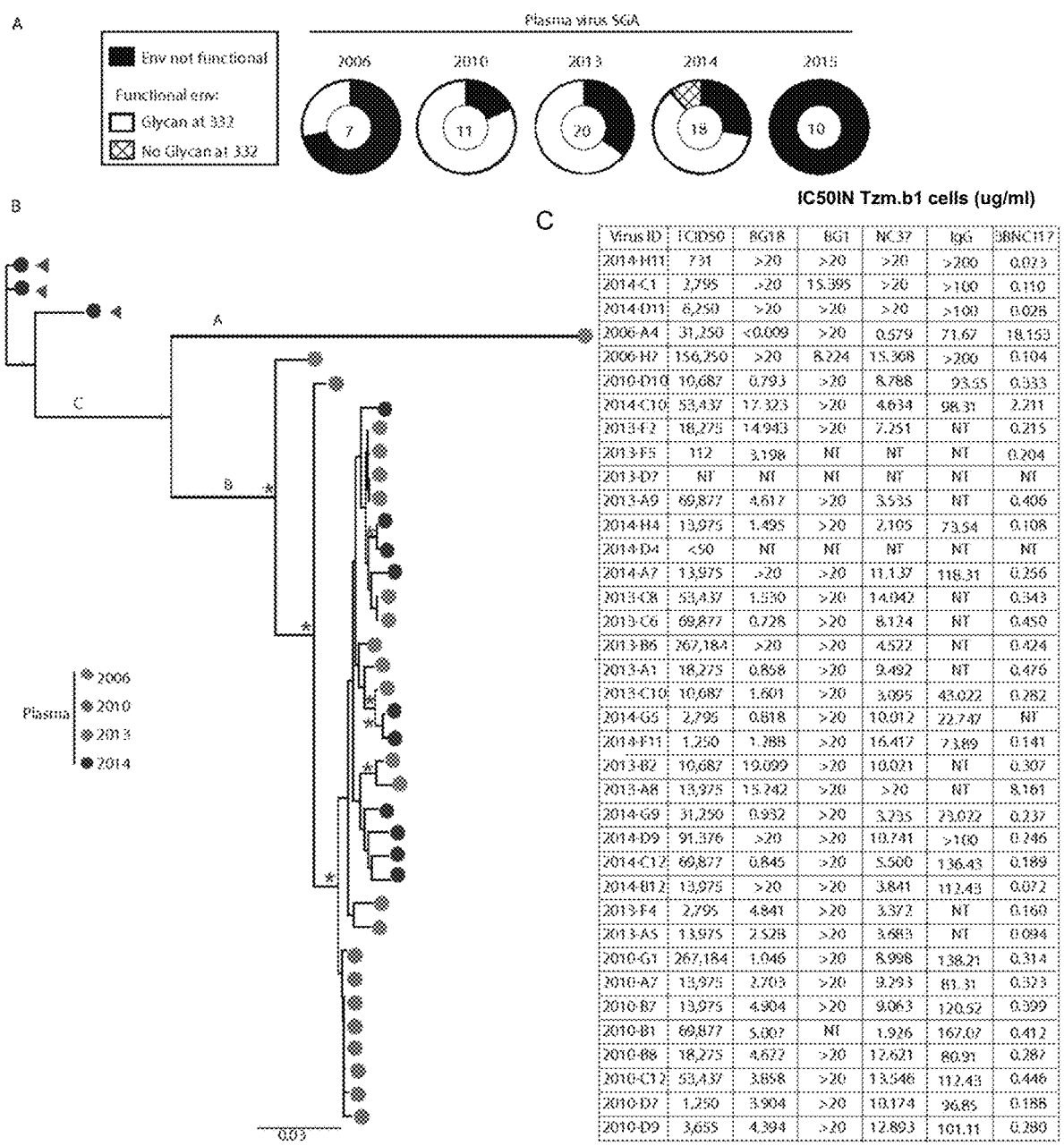
FIGS. 10A, 10B, 10C represent single genome env sequencing of plasma virus from donor EB354.

To examine the effects of the 3 bNAbs on autologous viruses, individual env genes from circulating plasma viruses were clonged by single-genome sequencing (SGS) from five different time points during 2006-2015 (2006, 2010, 2013, 2014 and 2015). Only 37 functional in-frame transcripts were recovered, in part due to viral load values below 400 copies/mL at all time points. Moreover, all sequences recovered from 2015 were non-functional (FIG. 10). The 37 functional sequences formed three clusters— Cluster A, contained one sequence from 2006 that was ~15% different from the rest of the sequences, Cluster B, the biggest cluster, contained sequences from all four time points and Cluster C contained 3 sequences, all from 2014 (FIG. 3A). In agreement with the new cluster of sequences that emerged in 2014, an increase in viral diversity was seen between 2013 and 2014 (FIG. 3B).

All 3 sequences in Cluster C contained mutations altering the A-linked glycosylation site at Asn332$_{gp120}$, whereas the other 34 sequences had an intact A-linked glycosylation site at Asn332$_{gp120}$ (FIG. 3A). In addition, all 3 sequences in Cluster C had an Asp282$_{gp120}$ residue that was not found in the other 34 sequences. Position 282$_{gp120}$ carries a Lys in 94.4% of all HIV-1 sequences in the Los Alamos Data Base, and Asp at this position is associated with resistance to CD4bs antibodies.

To determine the sensitivity of the functional Envs to the 3 autologous bNAbs, psuedoviruses were produced and tested in TZM-bl assays. Out of 35 pseudoviruses that were successfully produced, only 4 were resistant to all 3 bNAbs. These were Envs from Cluster C, found in the plasma from 2014, and one from 2013 (FIG. 3C and FIG. 10). The remaining 31 pseudoviruses (88.5% of all pseudoviruses) were sensitive to at least 1 of the 3 bNAbs. In addition, the pseudoviruses from 2006, 2010 and 2014 were tested for their sensitivity to the concurrent serum IgG isolated from the same time point as the viral env genes (plasma IgG from 2013 was not available for this assay). The results indicated that that 19 out of the 22 viruses tested were still neutralized by the contemporaneous IgG (FIG. 3C and FIG. 10).

BG18- and NC37-sensitive viruses, as well as viruses sensitive to the concurrent IgG, were found at all time points analyzed including the times when BG18 and NC37 were isolated (FIG. 3D) In contrast, most strains, with the exception of one virus from 2006, were resistant to BG1. This suggests that most of the autologous viruses in donor EB354 escaped from BG1, but failed to escape from BG18 and NC37 antibodies, thus indicating the breadth and potency of BG18 and NC37.

Although it was not possible to obtain viral sequences from plasma samples from 2015, it was possible to grow virus from two out of five EB354 CD4+ viral outgrowth cultures (VOCs). In both cases the cultures took over five weeks to become positive for the virus as measured by p24 ELISA. SGS sequences from both 2015 outgrowth cultures clustered closely with sequences from Cluster C and lacked the A-linked glycosylation site at $Asn332_{gp120}$ (FIG. 3A). In addition, all sequences showed $Asp282_{gp120}$. Consistent with these findings, culture supernatants from 2015 were resistant to all 3 bNAbs in TZM-bl assays (FIG. 3E).

In Vivo Efficacy of BG18, NC37 and BG1

Figures 4A, 4B, 4C:
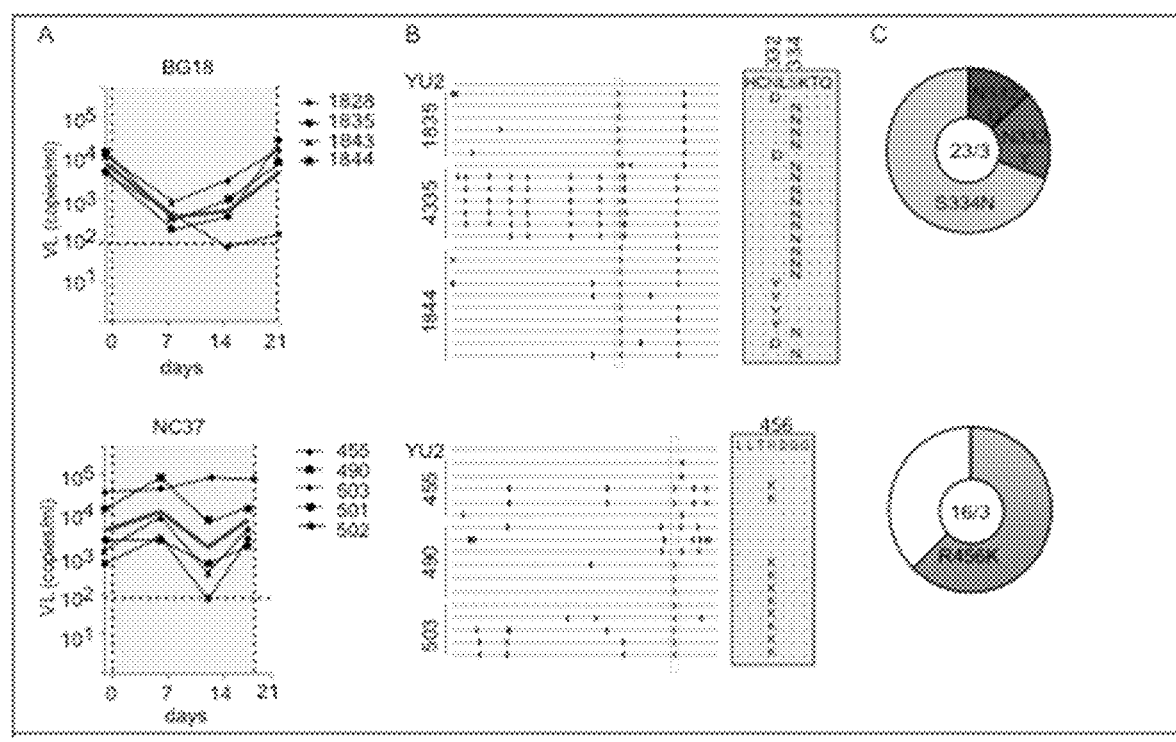
FIGS. 4A, 4B, 4C, 4D, 4E represent $HIV_{YU2}$-infected hu-mice treatment.
Figure 12A:
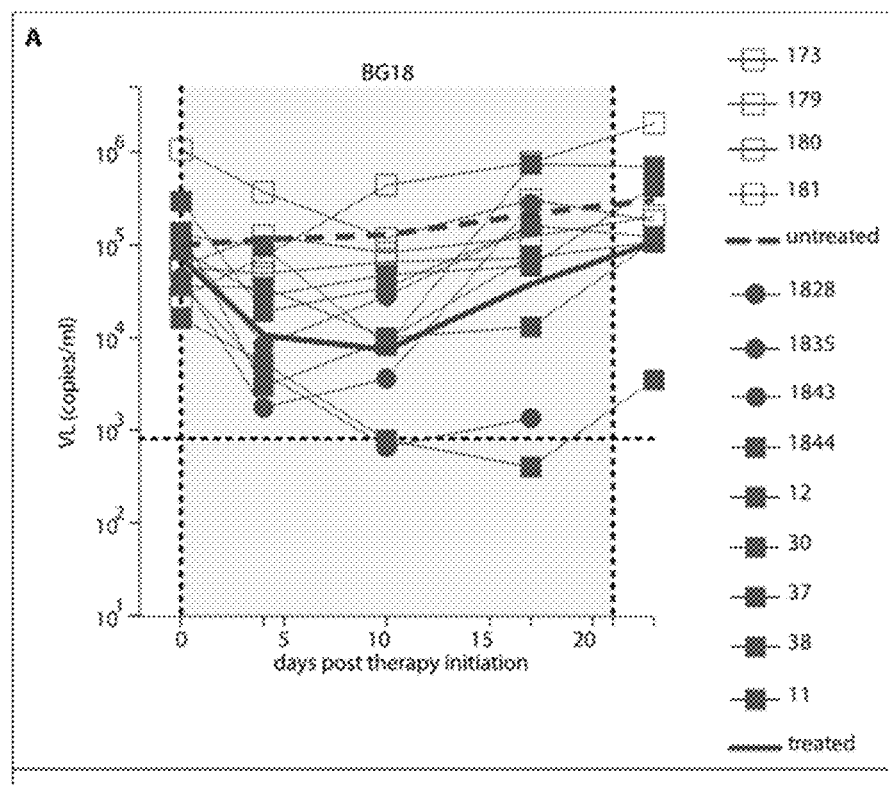
FIGS. 12A, 12B represent viral loads in HIV$_{YU2}$-infected, antibody treated humanized mice. Viral load values in HIVYU2-infected humanized mice before and after monotherapy with BG18 (FIG. 12A) and NC37 (FIG. 12B). The shaded area on the graph indicates the period of time during which antibody was given. Each graph shows two independent experiments indicated by circles (one experiment) and by squares (second experiment). Full and open shapes indicate treated and control mice, respectively. The dashed and full thick lines indicate the average values for control and treated mice, respectively.
Figure 12B:
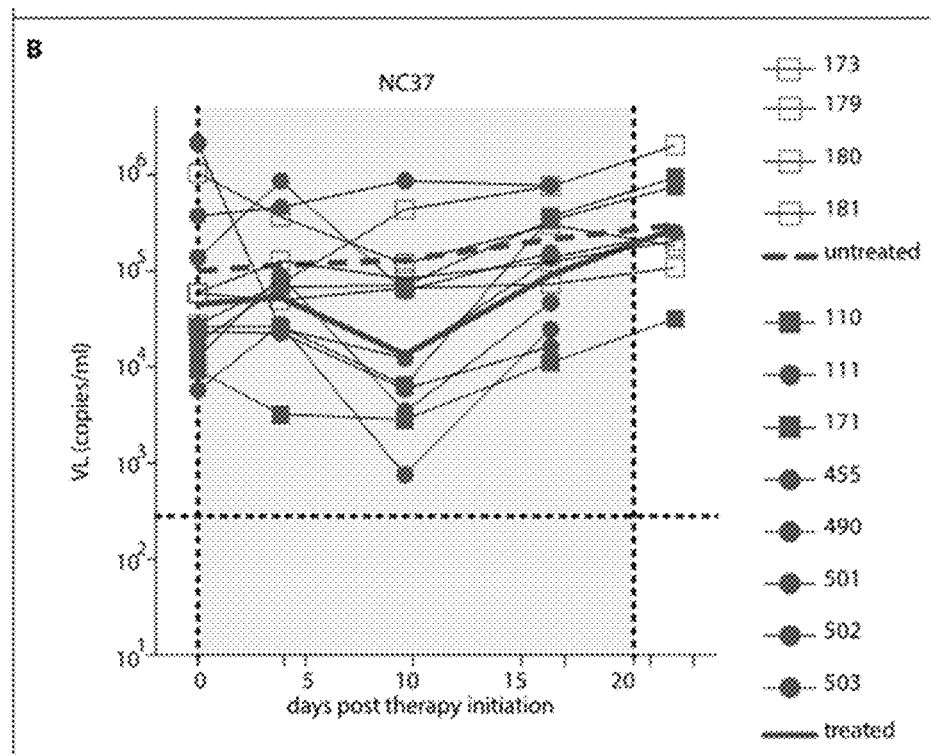

To determine whether BG18 or NC37 can independently exert selective pressure on HIV-1 in vivo, humanized mice (hu-mice) were infected with HIV-1$_{YU2}$ and the established infection was treated. BG1 showed poor activity against HIV-1$_{YU2}$ ($IC_{50}$=15.8 µg/mL) and therefore was used only in subsequent combination treatment experiments and not in monotherapy experiments. Similar to 10-1074, administration of BG18 or BG8, a less potent but still effective clonal variant, was associated with a rapid decrease (average 1.5 $log_{10}$) in viral load, followed by rebound viremia (FIG. 4A, FIG. 11, and FIG. 12). All rebounding viral sequences contained a mutation that altered the A-linked glycosylation site at $Asn332_{gp120}$ (FIGS. 4B and 4C). Monotherapy with NC37 also transiently suppressed viremia but the magnitude of the decrease in viral load was less profound than with BG18, average of 0.5 $log_{10}$ (FIG. 4A and FIG. 12). This indicates that BG18 and NC37 is effective to treat HIV, with BG18 having the most profound effects. The majority of the NC37-rebound viral Env sequences showed an R456K mutation that is associated with resistance to CD4bs antibodies (FIGS. 4B and 4C). This additionally indicates that BG18 and NC37 can select for HIV-1YU2 antibody resistant variants in vivo in hu-mice.

Figures 4D, 4E:
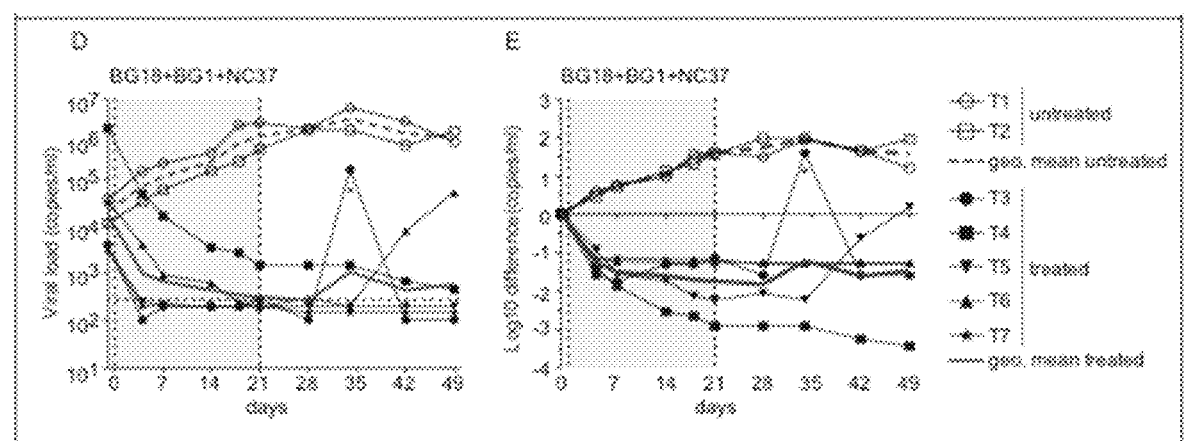

Combinations of antibodies can control HIV-1YU2 infection in hu-mice. To determine whether the combination of BG18, NC37 and BG1 can control viremia 5 HIV-1$_{YU2}$-infected hu-mice were treated with a 1:1:1 combination of the 3 bNAbs (BG18, NC37 and BG1). Shortly after administration of the 3 bNAbs, viral loads were reduced in all animals by an average of 1.74 $Log_{10}$, and, surprisingly, 4/5 mice showed virtually undetectable viral loads after 3 weeks (FIGS. 4D and 4E). Viremia rebounded in only one mouse, T6, and that occurred only 3 weeks after therapy was discontinued. The remaining 4 mice remarkably continued showing suppressed, or undetectable, viremia even after 4 weeks off therapy (FIGS. 4D and 4E). This indicates that, that whether applied individually but especially in combination, NC37, BG1, and especially BG18 are potent in durable suppression and neutralization of HIV-1 in vivo.

TABLE 13

Neutralizing Clones. Genetic characteristic of the 13 antibodies, representative variants from each of the three clones that showed neutralizing activity. The $V_H$, $V_L$ and level of mutations, as well as the sequence of the CDRH3 (based on IMGT definition) are indicated.

| Antibody | Closest VH | Closest VL | Somatic Mutations in V (nt) % VH | Somatic Mutations in V (nt) % VL | CDRH3 Sequence |
|---|---|---|---|---|---|
| NC37 | 1-2/1-46 | K3-20 | 28.8 | 27.9 | DNFGTRPVPGRGYYYGMDV (SEQ ID NO: 105) |
| NC133 | 1-46 | K3-20 | 28 | 23.2 | DNRGDRNVPGRGYYYGMDV (SEQ ID NO: 106) |
| NC102 | 1-2 | K3-20 | 27.1 | 22.2 | DNFGTRPVPGRGYYYGMDV (SEQ ID NO: 107) |
| AC40 | 1-46 | K3-20 | 33.5 | 21.1 | DNFGESHKGYTYGMDA (SEQ ID NO: 108) |
| AC41 | 1-46 | K3-20 | 30.1 | 21.5 | DNFGESHKGYTYGMDA (SEQ ID NO: 109) |
| AC72 | 1-46 | K3-20 | 29.8 | 20.8 | DNFGESHKGYTYGMDA (SEQ ID NO: 110) |
| BG8 | 4-4 | L3-25 | 25.4 | 20.5 | NVIRVFGVISLGEWFHYGMDV (SEQ ID NO: 4) |
| BG18 | 4-4 | L3-25 | 21.2 | 17.7 | NAIRIYGVVALGEWFHYGMDV (SEQ ID NO: 12) |
| BG33 | 4-4 | L3-25 | 25 | 18.4 | NVIRVFGVISLGEWFHYGMDV (SEQ ID NO: 28) |
| BG42 | 4-4 | L3-25 | 23.7 | 19.4 | NVIRVFGVISLGEWFHYGMDV (SEQ ID NO: 20) |
| BG1 | 3-49 | K1-39 | 27.2 | 19.9 | EQRNKDYRYGQEGFGYSYGMDV (SEQ ID NO: 76) |
| BG22 | 3-49 | K1-39 | 26.8 | 23.4 | EQRGGDGRYSGDGFGYPYGMDV (SEQ ID NO: 84) |

TABLE 13-continued

Neutralizing Clones. Genetic characteristic of the 13 antibodies, representative variants from each of the three clones that showed neutralizing activity. The $V_H$, $V_L$ and level of mutations, as well as the sequence of the CDRH3 (based on IMGT definition) are indicated.

| Antibody | Closest VH | Closest VL | Somatic Mutations in V (nt) % VH | VL | CDRH3 Sequence |
|---|---|---|---|---|---|
| BG47 | 3-49 | K1-39 | 27.1 | 22 | EQRGANGRYGGDGFGYSYGMDV (SEQ ID NO: 92) |

TABLE 13. Neutralizing Clones. Genetic characteristic of the 13 antibodies, representative variants from each of the three clones that showed neutralizing activity. The $V_H$, $V_L$ and level of mutations, as well as the sequence of the CDRH3 (based on IMGT definition) are indicated.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

The invention claimed is:

1. An isolated anti-HIV-1 antibody, or antigen binding portion thereof, comprising three heavy chain complementarity determining regions (CDRH 1, CDRH 2, and CDRH 3) and three light chain complementarity determining regions (CDRL 1, CDRL 2, and CDRL 3), wherein the CDRH 1, CDRH 2, CDRH 3, CDRL 1, CDRL 2 and CDRL 3 comprise the respective sequences of a CDR set selected from the group consisting of SEQ ID NOs: 2-4 and 6-8; SEQ ID NOs: 10-12 and 14-16; SEQ ID NOs: 18-20 and 22-24; SEQ ID NOs: 26-28 and 30-32, and SEQ ID NOs: 34-36 and 38-40; SEQ ID NOs: 42-44 and 46-48; SEQ ID NOs: 50-52 and 54-56; SEQ ID NOs: 58-60 and 62-64; SEQ ID NOs: 66-68 and 70-72; SEQ ID NOs: 74-76 and 78-80; SEQ ID NOs: 82-84 and 86-88; and SEQ ID NOs: 90-92 and 94-96.

2. The isolated anti-HIV-1 antibody of claim 1, or antigen binding portion thereof, comprising one or both of (i) a heavy chain comprising the amino acid sequence selected from the group consisting of SEQ ID NOs: 1, 9, 17, 25, 33, 41, 49, 57, 65, 73, 81, and 89 and (ii) a light chain comprising the amino acid sequence selected from the group consisting of SEQ ID NOs: 5, 13, 21, 29, 37, 45, 53, 61, 69, 77, 85, and 93.

3. The isolated anti-HIV-1 antibody of claim 2, or antigen binding portion thereof, wherein the heavy chain and the light chain comprise the respective sequences of SEQ ID NOs: 1 and 5; SEQ ID NOs: 9 and 13; SEQ ID NOs: 17 and 21; SEQ ID NOs: 25 and 29; SEQ ID NOs: 33 and 37; SEQ ID NOs: 41 and 45; SEQ ID NOs: 49 and 53; SEQ ID NOs: 57 and 61; SEQ ID NOs: 65 and 69; SEQ ID NOs: 73 and 77; SEQ ID NOs: 81 and 85; and SEQ ID NOs: 89 and 93.

4. The isolated anti-HIV-1 antibody of claim 1, or antigen binding portion thereof, wherein the antibody is a human antibody, a humanized antibody, or a chimeric antibody.

5. A pharmaceutical composition comprising (i) a first anti-HIV-1 antibody of claim 1, or antigen binding portion thereof, and (ii) a pharmaceutically acceptable carrier.

6. The pharmaceutical composition of claim 5, further comprising a second anti-HIV-1 antibody or antigen binding portion thereof.

7. The pharmaceutical composition of claim 6, wherein the second anti-HIV-1 antibody is selected from the group consisting of NC37, NC133, NC102, AC40, AC41, and AC72.

8. A method of treating an HIV-1 infection comprising: identifying a subject in need thereof, and administering to said subject a first therapeutic agent comprising a therapeutically effective amount of a first anti-HIV-1 antibody of claim 1, antigen binding portion thereof.

9. The method of claim 8, further comprising administering a second therapeutic agent.

10. The method of claim 9 wherein the second therapeutic agent is selected from the group consisting of a non-nucleoside reverse transcriptase inhibitor, a protease inhibitor, an entry or fusion inhibitor, an integrase inhibitor, and a second anti-HIV-1 antibody or antigen binding portion thereof.

11. The method of claim 10, wherein the second anti-HIV-1 antibody is selected from the group consisting of NC37, NC133, NC102, AC40, AC41, and AC72.

12. A vaccine composition comprising an anti-HIV-1 antibody of claim 1, or antigen binding portion thereof.

13. The pharmaceutical composition of claim 5 wherein the first anti-HIV-1 antibody comprises BG18 or BG1.

14. The isolated anti-HIV-1 antibody or antigen binding portion thereof of claim 1, wherein the CDRH 1, CDRH 2, CDRH 3, CDRL 1, CDRL 2 and CDRL 3 comprise the respective sequences of SEQ ID NOs: 10-12 and 14-16.

15. The isolated anti-HIV-1 antibody or antigen binding portion thereof of claim 3, wherein the heavy chain and the light chain comprise the respective sequences of SEQ ID NOs: 9 and 13.

16. The isolated anti-HIV-1 antibody or antigen binding portion thereof of claim 1, comprising a heavy chain variable region and a light chain variable region, wherein the heavy chain variable region comprises the amino acid sequence of SEQ ID NO: 9 and the light variable region comprises the amino acid sequence of SEQ ID NO: 13.

* * * * *